US009533002B2

(12) United States Patent
Narain et al.

(10) Patent No.: US 9,533,002 B2
(45) Date of Patent: Jan. 3, 2017

(54) METHODS OF TREATING A METABOLIC SYNDROME BY MODULATING HEAT SHOCK PROTEIN (HSP) 90-β

(71) Applicants: Niven Rajin Narain, Cambridge, MA (US); Rangaprasad Sarangarajan, Boylston, MA (US); Vivek K. Vishnudas, Newton, MA (US); Enxuan Jing, West Roxbury, MA (US)

(72) Inventors: Niven Rajin Narain, Cambridge, MA (US); Rangaprasad Sarangarajan, Boylston, MA (US); Vivek K. Vishnudas, Newton, MA (US); Enxuan Jing, West Roxbury, MA (US)

(73) Assignee: Berg LLC, Nashville, TN (US)

( * ) Notice: Subject to any disclaimer, the term of this patent is extended or adjusted under 35 U.S.C. 154(b) by 473 days.

(21) Appl. No.: 13/902,354

(22) Filed: May 24, 2013

(65) Prior Publication Data

US 2014/0154266 A1 Jun. 5, 2014

Related U.S. Application Data

(60) Provisional application No. 61/652,023, filed on May 25, 2012.

(51) Int. Cl.
*A61K 48/00* (2006.01)
*C07H 21/02* (2006.01)
(Continued)

(52) U.S. Cl.
CPC .......... *A61K 31/7056* (2013.01); *A61K 31/19* (2013.01); *A61K 31/192* (2013.01); *A61K 31/352* (2013.01); *A61K 31/366* (2013.01); *A61K 31/416* (2013.01); *A61K 31/713* (2013.01); *C07K 14/4702* (2013.01); *C07K 16/18* (2013.01); *C12N 15/113* (2013.01); *C12Q 1/6883* (2013.01); *G01N 33/5308* (2013.01); *G01N 33/6893* (2013.01);
(Continued)

(58) Field of Classification Search
USPC .......................................... 514/44; 536/24.5
See application file for complete search history.

(56) References Cited

U.S. PATENT DOCUMENTS 7,189,723 B2   3/2007   Mitchell et al.
7,531,323 B2   5/2009   Larsen et al.
(Continued)

FOREIGN PATENT DOCUMENTS

CN   102112478   6/2011
CN   102227221   10/2011
(Continued)

OTHER PUBLICATIONS

Didelot et al. (Cell Death and Differentiation, 2008 vol. 15:859-866).*
(Continued)

*Primary Examiner* — Terra C Gibbs
(74) *Attorney, Agent, or Firm* — McCarter & English, LLP; Elizabeth A. Hanley, Esq.; Jill Mello

(57) ABSTRACT

The invention provides methods of treatment of metabolic syndrome with HSP90 inhibitors, particularly HSP90β inhibitors. The invention provides methods of diagnosis and monitoring of metabolic syndrome using HSP90, particularly HSP90β, expression and activity level.

32 Claims, 23 Drawing Sheets

(51) Int. Cl.

| | | |
|---|---|---|
| C07H 21/04 | (2006.01) | |
| C12N 15/11 | (2006.01) | |
| A61K 31/7056 | (2006.01) | |
| A61K 31/192 | (2006.01) | |
| A61K 31/352 | (2006.01) | |
| A61K 31/416 | (2006.01) | |
| A61K 31/713 | (2006.01) | |
| C07K 16/18 | (2006.01) | |
| C12Q 1/68 | (2006.01) | |
| G01N 33/53 | (2006.01) | |
| C07K 14/47 | (2006.01) | |
| C12N 15/113 | (2010.01) | |
| G01N 33/68 | (2006.01) | |
| A61K 31/19 | (2006.01) | |
| A61K 31/366 | (2006.01) | |

(52) U.S. Cl.
CPC ....... *C12N 2310/11* (2013.01); *C12N 2310/14* (2013.01); *G01N 2800/042* (2013.01)

(56) References Cited

U.S. PATENT DOCUMENTS

| | | | |
|---|---|---|---|
| 7,674,795 B2 | 3/2010 | Mailliet et al. | |
| 7,678,803 B2 | 3/2010 | Huang et al. | |
| 7,820,658 B2 | 10/2010 | Dymock et al. | |
| 7,855,192 B2 | 12/2010 | Ashley et al. | |
| 8,183,279 B2 | 5/2012 | Eggenweiler et al. | |
| 8,217,050 B2 | 7/2012 | Moffat et al. | |
| 8,277,807 B2 | 10/2012 | Gallagher et al. | |
| 8,318,790 B2 | 11/2012 | Ying et al. | |
| 8,324,240 B2 | 12/2012 | Cai et al. | |
| 2006/0094682 A1 | 5/2006 | Westwick et al. | |
| 2007/0003555 A1 | 1/2007 | LeClair | |
| 2007/0191917 A1 | 8/2007 | Poulaki et al. | |
| 2007/0249540 A1 | 10/2007 | Papathanassiu | |
| 2008/0070930 A1 | 3/2008 | Huang et al. | |
| 2009/0076006 A1 | 3/2009 | Qian et al. | |
| 2009/0298818 A1 | 12/2009 | Lyons et al. | |
| 2010/0015126 A1 | 1/2010 | Gebbink et al. | |
| 2010/0022635 A1 | 1/2010 | Rajewski | |
| 2010/0048482 A1 | 2/2010 | Mochly-Rosen et al. | |
| 2010/0279311 A1 | 11/2010 | Kimura | |
| 2010/0292169 A1 | 11/2010 | Yao et al. | |
| 2010/0298280 A1 | 11/2010 | Kioschis-Schneider et al. | |
| 2011/0046155 A1* | 2/2011 | Frederickson | C07C 59/08 514/254.08 |
| 2011/0065734 A1 | 3/2011 | Bar et al. | |
| 2011/0118258 A1 | 5/2011 | Courtney et al. | |
| 2011/0160175 A1 | 6/2011 | Martin et al. | |
| 2011/0201587 A1 | 8/2011 | Shapiro | |
| 2011/0201643 A1 | 8/2011 | Maier et al. | |
| 2011/0218143 A1 | 9/2011 | Kaushal et al. | |
| 2011/0230444 A1 | 9/2011 | Garcia-Echeverria et al. | |
| 2011/0230551 A1 | 9/2011 | Gunatilaka et al. | |
| 2011/0237560 A1 | 9/2011 | Di Noia et al. | |
| 2011/0262449 A1 | 10/2011 | Petrilli et al. | |
| 2011/0281902 A1 | 11/2011 | Manley et al. | |
| 2012/0196815 A1 | 8/2012 | Timmermann et al. | |
| 2012/0252745 A1 | 10/2012 | Blagg et al. | |
| 2012/0309750 A1 | 12/2012 | Kang et al. | |

FOREIGN PATENT DOCUMENTS

| | | |
|---|---|---|
| WO | WO-2003/023001 | 3/2003 |
| WO | WO-2004/096212 A1 | 11/2004 |
| WO | WO-2006/020269 A2 | 2/2006 |
| WO | WO-2007/137237 A2 | 11/2007 |
| WO | WO-2009/010957 A2 | 1/2009 |
| WO | WO-2009/109616 A2 | 9/2009 |
| WO | WO-2009/114470 A2 | 9/2009 |
| WO | WO-2009/142618 A1 | 11/2009 |
| WO | WO-2010/015617 A1 | 2/2010 |
| WO | WO-2010/117425 A1 | 10/2010 |
| WO | WO-2011/083150 A2 | 7/2011 |
| WO | WO-2011/133659 A2 | 10/2011 |
| WO | WO-2012/106343 A2 | 8/2012 |
| WO | WO-2012/139010 A1 | 10/2012 |
| WO | WO-2013/015661 A2 | 1/2013 |

OTHER PUBLICATIONS

Calamia, et al., "Hsp90β Inhibition Modulates Nitric Oxide Production and Nitric Oxide-Induced Apoptosis in Human Chondrocytes", 2011, BMC Musculoskeletal Disorders 12: 989-995.

Imamura et al., "Involvement of Heat Shock Protein 90 in the Degradation of Mutant Insulin Receptors by the Proteasome", 1998, JBC 273 (18): 11183-11188.

Urban et al., "Heat Shock Response and Insulin-Associated Neurodegeneration", 2012, Trends in Pharmacological Sciences 33(3): 129-137.

Hirosumi et al., "A Central Role for JNK in Obesity and Insulin Resistance", 2002, Nature 420 (6913): 333-336.

Lee et al., "Biochemical and Biophysical Research Communications", on-line Dec. 19, 2012, Biochemical and Biophysical Research Communications 430(3): 1109-1113.

Neckers et al., "Hsp90 Molecular Chaperone Inhibitors: Are We There Yet?", 2012, Clinical Cancer Research 18 (1): 64-76.

Genbank Database, Accession No. DQ147989.1, dated Aug. 28, 2005.

Genbank Database, Accession No. AK146809.1, dated Oct. 6, 2010.

International Search Report for International Application No. PCT/US2013/042692, mailed Oct. 29, 2013.

International Search Report for International Application No. PCT/US2015/034750, mailed Jan. 12, 2016.

* cited by examiner

Annotation of Cytoscape Networks

◯ Node appears in both conditions.

● Node appears in both conditions.

———— Edge appears in Baseline and Crosstalk.

·········· Edge appears in Crosstalk.

-------- Edge appears in Baseline.

—⊣ Reverse directionality.
—▶ Same directionality.

Normoglycemia

Hyperglycemia

FIGURE 15-1

Homo sapiens heat shock 90kDa protein 1, alpha (HSPCA) gene, complete cds.

ACCESSION  DQ314871

VERSION    DQ314871.1  GI:83699648

```
   1 atgccccgt gttcgggcgg ggacggctcc acccctcctg ggccctccct tcgggacagg
  61 gactgtcccg cccagagtgc tgaataccog cgcgaccgtc tggatcccog cccaggaagc
 121 ccctctgaag cctcctcgcc gccgtttctg agaagcaggg cacctgttaa ctggtaccaa
 181 gaaaaggccc aagtgtttct ctggcatctg ttggtgtctg gatccaccac tctactctgt
 241 ctctgaaaac agcccttcca cgtctctgca ttccctgtca ctgcgtcact ggccttcaga
 301 cagagccaag gtgcagggca acacctctac aaggatctgc agccatttat attgcttagg
 361 ctactgatgc ctgaggaaac ccagacccaa gaccaaccga tgcaggagga ggaggttgag
 421 acgttcgcct ttcaggcaga aattgcccag ttgatgtcat tgatcatcaa tactttctac
 481 tcgaacaaag agatctttct gagagagctc atttcaaatt catcagatgc attggacaaa
 541 atccggtatg aaagcttgac agatccagt aaattagact ctgggaaaga gctgcatatt
 601 aaccttatac cgaacaaaca agatcgaact ctcactattg tggatactgg aattggaatg
 661 accaaggctg acttgatcaa taaccttggt actatcgcca gtctgggac caaagcgttc
 721 atggaagctt tgcaggctgg tgcagatatc tctatgattg gccagttcgg tgttggtttt
 781 tattctgctt atttggttgc tgagaaagta actgtgatca ccaaacataa cgatgatgag
 841 cagtacgctt gggagtcctc agcaggggga tcattcacag tgaggacaga cacaggtgaa
 901 cctatgggtc gtggaacaaa agttatccta cacctgaaag aagaccaaac tgagtacttg
 961 gaggaacgaa gaataaagga gattgtgaag aaacattctc agtttattgg atatcccatt
1021 actcttttg tggagaagga acgtgataaa gaagtaagcg atgatgagc tgaagaaaag
1081 gaagacaaag aagaagaaaa agaaaaagaa gagaaagagt cggaagacaa acctgaaatt
1141 gaagatgttg gttctgatga ggaagaagaa aagaaggatg gtgacaagaa gaagaagaag
1201 aagattaagg aaaagtacat cgatcaagaa gagctcaaca aaacaaagcc catctggacc
1261 agaaatcccg acgatattac taatgaggag tacggagaat tctataagag cttgaccaat
1321 gactgggaag atcacttggc agtgaagcat ttttcagttg aaggacagtt ggaattcaga
1381 gcccttctat ttgtcccacg acgtgctcct tttgatctgt ttgaaaacag aaagaaaaag
1441 aacaatatca aattgtatgt acgcagagtt ttcatcatgg ataactgtga ggagctaatc
1501 cctgaatatc tgaacttcat tagaggggtg gtagactcgg aggatctccc tctaaacata
1561 tcccgtgaga tgttgcaaca aagcaaaatt ttgaaagtta tcaggaagaa tttggtcaaa
1621 aaatgcttag aactctttac tgaactggcg gaagataaag agaactacaa gaaattctat
1681 gagcagttct ctaaaaacat aaagcttgga atacacgaag actctcaaaa tcggaagaag
1741 ctttcagagc tgttaaggta ctacacatct gcctctggtg atgagatggt ttctctcaag
1801 gactactgca ccagaatgaa ggagaaccag aaacatatct attatcac aggtgagacc
1861 aaggaccagg tagctaactc agcctttgtg gaacgtcttc ggaaacatgg cttagaagtg
1921 atctatatga ttgagcccat tgatgagtac tgtgtccaac agctgaagga atttgagggg
1981 aagactttag tgtcagtcac caaagaaggc ctggaactc cagaggatga agaagagaaa
2041 aagaagcagg aagagaaaaa aacaaagttt gagaacctct gcaaaatcat gaaagacata
2101 ttggagaaaa aagttgaaaa ggtggttgtg tcaaaccgat tggtgacatc tccatgctgt
2161 attgtcacaa gcacatatgg ctggacagca aacatggaga gaatcatgaa agctcaagcc
2221 ctaagagaca actcaacaat gggttacatg gcagcaaaga aacacctgga gataaaccct
2281 gaccattcca ttattgagac cttaaggcaa aaggcagagg ctgataagaa cgacaagtct
2341 gtgaaggatc tggtcatctt gctttatgaa actgcgctcc tgtcttctgg cttcagtctg
2401 gaagatcccc agacacatgc taacaggatc tacaggatga tcaaacttgg tctgggtatt
2461 gatgaagatg accctactgc tgatgatacc agtgctgctg taactgaaga aatgccaccc
2521 cttgaaggag atgacgacac atcacgcatg gaagaagtag actaa (SEQ ID NO: 7)
```

FIGURE 15-2 (continued)

TRANSLATION

DEFINITION heat shock 90kDa protein 1, alpha [Homo sapiens].
ACCESSION ABC40730
VERSION ABC40730.1 GI:83699649

```
  1 mppcsggdqs tppqpslrdr dcpaqsaeyp rdrldprpqs pseassppfl rsrapvnwyq
 61 ekaqvflwhl lvsgsttllc lwkqpfhvsa fpvtaslafr qsqgagqhly kdlqpfillr
121 llmpeetqtq dqpmeeeeve tfafqaeiaq lmsliintfy snkeiflrel isnssdaldk
181 iryesltdps kldsgkelhi nlipnkgdrt itivdtgigm tkadlinnlg tiaksgtkaf
241 mealqagadi smigqfgvgf ysaylvaekv tvitkhndde qyawessagg sftvrtdtge
301 pmgrgtkvil hlkedqteyl eerrikeivk khsqfigypi tlfvekerdk evsddeaeek
361 edkeeekeke ekesedkpei edvgsdeeee kkdgdkkkkk kikekyidqe elnktkpiwt
421 rnpdditnee yqefyksltn dwedhlavkh fsveqqlefr allfvprrap fdlfenrkkk
481 nniklyvrrv fimdnceeli peylnfirgv vdsedlplni sremiqqski lkvirknlvk
541 kclelftela edkenykkfy eqfskniklg ihedsqnrkk lsellryyts asgdemvslk
601 dyctrmkenq khiyyitqet kdqvansafv erlrkhglev iymiepidey cvqqlkefeq
661 ktlvsvtkeg lelpedeeek kkqeekktkf enlckimkdi lekkvekvvv snrivtspcc
721 ivtstygwta nmerimkaqa lrdnstmgym aakkhleinp dhsiietlrq kaeadkndks
781 vkdlviliye tallssgfsl edpqthanri yrmiklglgi deddptaddt saavteempp
841 legdddtsrm eevd (SEQ ID NO: 8)
```

FIGURE 16-1
Homo sapiens heat shock protein 90kDa alpha (cytosolic), class B member 1 (HSP90AB1), mRNA
ACCESSION   NM_007355 XR_108652 XR_112882 XR_113895
VERSION   NM_007355.2 GI:20149593

```
   1 ctccggcgca gtgttgggac tgtctgggta tcggaaagca agcctacgtt gctcactatt
  61 acgtataatc cttttctttt caagatgcct gaggaagtgc accatgcaga ggaggaggtg
 121 gagacttttg cctttcaggc agaaattgcc caactcatgt ccctcatcat caatacccts
 181 tattccaaca aggagatttt ccttcgggag ttgatctcta atgcttctga tgccttggac
 241 aagattcgct atgagagcct gacagaccct tcgaagttgg acagtggtaa agagctgaaa
 301 attgacatca tcccaaccc tcaggaacgt accctgactt tggtagacac aggcattggc
 361 atgaccaaag ctgatctcat aaataatttg ggaaccattg ccaagtctgg tactaaagca
 421 ttcatggagg ctcttcaggc tggtgcagac atctccatga ttgggcagtt tggtgttggc
 481 ttttattctg cctacttggt ggcagagaaa gtggttgtga tcacaaagca caacgatgat
 541 gaacagtatg cttgggagtc ttctgctgga ggttccttca ctgtgcgtgc tgaccatggt
 601 gagcccattg cagggggtac caaagtgatc ctccatctta aagaagatca gacagagtac
 661 ctagaagaga gcgcggtcaa agaagtagtg aagaagcatt ctcagttcat aggctatccc
 721 atcacccttt atttggagaa ggaacgagag aaggaaatta gtgatgatga ggcagaggaa
 781 gagaaagtg agaaagaga ggaacagtaa gatgatgaag aaaaacccaa gatcgaagat
 841 gtgggttcag atgaggagga tgacagcggt aaggataaga agaagaaaac taagaagatc
 901 aaagagaaat acattgatca ggaagaacta aacaagacca agcctatttg gaccagaaac
 961 cctgatgaca tcacccaaga ggagtatgga gaattctaca agagcctcac taatgactgg
1021 gaagaccact ggcagtcaa gcacttttct gtagaaggtc agttggaatt cagggcattg
1081 ctatttattc ctcgtcgggc tcccttgac cttttgaga acaagaagaa aaagaacaac
1141 atcaaactct atgtccgccg tgtgttcatc atggacagct gtgatgagtt gataccagag
1201 tatctcaatt ttatccgtgg tgtggttgac tctgaggatc tgcccctgaa catctcccga
1261 gaaatgctcc agcagagcaa aatcttgaaa gtcattcgca tcatgaagga aaacattgt taagaagtgc
1321 cttgagctct tctctgagct ggcagaagac aaggagaatt acaagaaatt ctatgaggca
1381 ttctctaaaa atctcaagct tggaatccac gaagactcca ctaaccgccg ccgcctgtct
1441 gagctgctgc gctatcatac ctcccagtct ggagatgaga tgacatctct gtcagagtat
1501 gtttctcgca tgaaggagac acagaagtcc atctattaca tcactgttga gagcaaagag
1561 caggtggcca actcagcttt tgtggagcga gtgcggaaac ggggcttcga ggtggtatat
1621 atgaccgagc ccattgacga gtactgtgtg cagcagctca aggaatttga tgggaagagc
1681 ctggtctcag ttaccaagga gggtctggag ctgcctgagg atgaggagga gaagaagaag
1741 atggaagagc gcaaggcaaa gtttgagaac ctctgcaagc tcatgaaaga aatcttagat
1801 aagaaggttg agaaggtgac aatctccaat agacttgtgt cttcaccttg ctgcattgtg
1861 accagcacct acggctggac agccaatatg gagcggatca tgaaagccca ggcacttcgg
1921 gacaactcca ccatgggcta tatgatggcc aaaaagcacc tggagatcaa ccctgaccac
1981 cccattgtgg agacgctgcg gcagaaggct gaggccgaca gaatgataa ggcagttaag
2041 gacctggtgg tgctgctgtt tgaaaccgcc ctgctatctt ctggcttttc ccttgaggat
2101 cccagaccc actccaaccg catctatcgc atgatcaagc taggtctagg tattgatgaa
2161 gatgaagtgg cagcagagga acccaatgct gcagttcctg atgagatccc ccctctcgag
2221 ggcgatgagg atgcgctccg catggaagaa gtcgattagg ttaggagttc atagttggaa
2281 aacttgtgcc cttgtatagt gtccccatgg gctcccactg cagcctcgag tgccctgtc
2341 ccactggct cccctgctg gtgtctagtg ttttttcccc tctcctgtcc ttgtgttgaa
2401 ggcagtaaac taagggtgtc aagcccatt ccctctctac tcttgacagc aggattggat
2461 gttgtgtatt gtggtttatt ttattttctt catttgttc tgaaattaaa gtatgcaaaa
2521 taaagaatat gccgttttaa aaaaaaaaaa aaaaaaaaaa aaaaaaa (SEQ ID NO: 9)
```

FIGURE 16-2 (continued)

TRANSLATION

```
  1 mpeevhhgee evetfafqae iaqlmsliin tfysnkeifl relisnasda ldkiryeslt
 61 dpskldsgke lkidiipnpq ertltlvdtg igmtkadlin nigtiaksgt kafmealqag
121 adismiqqfg vqfysaylva ekvvvitkhn ddeqyawess aggsftvrad hgepigrgtk
181 vilhlkedqt eyleerrvke vvkkhsqfig ypitlyleke rekeisddea eeekgekeee
241 dkddeekpki edvgsdeedd sqkdkkkktk kikekyidqe einktkpiwt rnpdditqee
301 ygefyksltn dwedhlavkh fsvegqlefr allfiprrap fdlfenkkkk nniklyvrrv
361 fimdscdeli peylnfirgv vdsedlplni sremlqqski lkvirknivk kclelfsela
421 edkenykkfy eafsknlklg ihedstnrrr lsellryhts qsgdemtsls eyvsrmketq
481 ksiyyitges keqvansafv ervrkrgfev vymtepidey cvqqikefdg kslvsvtkeg
541 lelpedeeek kkmeeskakf enlcklmkei ldkkvekvti snrlvsspcc ivtstygwta
601 nmerimkaqa lrdnstmgym makkhleinp dhpivetlrq kaeadkndka vkdlvvlife
661 tallssqfsl edpqthsnri yrmiklglgi dedevaaeep naavpdeipp legdedasrm
721 eevd (SEQ ID NO: 10)
```

FIG. 17

Nucleic acid sequence alignment

```
HSP90-alpha  ATGCCCCCGTGTTCGGGCGGGGACGGCTCCACCCCTCCTGGGCCCTCCCTTCGGGACAGG  60
HSP90-beta   ---------------------------------------------CTCCGG------    6

HSP90-alpha  GACTGTCCCGCCCAGAGTGCTGAATACCCGCGCGACCGTCTGGATCCCCGCCCAGGAAGC  120
HSP90-beta   --------CGC----AGTGTTGG----------GACTGTCTGGGTATC-----GGAAAGC   39
                     ***    **** **          *** ****** *  *     * ****

HSP90-alpha  CCCTCTGAAGCCTCCTCGCCCCCGTTTCTGAGAAGCAGGGCACCTCTTAACTGGTACCAA  180
HSP90-beta   -------AAGCCTAC--------GTT----------------------------------   50
                    ****** *        ***

HSP90-alpha  GAAAAGGCCCAAGTGTTTCTCTGGCATCTGTTGGTGTCTGGATCCACCACTCTACTCTGT  240
HSP90-beta   ------GCTCA---------------------------------CTATTACGT         64
                   ** **                                   *** *   **

HSP90-alpha  CTCTGGAAACAGCCCTTCCACGTCTCTGCATTCCCTGTCACTGCGTCACTGGCCTTCAGA  300
HSP90-beta   --------ATAATCCTTTT-----------------------------------------   75
                     *  *   ****

HSP90-alpha  CAGAGCCAAGGTGCAGGGCAACACCTCTACAAGGATCTGCAGCCATTTATATTGCTTAGG  360
HSP90-beta   ----------------------CTTTTCAAG-----------------------------   84
                                   ** * ****

HSP90-alpha  CTACTGATGCCTGACGAAACCCAGACCCAAGACCAACCGATGGACCACCAGGAGGTTGAG  420
HSP90-beta   ------ATGCCTGAGGAAGTGCA--------------CCATGGAG-AGGAGGAGGTGGAG  123
                   *********** **  **              *  ***** ********** ***

HSP90-alpha  ACGTTCGCCTTTCAGGCAGAAAATTGCCCAGTTGATGTCATTGATCATCAATACTTTCTAC  480
HSP90-beta   ACTTTTGCCTTTCAGGCAGAAAATTGCCCAACTCATGTCCCTCATCATCAATACCTTCTAT  183
             ** **  ********************** * ***** * *  ********* *****

HSP90-alpha  TCGAACAAAGAGATCTTTCTGAGAGAGCTCATTTCAAATTCATCAGATGCATTGGACAAA  540
HSP90-beta   TCCAACAAGGAGATTTTTCCTTCGGGAGTTGATCTCTAATGCTTCTCATGCCTTGGACAAG  243
             ** ***** ***** ****  ** ** * *** *  ***  ** *** ** *****

HSP90-alpha  ATCCGGTATGAAAGCTTGACACACATCCCAGTAAATTAGACTCTGGGCAAAGAGCTGCATATT  600
HSP90-beta   ATTCGCTATGAGACCCCTCACACACCCTTCGAAGTTGGACAGTGGTAAAGAGCTGAAATT  303
             ** ** ***** ***  *******  ** ** ***  *** ********* *  ***

HSP90-alpha  AACCTTATACCGAACAAACAAGATCGAACTCTCACTATTGTGGATACTGGAATTGGAATG  660
HSP90-beta   GACATCATCCCCAACCCTCAGGAACGTACCCTGACTTTGGTAGACACAGGCATTGGCATG  363
             ** * ** ** ***    ** ** ** **  ** ** ** ** ** ** ***** ***

HSP90-alpha  ACCAAGGCTGACTTGATCAATAACCTTGGTACTATCGCCAAGTCTGGGACCAAAGCGTTC  720
HSP90-beta   ACCAAAGCTGATCTCATAAATAATTTGGGAACCATTGCCAAGTCTGGTACTAAAGCATTC  423
             ***** ***** * ** ***** * ** ** ** ********** ** ***** ***

HSP90-alpha  ATGGAAGCTTTGCACGCTCGTCCAGATATCTCTATGATTGGCCACTTCCTGTTGGTTTT  780
HSP90-beta   ATGGAGGCTCTTCACGCTCGTCCAGACATCTCCATGATTGGCCACTTTCTGTTGGCTTT  483
             ***** ***  * ************* ***** ************** ****** ***

HSP90-alpha  TATTCTGCTTATTTGGTTGCTGAGAAAGTAACTGTGATCACCAAACATAACGATGATGAG  840
HSP90-beta   TATTCTGCCTACTTGGTGGCAGAGAAAGTGGTTGTGATCACAAAGCACAACGATGATGAA  543
             ********  ** **** ** ******** * ******** ** ** ***********
```

FIG. 17 (continued)

```
HSP90-alpha   CAGTACGCTTGGGAGTCCTCAGCAGGGGGATCATTCACAGTGAGGACAGACACAGGTGAA  900
HSP90-beta    CAGTATGCTTGGGAGTCTTCTGCTGGAGGTTCCTTCACTGTGCGTGCTGACCATGGTGAG  603
              ***** ************ ** ** ** ** ** ***** *** *  *  ***   *****

HSP90-alpha   CCTATGGGTCGTGGAACAAAAGTTATCCTACACCTGAAGAAGACCAAACTGAGTACTTG   960
HSP90-beta    CCCATTGGCAGGGGTACCAAAGTGATCCTCCATCTTAAAGAAGATCAGACAGAGTACCTA  663
              ** ** **  * ** ** ***** ***** ** ** ******** ** ** ****** *

HSP90-alpha   GAGGAACGAAGAATAAAGGAGATTGTGAAGAAACATTCTCAGTTTATTGGATATCCCATT 1020
HSP90-beta    GAAGAGAGGCGGGTCAAAGAAGTAGTGAAGAAGCATTCTCAGTTCATAGGCTATCCCATC  723
              ** **    *    * ** ** ** ******* *********** ** ** ********

HSP90-alpha   ACTCTTTTTGTGGAGAAGGAACGTGATAAAGAAGTAAGCGATGATGAGGCTGAAGAAAAG 1080
HSP90-beta    ACCCTTTATTTGGAGAAGGAACGAGAGAAGGAAATTAGTGATGATGAGGCAGAGGAAGAG  783
              ** **** *  ** ************ **  ** ** *  ** ********** ** ** **

HSP90-alpha   GAAGACAAAGAAGAAGAAAAAGAAAAAGAAGAGAAAGAGTCGGAAGACAAACCTGAAATT 1140
HSP90-beta    AAAGGTGAGAAAGAAGAGGAAGATAAAGATGA---------TGAAGAAAAACCCAAGATC  834
              *** *   * ******  **** *****  **          ****  ***** *  **

HSP90-alpha   GAAGATGTTGGTTCTGATGAGGAAGAAGAAAAAGAAGGATGGTGACAAGAAGAAGAAGAAG 1200
HSP90-beta    GAAGATGTGGGTTCAGATGAGGAGGATGACAGCGGTAAGGATAAGAAGAAGAAAACTAAG   894
              ********  ***** ********  * **    ** *  * *  ********* *  ***

HSP90-alpha   AAGATTAAGGAAAAGTACATCGATCAAGAAGAGCTCAACAAAACAAAGCCCATCTGGACC 1260
HSP90-beta    AAGATCAAAGAGAAATACATTGATCAGGAAGAACTAAACAAGACCAAGCCTATTTGGACC  954
              ***** ** ** ** ***** ***** ***** ** ***** ** ***** ** ******

HSP90-alpha   AGAAATCCCGACGATATTACTAATGAGGAGTACGGAGAATTCTATAAGAGCTTGACCAAT 1320
HSP90-beta    AGAAACCCTGATGACATCACCCAAGAGGAGTATGGAGAATTCTACAAGAGCCTCACTAAT 1014
              ***** ** ** ** ** **  * ** ******* ********** ******  * ** ***

HSP90-alpha   GACTGGGAAGATCACTTGGCAGTGAAGCATTTTTCAGTTGAAGGACAGTTGGAATTCAGA 1380
HSP90-beta    GACTGGGAAGACCACTTGGCAGTCAAGCACTTTTCTGTAGAAGGTCAGTTGGAATTCAGG 1074
              ***********  ********** ***** ***** **  ***** **************

HSP90-alpha   GCCCTTCTATTTGTCCCACGACGTGCTCCTTTTGATCTGTTTGAAAACAGAAAGAAAAAG 1440
HSP90-beta    GCATTGCTATTTATTCCTCGTCGGGCTCCCTTTGACCTTTTTGAGAACAAGAAGAAAAAG 1134
              **  * ****** *  ** ** ** **  ** ***** *  ** *** ****** *********

HSP90-alpha   AACAATATCAAATTGTATGTACGCAGAGTTTTCATCATGGATAACTGTGAGGAGCTAATC 1500
HSP90-beta    AACAACATCAAACTCTATGTCCGCCGTGTGTTCATCATGGACAGCTGTGATGAGTTGATA 1194
              ***** ****** *  ***** ***  * ** ********** *  ****** ***   * **

HSP90-alpha   CCTGAATATCTGAACTTCATTAGAGGGGTGGTAGACTCGGAGGATCTCCCTCTAAACATA 1560
HSP90-beta    CCAGAGTATCTCAATTTTATCCGTGGTGTGGTTGACTCTGAGGATCTGCCCCTGAACATC 1254
              ** ** ***** ** ** ** ** *  *****  ***** ******* ** ** ******

HSP90-alpha   TCCCGTGAGATGTTGCAACAAAGCAAAATTTTGAAAGTTATCAGGAAGAATTTGGTCAAA 1620
HSP90-beta    TCCCGAGAAATGCTCCAGCAGAGCAAAATCTTGAAAGTCATTCGCAAAAACATTGTTAAG 1314
              ***** ** *** * ** ** ******** ******* ** *   **  *   * ** **

HSP90-alpha   AAATGCTTAGAACTCTTTACTGAACTGGCGGAAGATAAAGAGAACTACAAGAAATTCTAT 1680
HSP90-beta    AAGTGCCTTGAGCTCTTCTCTGAGCTGGCAGAAGACAAGGAGAATTACAAGAAATTCTAT 1374
              ** *** * ** ***** * *** ***** ***** ** ***** ***************

HSP90-alpha   GAGCAGTTCTCTAAAAACATAAAGCTTGGAATACACGAAGACTCTCAAAATCGGAAGAAG 1740
HSP90-beta    GAGGCATTCTCTAAAAATCTCAAGCTTGGAATCCACGAAGACTCCACTAACCGCCGCCGC 1434
              ***   ********** *  ********** **********  *  ** ** *  **
```

FIG. 17 (continued)

```
HSP90-alpha   CTTTCAGAGCTGTTAAGGTACTACACATCTGCCTCTGGTGATGAGATGGTTTCTCTCAAG 1800
HSP90-beta    CTGTCTGAGCTGCTGCGCTATCATACCTCCCAGTCTGGAGATGAGATGACATCTCTGTCA 1494
              ** ** ****** *  * **  * ** **    ***** ********    *****

HSP90-alpha   GACTACTGCACCAGAATGAAGGAGAACCAGAAACATATCTATTATATCACAGGTGAGACC 1860
HSP90-beta    GAGTATGTTTCTCGCATGAAGGAGACACAGAAGTCCATCTATTACATCACTGGTGAGAGC 1554
              ** **     *  *  ** **********  *****   ******* ***** ******* *

HSP90-alpha   AAGGACCAGGTAGCTAACTCAGCCTTTGTGGAACGTCTTCGGAAACATGGCTTAGAAGTG 1920
HSP90-beta    AAAGAGCAGGTGGCCAACTCAGCTTTTGTGGAGCGAGTGCGGAAACGGGGCTTCGAGGTG 1614
              ** ** ***** ** ******* ** *******  **    ****** *****  ** ***

HSP90-alpha   ATCTATATGATTGAGCCCATTGATGAGTACTGTGTCCAACAGCTGAAGGAATTTGAGGGG 1980
HSP90-beta    GTATATATGACCGAGCCCATTGACGAGTACTGTGTGCAGCAGCTCAAGGAATTTGATGGG 1674
               * *******    ********** **********  ** ***** ********** ***

HSP90-alpha   AAGACTTTAGTGTCAGTCACCAAAGAAGGCCTGGAACTTCCAGAGGATGAAGAAGAGAAA 2040
HSP90-beta    AAGAGCCTGGTCTCAGTTACCAAGGAGGGTCTGGAGCTGCCTGAGGATGAGGAGGAGAAG 1734
              ****    * ** ***** *****  ** ** ***** ** ** ********  ** *****

HSP90-alpha   AAGAAGCAGGAAGAGAAAAAAACAAAGTTTGAGAACCTCTGCAAAAATCATGAAAGACATA 2100
HSP90-beta    AAGAAGATGGAAGAGAGCAAGGCAAAGTTTGAGAACCTCTGCAAGCTCATGAAAGAAATC 1794
              ******  ********  **  ***********************   **********  **

HSP90-alpha   TTGGAGAAAAAAGTTGAAAAGGTGGTTGTGTCAAACCGATTGGTGACATCTCCATGCTGT 2160
HSP90-beta    TTAGATAAGAAGGTTGAGAAGGTGACAATCTCCAATAGACTTGTGTCTTCACCTTGCTGC 1854
              ** ** ** ** ***** ******      *  *** ** *  ***** * ** ** *****

HSP90-alpha   ATTGTCACAAGCACATATGGCTGGACAGCAAACATGGAGAGAATCATGAAAGCTCAAGCC 2220
HSP90-beta    ATTGTGACCAGCACCTACGGCTGGACAGCCAATATGGAGCGGATCATGAAAGCCCAGGCA 1914
              ***** ** ***** ** *********** ** *******  * ********* ** **

HSP90-alpha   CTAAGAGACAACTCAACAATGGGTTACATGGCAGCAAAGAAACACCTGGAGATAAACCCT 2280
HSP90-beta    CTTCGGGACAACTCCACCATGGGCTATATGATGGCCAAAAAGCACCTGGAGATCAACCCT 1974
              **  * ******** **  *****  ** *** *  ** ** ********** ******

HSP90-alpha   GACCATTCCATTATTGAGACCTTAAGGCAAAAGGCAGAGGCTGATAAGAACGACAAGTCT 2340
HSP90-beta    GACCACCCCATTGTGGAGACGCTGCGGCAGAAGGCTGAGGCCGACAAGAATGATAAGGCA 2034
              *****  ***** * ******  *   ****** ***** ***** ** ** *** * *

HSP90-alpha   GTGAAGGATCTGGTCATCTTGCTTTATGAAACTGCGCTCCTGTCTTCTGGCTTCAGTCTG 2400
HSP90-beta    GTTAAGGACCTGGTGGTGCTGCTGTTTGAAACCGCCCTGCTATCTTCTGGCTTTTCCCTT 2094
              ** ***** ***** *  ****  ******* ** **  * **********    **

HSP90-alpha   GAAGATCCCCAGACACATGCTAACAGGATCTACAGGATGATCAAACTTGGTCTGGGTATT 2460
HSP90-beta    GAGGATCCCCAGACCCACTCCAACCGCATCTATCGCATGATCAAGCTAGGTCTAGGTATT 2154
              ** *********** **  * *** * ***** * ***********  ** ***** ******

HSP90-alpha   GATGAAGATGACCCTACTGCTGATGATACCAGTGCTGCTGTAACTGAAGAAATGCCACCC 2520
HSP90-beta    GATGAAGATGAAGTGGCAGCAGAGGAACCCAATGCTGCAGTTCCTGATGAGATCCCCCCT 2214
              **********    *  ** **  * ***  * ****** **  ***** ** ** ** **

HSP90-alpha   CTTGAAGGAGATGACGACACATCACGCATGGAAGAAGTAGACTAA--------------- 2565
HSP90-beta    CTCGAGGGCGATGAGGATGCGTCTCGCATGGAAGAAGTCGATTAGGTTAGGAGTTCATAG 2274
              ** ** ** ***** **  * ** ************* ** **

HSP90-alpha   ------------------------------------------------------------
HSP90-beta    TTGGAAAACTTGTGCCCTTGTATAGTGTCCCCATGGGCTCCCACTGCAGCCTCGAGTGCC 2334
```

FIG. 17 (continued)

```
HSP90-alpha    ----------------------------------------------------------------
HSP90-beta     CCTGTCCCACCTGGCTCCCCCTGCTGGTGTCTAGTGTTTTTTTCCCTCTCCTGTCCTTGT 2394

HSP90-alpha    ----------------------------------------------------------------
HSP90-beta     GTTGAAGGCAGTAAACTAAGGGTGTCAAGCCCCATTCCCTCTCTACTCTTGACAGCAGGA 2454

HSP90-alpha    ----------------------------------------------------------------
HSP90-beta     TTGGATGTTGTGTATTGTGGTTTATTTTATTTTCTTCATTTTGTTCTGAAATTAAAGTAT 2514

HSP90-alpha    ------------------------------------------------------
                                                          (SEQ ID NO: 7)

HSP90-beta     GCAAAATAAAGAATATGCCGTTTTAAAAAAAAAAAAAAAAAAAAAAAAAAA 2567
                                                          (SEQ ID NO: 9)
```

FIG. 17 (continued)

Amino acid sequence alignment

```
HSP90-alpha    MPPCSGGDGSTPPGPSLRDRDCPAQSAEYPRDRLDPRPGSPSEASSPPFLRSRAPVNWYQ  60
HSP90-beta     ------------------------------------------------------------

HSP90-alpha    EKAQVFLWHLLVSGSTTLLCLWKQPFHVSAFPVTASLAFRQSCGAGQHLYKDLQPFILLR  120
HSP90-beta     ------------------------------------------------------------

HSP90-alpha    LLMPEETQTQDQPMEEEEVETFAFQAEIAQLMSLIINTFYSNKEIFLRELISNSSDALDK  180
HSP90-beta     --MPEEVHHG-----EEEVETFAFQAEIAQLMSLIINTFYSNKEIFLRELISNASDALDK   53
                 ****  :        **********************************:*******

HSP90-alpha    IRYESLTDPSKLDSGKELHINLIPNKQDRTLTIVDTGIGMTKADLINNLGTIAKSGTKAF  240
HSP90-beta     IRYESLTDPSKLDSGKELKIDIIPNPQERTLTLVDTGIGMTKADLINNLGTIAKSGTKAF  113
               ******************::::***:*:****:***************************

HSP90-alpha    MEALQAGADISMIGQFGVGFYSAYLVAEKVTVITKHNDDEQYAWESSAGGSFTVRTDTGE  300
HSP90-beta     MEALQAGADISMIGQFGVGFYSAYLVAEKVVVITKHNDDEQYAWESSAGGSFTVRADHGE  173
               *****************************.*********************** * **

HSP90-alpha    PMGRGTKVILHLKEDQTEYLEERRIKEIVKKHSQFIGYPITLFVEKERDKEVSDDEAEEK  360
HSP90-beta     PIGRGTKVILHLKEDQTEYLEERRVKEVVKKHSQFIGYPITLYLEKEREKEISDDEAEEE  233
               *:**********************:**:**************::*****:*:*******:

HSP90-alpha    EDKEEEKEKEEKESEDKPEIEDVGSDEEEEKKDGDKKKKKKIKEKYIDQEELNKTKPIWT  420
HSP90-beta     KG---EKEEEDKDDEEKPKIEDVGSDEEDDSGKDKKKKTKKIKEKYIDQEELNKTKPIWT  290
               :    *** *:* :*****************   ***.**********************

HSP90-alpha    RNPDDITNEEYGEFYKSLTNDWEDHLAVKHFSVEGQLEFRALLFVPRRAPFDLFENRKKK  480
HSP90-beta     RNPDDITQEEYGEFYKSLTNDWEDHLAVKHFSVEGQLEFRALLFIPRRAPFDLFENKKKK  350
               *******:************************************:***********:***

HSP90-alpha    NNIKLYVRRVFIMDNCEELIPEYLNFIRGVVDSEDLPLNISREMLQQSKILKVIRKNLVK  540
HSP90-beta     NNIKLYVRRVFIMDSCDELIPEYLNFIRGVVDSEDLPLNISREMLQQSKILKVIRKNIVK  410
               **************.*:****************************************:**

HSP90-alpha    KCLELFTELAEDKENYKKFYEQFSKNIKLGIHEDSQNRKKLSELLRYYTSASGDEMVSLK  600
HSP90-beta     KCLELFSELAEDKENYKKFYEAFSKNLKLGIHEDSTNRRRLSELLRYHTSQSGDEMTSLS  470
               ******:**************:****:********.**::*******:** *****.**:

HSP90-alpha    DYCTRMKENQKHIYYITGETKDQVANSAFVERLRKHGLEVIYMIEPIDEYCVQQLKEFEG  660
HSP90-beta     EYVSRMKETQKSIYYITGESKEQVANSAFVERVRKRGFEVVYMTEPIDEYCVQQLKEFDG  530
               :*  ****.**.:******:*:********::**:*:**:**:**************:*

HSP90-alpha    KTLVSVTKEGLELPEDEEEKKKQEEKKTKFENLCKIMKDILEKKVEKVVVSNRLVTSPCC  720
HSP90-beta     KSLVSVTKEGLELPEDEEEKKKMEESKAKFENLCKLMKEILDKKVEKVTISNRLVSSPCC  590
               *:********************* ** *:******:**:**:****** :*****:****

HSP90-alpha    IVTSTYGWTANMERIMKAQALRDNSTMGYMAAKKHLEINPDHSIIETLRQKAEADKNDKS  780
HSP90-beta     IVTSTYGWTANMERIMKAQALRDNSTMGYMMAKKHLEINPDHPIVETLRQKAEADKNDKA  650
               ***************************** ***********.*:**************:

HSP90-alpha    VKDLVILLYETALLSSGFSLEDPQTHANRIYRMIKLGLGIDEDDPTADDTSAAVTEEMPP  840
HSP90-beta     VKDLVVLLFETALLSSGFSLEDPQTHSNRIYRMIKLGLGIDEDEVAAEEPNAAVPDEIPP  710
               *****:**:*****************:***************:  *:: *** :*:.**

HSP90-alpha    LEGDDDTSRMEEVD 854 (SEQ ID NO: 8)
HSP90-beta     LEGDEDASRMEEVD 724 (SEQ ID NO: 10)
               ****:*:*******
```

METHODS OF TREATING A METABOLIC SYNDROME BY MODULATING HEAT SHOCK PROTEIN (HSP) 90-β

PRIORITY INFORMATION

This application claims priority to U.S. Provisional Application No. 61/652,023, filed on May 25, 2012, the entire contents of which is incorporated herein by reference.

SEQUENCE LISTING

The instant application contains a Sequence Listing which has been submitted in ASCII format via EFS-Web and is hereby incorporated by reference in its entirety. Said ASCII copy, created on May 14, 2013, is named 119992-06402_SL.txt and is 22,186 bytes in size.

BACKGROUND

As the levels of blood glucose rise postprandially, insulin is secreted and stimulates cells of the peripheral tissues (skeletal muscles and fat) to actively take up glucose from the blood as a source of energy. Loss of glucose homeostasis as a result of dysregulated insulin secretion or action typically results in metabolic disorders such as diabetes, which may be co-triggered or further exacerbated by obesity. Because these conditions are often fatal, strategies to restore adequate glucose clearance from the bloodstream are required.

Although diabetes may arise secondary to any condition that causes extensive damage to the pancreas (e.g., pancreatitis, tumors, administration of certain drugs such as corticosteroids or pentamidine, iron overload (i.e., hemochromatosis), acquired or genetic endocrinopathies, and surgical excision), the most common forms of diabetes typically arise from primary disorders of the insulin signaling system. There are two major types of diabetes, namely type 1 diabetes (also known as insulin dependent diabetes (IDDM)) and type 2 diabetes (also known as insulin independent or non-insulin dependent diabetes (NIDDM)), which share common long-term complications in spite of their different pathogenic mechanisms.

Type 1 diabetes, which accounts for approximately 10% of all cases of primary diabetes, is an organ-specific autoimmune disease characterized by the extensive destruction of the insulin-producing beta cells of the pancreas. The consequent reduction in insulin production inevitably leads to the deregulation of glucose metabolism. While the administration of insulin provides significant benefits to patients suffering from this condition, the short serum half-life of insulin is a major impediment to the maintenance of normoglycemia. An alternative treatment is islet transplantation, but this strategy has been associated with limited success.

Type 2 diabetes, which affects a larger proportion of the population, is characterized by a deregulation in the secretion of insulin and/or a decreased response of peripheral tissues to insulin, i.e., insulin resistance. While the pathogenesis of type 2 diabetes remains unclear, epidemiologic studies suggest that this form of diabetes results from a collection of multiple genetic defects or polymorphisms, each contributing its own predisposing risks and modified by environmental factors, including excess weight, diet, inactivity, drugs, and excess alcohol consumption. Although various therapeutic treatments are available for the management of type 2 diabetes, they are associated with various debilitating side effects. Accordingly, patients diagnosed with or at risk of having type 2 diabetes are often advised to adopt a healthier lifestyle, including loss of weight, change in diet, exercise, and moderate alcohol intake. Such lifestyle changes, however, are not sufficient to reverse the vascular and organ damages caused by diabetes.

SUMMARY OF THE INVENTION

In one aspect, the invention provides a method of treating a metabolic syndrome in a subject, comprising administering to the subject an HSP90 modulator, thereby treating the metabolic syndrome in the subject.

In one embodiment, the HSP90 modulator is an HSP90 inhibitor.

In one embodiment, the HSP90 inhibitor is an inhibitor of HSP90β.

In one embodiment, the HSP90 inhibitor is a specific inhibitor of HSP90β.

In one embodiment, the HSP90 inhibitor is an inhibitor of HSP90α.

In one embodiment, the metabolic syndrome comprises type 2 diabetes.

In one embodiment, the metabolic syndrome comprises type 1 diabetes.

In one embodiment, the metabolic syndrome comprises insulin resistance.

In one embodiment, the metabolic syndrome comprises insulin insufficiency.

In one embodiment, the metabolic syndrome comprises obesity.

In one embodiment, the metabolic syndrome comprises hyperinsulinemia.

In one embodiment, the metabolic syndrome comprises impaired glucose tolerance (IGT).

In one embodiment, a subject with metabolic syndrome exhibits three or more of the following signs:
a) Blood pressure equal to or higher than 130/85 mmHg;
b) Fasting blood glucose equal to or higher than 100 mg/dL;
c) Large waist circumference wherein a large waist circumference is 40 inches or more for men and 35 inches or more for women;
d) Low HDL cholesterol wherein low LDH cholesterol is under 40 mg/dL for men and under 50 mg/dL; and
e) Triglycerides equal to or higher than 150 mg/dL.

In one embodiment, the HSP90 inhibitor comprises a nucleic acid inhibitor. In one embodiment, the nucleic acid inhibitor comprises an antisense nucleic acid molecule. In one embodiment, the nucleic acid inhibitor comprises a double stranded nucleic acid molecule. In one embodiment, the nucleic acid inhibitor comprises a double stranded RNA selected from the group consisting of an siRNA, a shRNA, and a dicer substrate siRNA (DsiRNA).

In one embodiment, the HSP90 inhibitor comprises an antibody.

In one embodiment, the HSP90 inhibitor comprises a small molecule. In one embodiment, the small molecule is selected from the group consisting of lonidamine or an analog thereof, celastrol or analog thereof, gedunin or an analog thereof, and coumermycin or an analog thereof.

In one embodiment, treating the metabolic syndrome comprises normalizing a blood glucose level in a subject.

In one embodiment, treating the metabolic syndrome comprises normalizing an Hb1Ac level in a subject.

In one embodiment, treating the metabolic syndrome comprises prevention of at least one complication of diabetes associated with poor circulation.

In one embodiment, treating the metabolic syndrome comprises amelioration of at least one sign or symptom of type 2 diabetes.

In one embodiment, treating the metabolic syndrome comprises amelioration of at least one sign or symptom of type 1 diabetes.

In one embodiment, treating the metabolic syndrome comprises amelioration of at least one sign or symptom of insulin resistance.

In one embodiment, treating the metabolic syndrome comprises amelioration of at least one sign or symptom of insulin insufficiency.

In one embodiment, treating the metabolic syndrome comprises amelioration of at least one sign or symptom of hyperinsulinemia.

In one embodiment, treating the metabolic syndrome comprises amelioration of at least one sign or symptom of impaired glucose tolerance (IGT).

In one embodiment, treating the metabolic syndrome comprises amelioration of at least one sign or symptom of obesity.

In one embodiment, treating the metabolic syndrome comprises amelioration of at least one of
  a) Blood pressure equal to or higher than 130/85 mmHg;
  b) Fasting blood glucose equal to or higher than 100 mg/dL;
  c) Large waist circumference wherein a large waist circumference is 40 inches or more for men and 35 inches or more for women;
  d) Low HDL cholesterol wherein low LDH cholesterol is under 40 mg/dL for men and under 50 mg/dL; and
  e) Triglycerides equal to or higher than 150 mg/dL.

In one embodiment, treating the metabolic syndrome comprises amelioration of elevated blood pressure equal to or higher than 130/85 mmHg.

In one embodiment, treating the metabolic syndrome comprises amelioration of elevated fasting blood glucose equal to or higher than 100 mg/dL.

In one embodiment, treating the metabolic syndrome comprises amelioration of large waist circumference wherein a large waist circumference is 40 inches or more for men and 35 inches or more for women.

In one embodiment, treating the metabolic syndrome comprises amelioration of low HDL cholesterol by increasing HDL cholesterol wherein low LDH cholesterol is under 40 mg/dL for men and under 50 mg/dL.

In one embodiment, treating the metabolic syndrome comprises amelioration of elevated triglycerides equal to or higher than 150 mg/dL.

In one embodiment, treating metabolic syndrome comprises amelioration of fatty liver.

In one embodiment, treating metabolic syndrome comprises modulation of fat deposition.

In another aspect, the invention provides a method of diagnosing a metabolic syndrome in a subject comprising:
  a) determining a level of HSP90β expression or activity in a sample from the subject; and
  b) comparing the level of HSP90β expression or activity in the sample from the subject to a control sample, wherein increased expression or activity of HSP90β in the subject sample as compared to the control sample is indicative of a metabolic disorder in the subject.

In one embodiment, the level of HSP90β expression comprises the level of expression of the HSP90β protein or the HSP90AB1 gene.

In one embodiment, the method further comprises treating the subject for the metabolic disorder.

In one embodiment, the metabolic syndrome comprises type 2 diabetes.

In one embodiment, the metabolic syndrome comprises type 1 diabetes.

In one embodiment, the metabolic syndrome comprises type insulin resistance.

In one embodiment, the metabolic syndrome comprises insulin insufficiency.

In one embodiment, the metabolic syndrome comprises obesity.

In one embodiment, the metabolic syndrome comprises hyperinsulinemia.

In one embodiment, the metabolic syndrome comprises impaired glucose tolerance (IGT).

In one embodiment, the subject with metabolic syndrome further exhibits one or more of the following signs:
  a) Blood pressure equal to or higher than 130/85 mmHg;
  b) Fasting blood glucose equal to or higher than 100 mg/dL;
  c) Large waist circumference wherein a large waist circumference is 40 inches or more for men and 35 inches or more for women;
  d) Low HDL cholesterol wherein low LDH cholesterol is under 40 mg/dL for men and under 50 mg/dL; and
  e) Triglycerides equal to or higher than 150 mg/dL.

In yet another aspect, the invention provides a method of monitoring a metabolic syndrome in a subject comprising:
  a) obtaining a sample from the subject at a first time point and at a second time point;
  b) determining a level of HSP90β expression or activity at the first time point and the second time point; and
  c) comparing the level of HSP90β expression or activity at the first time point to the level of HSP90β expression or activity at the second time point, wherein a change in the level of HSP90β expression or activity at the second time point relative to the first time point is indicative of a change in the metabolic syndrome in the subject.

In one embodiment, the level of HSP90β expression comprises the level of expression of the HSP90β protein or the HSP90AB1 gene.

In one embodiment, an increase in HSP90β expression or activity is indicative of worsening of the metabolic syndrome. In one embodiment, a decrease in HSP90β expression or activity is indicative of an improvement in the metabolic syndrome.

In one embodiment, the metabolic syndrome comprises type 2 diabetes.

In one embodiment, the metabolic syndrome comprises type 1 diabetes.

In one embodiment, the metabolic syndrome comprises type insulin resistance.

In one embodiment, the metabolic syndrome comprises insulin insufficiency.

In one embodiment, the metabolic syndrome comprises obesity.

In one embodiment, the metabolic syndrome comprises hyperinsulinemia.

In one embodiment, the metabolic syndrome comprises impaired glucose tolerance (IGT).

In one embodiment, the subject with metabolic syndrome further exhibits one or more of the following signs:
a) Blood pressure equal to or higher than 130/85 mmHg;
b) Fasting blood glucose equal to or higher than 100 mg/dL;
c) Large waist circumference wherein a large waist circumference is 40 inches or more for men and 35 inches or more for women;
d) Low HDL cholesterol wherein low LDH cholesterol is under 40 mg/dL for men and under 50 mg/dL; and
e) Triglycerides equal to or higher than 150 mg/dL.

Other embodiments are provided infra.

BRIEF DESCRIPTION OF THE DRAWINGS

FIG. 15 shows the sequence of human HSP90AA1 gene (SEQ ID NO: 7) and HSP90α protein (SEQ ID NO: 8).

FIG. 16 shows the sequence of human HSP90AB gene (SEQ ID NO: 9) and HSP90β protein (SEQ ID NO: 10).

FIG. 17 shows alignments of the sequences of the HSP90AA1 gene (SEQ ID NO: 7) with the human HSP90AB gene (SEQ ID NO: 9); and of the human HSP90α protein (SEQ ID NO: 8) with the human HSP90β protein (SEQ ID NO: 10).

DETAILED DESCRIPTION AND PREFERRED EMBODIMENTS

Figure 1:
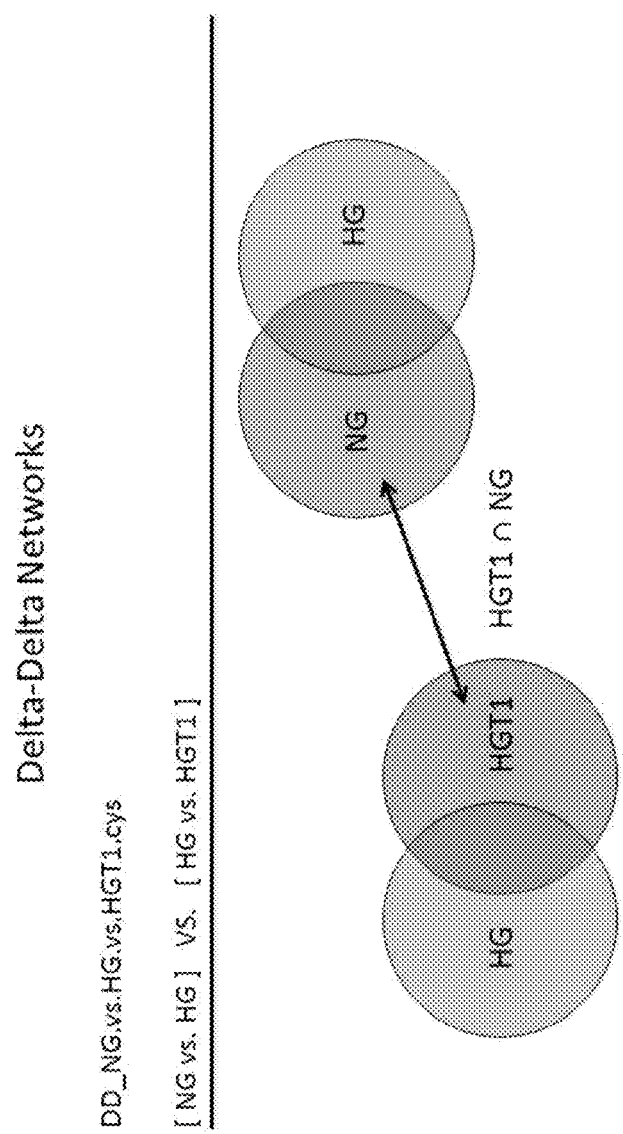
FIG. 1 is a schematic representation of the Delta-Delta networks used in the interrogatory platform method employing the diabetes model. HG is hyperglycemia; HGT1 is hyperglycemia with coenzyme Q10 treatment; and NG is normal glycemia.

A discovery platform technology was used to delineate distinct molecular signatures that drive the pathophysiology of diabetes and metabolic syndrome. Hsp90β was identified through this discovery platform technology as a critical node that is significantly modulated in human primary in vitro models of diabetes, and is associated with multiple mechanisms that are involved with lipid metabolism, proteasome function, endosomal trafficking, and RNA splicing.

Heat shock proteins (HSPs) are molecular chaperones that stabilizes a large set of client proteins. Vertebrates have two isoforms of cytosolic HSP90, HSP90α (gene HSP90AA1) and HSP90β (gene HSP90AB1). In vertebrates, the HSP90 isoforms are generally about 85% identical at the amino acid sequence level. In humans, the HSP90α amino acid sequence is 86% identical and 93% similar to the HSP90β amino acid sequence. Both proteins include an ATP binding domain. HSP90β is expressed constitutively at a high level in most cells and is generally more abundant than HSP90α. HSP90α expression is stress-inducible and the protein is overexpressed in many cancer cells. The client proteins of the HSP90 isoforms are largely overlapping, however HSP90α is responsible for chaperoning many signaling proteins, e.g., c-Src, A-raf, after heat shock.

Although in vitro analysis suggests similar and largely redundant functions, phenotypes for HSP90 knockout mice are strikingly different. The Hsp90β knockout mouse displays early embryonic lethality. In contrast, the only defect identified in Hsp90α-deficient mice occurs in adult males, which exhibit a failure of spermatogenesis. In the case of Hsp90β, lethality occurs at embryonic day 9, due to an inability of the embryo to develop a placenta, leading to a failure of implantation and death within 24 hours. These mutants express Hsp90α, yet failure still occurred, suggesting that Hsp90α cannot compensate for HSP90β in this crucial developmental step. In contrast to Hsp90β, both male and female Hsp90α knockout mice are viable and phenotypically normal into adulthood, with the exception of sterility in male mice. These results demonstrate that the two HSP90 isoforms play different roles in vivo in mice.

Using various functional assays with primary human skeletal muscle cells (HSMM) and hepatoma (HepG2) cells, was Applicants have demonstrated that RNAi mediated knockdown of HSP90β resulted in a decrease of the basal OCR/ECAR ratio by ~50%. The decreased ratio was due to decreased OCR in both HSMM and elevated ECAR in both HSMM and HepG2 cells, indicating that HSP90β regulates oxidative respiration and glycolysis. Moreover, HSP90β knockdown in HSMM cells increased glucose induced ECAR, demonstrating enhanced glycolysis induced by reduced HSP90β.

Further, Applicants have demonstrated that in primary human skeletal muscle cells, knocking down of HSP90β induced an increase in insulin stimulated glucose uptake, indicating that HSP90β is involved with skeletal muscle glucose metabolism and insulin action. Further, the observation by Applicants that knockdown of Hsp90β in myotubes results in significant downstream induction of pERK and a moderate influence on pAKT and pGSK3β suggests a functional bifurcation of insulin signaling and that Hsp90β is involved in a selective mechanism. In further experiments, Applicants have shown that a pan HSP90 small molecule inhibitor (CCT018159) that inhibits both HSP90α and HSP90β had a less profound effect than HSP90β knockdown alone on insulin signaling and bioenergetics. Accordingly, specific HSP90β inhibition was found to be more efficacious than a pan HSP90 inhibition approach.

In summary, the knockdown HSP90β was found by Applicants to have a significant effect on bioenergetics and mitochondrial substrate metabolism. In particular, HSP90β emerged from the studies described herein as a critical regulator of cellular metabolism and a molecular switch between oxidative respiration and glycolysis in skeletal muscle cells. HSP90β is therefore a viable therapeutic target in diabetes.

DEFINITIONS

As used herein, an "HSP90 inhibitor" is a therapeutic agent that reduces the expression or activity of HSP90. An HSP90 inhibitor may reduce HSP90 activity either by directly interacting with HSP90 or by reducing or preventing the formation of the HSP90/CDC37 complex such that the expression and proper folding of at least one client protein of HSP90 is inhibited. As used herein, an "HSP90" inhibitor can act by any mechanism, e.g., by inhibiting the expression of HSP90 at the RNA or protein level; by inhibiting the activity of HSP90, e.g., by inhibiting ATP binding or hydrolysis; or by inhibiting the interaction of HSP90 with one or more of its interacting proteins; or by decreasing the stability of HSP90. HSP90 inhibitors can inhibit the activity of one or more HSP90 isoforms. For example, an inhibitor of HSP90α may also inhibit HSP90β. Similarly, an inhibitor of HSP90β may also inhibit HSP90α. In one embodiment, HSP90 inhibitors can be specific for the inhibition of a specific HSP90 isoform, for example, specific for the inhibition of HSP90β, i.e., predominantly inhibiting HSP90β while inhibiting HSP90α far less.

HSP90 inhibitors include (i) small molecule inhibitors, many of which inhibit the activity of multiple isoforms of HSP90, e.g., radicicol and geldanamycin and its derivatives; (ii) nucleic acid inhibitors, e.g., antisense, siRNA, shRNA, dsiRNA, etc. that can target one or more specific isoforms of HSP90 (see, e.g., examples provided herein; Kuo et al., 2007, J. Immunol. 178:600; Didelot et ah, 2008, Cell. Death Diff., 15:859, the entire contents of each of which are incorporated herein by reference); and (iii) antibodies that can target one or more specific isoforms of HSP90 (Cortes-González et ah, 2010, Cell Physiol. Biochem. 26:657, the entire contents of which is incorporated herein by reference). Specific classes and examples of HSP90 inhibitors are discussed in detail herein.

As used herein, an HSP90 inhibitor that is "specific" for a particular HSP90 isoform, e.g., specific for HSP90β, may have a significantly lower activity against another HSP isoform. However, as used herein, a "specific" inhibitor of a particular HSP90 isoform is at least 2-fold, at least 3-fold, at least 4-fold, at least 5-fold, at least 6-fold, at least 7-fold, at least 8-fold, at least 9-fold, at least 10-fold, at least 20-fold, at least 30-fold, at least 50-fold, at least 75-fold, or at least 100-fold more effective at inhibiting the activity or expression of the specific HSP90 isoform. For example, if the inhibitor is an siRNA specific for HSP90β that is at least 10-fold more effective at inhibiting a specific HSP90 isoform, then 1 nM of the siRNA will decrease expression of HSP90β to the same extend as 10 nM of the siRNA will decrease the expression of HSP90α. Similar analyses can be performed to compare the effect of inhibitors on the activity of the HSP90 isoforms, e.g., level of inhibition of phosphorylation of downstream effectors, inhibition of folding of client proteins, inhibition of inorganic phosphate production, etc. In certain embodiments, a specific inhibitor of an HSP90β isoform inhibits the expression or activity of HSP90β by at least 50%, but does not inhibit the expression or activity of HSP90α by 50%, 40%, 30%, 20%, or 10% at the same concentration. In certain embodiments, a specific inhibitor of an HSP90β isoform inhibits the expression or activity of HSP90β by at least 60%, but does not inhibit the expression or activity of HSP90α by 50%, 40%, 30%, 20%, or 10% at the same concentration. In certain embodiments, a specific inhibitor of an HSP90β isoform inhibits the expression or activity of HSP90β by at least 70%, but does not inhibit the expression or activity of HSP90α by 50%, 40%, 30%, 20%, or 10% at the same concentration. In certain embodiments, a specific inhibitor of an HSP90β isoform inhibits the expression or activity of HSP90β by at least 80%, but does not inhibit the expression or activity of HSP90α by 50%, 40%, 30%, 20%, or 10% at the same concentration. In certain embodiments, a specific inhibitor of an HSP90β isoform inhibits the expression or activity of HSP90β by at least 90%, but does not inhibit the expression or activity of HSP90α by 50%, 40%, 30%, 20%, or 10% at the same concentration.

Assay methods to determine the specificity and activity of HSP90 inhibitors are within the ability of those of skill in the art. The specific assay method can depend on the inhibitor used, e.g, an inhibitor of activity or an inhibitor of expression. Kits to assay HSP90α and HSP90β activity are commercially available (e.g., BPS Bioscience, San Diego, Calif.). Methods to assay activity of HSP90α and HSP90β are also known in the art (see, e.g., Kim et ah, *J. Biomol. Screening* 2004; 9: 375-381; and Howes et ah, *Anal. Biochem.* 2006; 350:202-213, the entire contents of both of which is incorporated herein by reference).

For instance, inhibition of the Hsp90 activity can be determined in an assay for ATPase activity, e.g., Malachite Green Assay as described in Methods Mol Med, 2003, 85:149. Briefly, an Hsp90 protein (e.g., Hsp90α and Hsp90β proteins) in assay buffer (100 mM Tris-HCl, pH7.4, 20 mM KCl, 6 mM $MgCl_2$) is mixed with ATP alone (a negative control), ATP with geldanamycin (a positive control), ATP with a test compound at varying concentrations, or a test compound alone (another negative control) in a 96-well plate. For detecting inorganic phosphate produced by hydrolysis of ATP, Malachite green reagent is then added to the reaction. The mixtures are incubated at 37° C. for 4 hours and, at the end of the incubation, sodium citrate buffer (34% w/v sodium citrate) is added to the reaction. The plate is read by an ELISA reader with an absorbance at 620 nm. Activity against HSP90α and Hsp90β can be compared to determine the specificity, if any, of the inhibitor. Such assays allow for direct comparison of activity of inhibitors against each of the HSP90 isoforms.

Alternatively, inhibition of Hsp90 activity can be determined in a competitive binding assay. Geldanamycin is known to interact with the ATP-binding site of Hsp90α or Hsp90β and can be readily displaced by other Hsp90 inhibitors. The determination of the displacement is facilitated by labeling geldanamycin either fluorescently or non-fluorescently. An exemplary competitive binding assay using fluorescently-labeled geldanamycin is described in Yin, et al., Int J. Cancer. 2010 Mar. 1; 126(5): 1216-25 (incorporated herein by reference). Briefly, a FITC-geldanamycin probe is first reduced with TCEP at room temperature for 3 h, after which the solution is aliquoted and stored at −80° C. until used. Recombinant human Hsp90α or Hsp90β and reduced FITC-geldanamycin are incubated in a 96-well microplate at room temperature for 3 h in the presence of assay buffer containing 20 mM HEPES (pH 7.4), 50 mM KCl, 5 mM $MgCl_2$, 20 mM $Na_2MoO_4$, 2 mM DTT, 0.1 mg/mL BGG, and 0.1% (v/v) CHAPS. As a negative control, Hsp90 protein is not included in the preincubation. Following this preincubation, a test compound (as a competitor) in a solvent is then added to final concentrations of 0.2 nM to 10 µM (final volume 100 µL). As a positive control, a non-labeled geldanamycin is used as a competitor. As a negative control, neither a test compound nor non-labeled geldanamycin is added. The reaction is incubated for 16 h at room temperature and fluorescence is then measured in an Analyst plate reader, excitation=485 nm, emission=535 nm. High and low controls contained no compound or no Hsp90, respectively. The data are fit to a four-parameter curve using GraphPad Prism and $IC_{50}$ values are generated. The $IC_{50}$ values are converted into inhibition constants (Ki) using the modified Cheng-Prusoff equation as described in, e.g., Machida, et al, Cancer Sci 2005; 96:911-17 (31). Activity against HSP90α and Hsp90β can be compared to determine the specificity, if any, of the inhibitor.

Alternatively, HSP90 activity can be assayed in cells that express only a single HSP90 isoform is present (e.g., yeast, C. elegans, or mammalian cells expressing only HSP90α or HSP90β). Inhibition of folding and/or stability of a client protein of both isoforms of HSP90 is assayed to determine the relative activities of the inhibitors. As used herein, a "nucleic acid" inhibitor of HSP90 is any nucleic acid based inhibitor that causes a decrease in the expression of an HSP90 by hybridizing with at least a portion of the RNA transcript from the HSP90AA1 and/or HSP90AB1 gene to result in a decrease in the expression of the HSP90α or HSP90β. Nucleic acid inhibitors include, for example, single stranded nucleic acid molecules, e.g., antisense nucleic acids, and double stranded nucleic acids such as siRNA, shRNA, dsiRNA (see, e.g., US Patent publication 20070104688). As used herein, double stranded nucleic acid molecules are designed to be double stranded over at least 12, preferably at least 15 nucleotides. Double stranded nucleic acid molecules can be a single nucleic acid strand designed to hybridize to itself, e.g., an shRNA. It is understood that a nucleic acid inhibitor of HSP90 can be administered as an isolated nucleic acid. Alternatively, the nucleic acid inhibitor can be administered as an expression construct to produce the inhibitor in the cell. In certain embodiments, the nucleic acid inhibitor includes one or more chemical modifications to improve the activity and/or stability of the nucleic acid inhibitor. Such modifications are well known in the art. The specific modifications to be used will depend, for example, on the type of nucleic acid inhibitor.

As used herein, an "antibody" is a protein that includes at least one complementary determining region that binds to a specific target antigen. An antibody frequently includes at least one immunoglobulin variable region, e.g., an amino acid sequence that provides an immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab, F(ab')2, Fd, Fv, and dAb fragments) as well as complete antibodies, e.g., intact immunoglobulins of types IgA, IgG, IgE, IgD, IgM (as well as subtypes thereof). The light chains of the immunoglobulin can be of types kappa or lambda. In one embodiment, the antibody is glycosylated. For example, an antibody can be a polyclonal antibody, a monoclonal antibody, a modified antibody, a chimeric antibody, a reshaped antibody, a humanized antibody, a Fab fragment, a F(ab')2 fragment, a Fd fragment, a Fv fragment, a dAb fragment, single chain Fv, a dimerized variable region (V region) fragment (diabody), a disulfide-stabilized V region fragment (dsFv), affibodies, antibody mimetics, and one or more isolated complementarity determining regions (CDR) that retain specific binding to the payload. As used herein, an "isolated" CDR is a CDR not in the context of a naturally occurring antibody. The antibody can be any immunoglobulin type, e.g., IgG, IgM, IgA1, IgA2, IgD, or IgE. In an embodiment, the antibody can be a human antibody.

As used herein, a "small molecule" inhibitor is an inhibitor molecule that has a molecular weight of less than 1000 Da, preferably less than 750 Da, or preferably less than 500 Da. In certain embodiments, a small molecule does not include a nucleic acid molecule. In certain embodiments, a small molecule does not include a peptide more than three amino acids in length.

As used herein, for the sake of simplicity, a change or modulation in the expression or activity, i.e., increase or decrease, of an HSP90, e.g., HSP90α and/or HSP90β, expression or activity is understood to include a change in expression or activity of the gene and/or the protein. In an embodiment, expression or activity is reduced by at least about 10%, 20%, 30%, 40%, 50%, 60%, 70%, 75%, 80%, 85%, 90%, 95%, or 99%.

As used herein, a change in HSP90 "activity" can be detected, for example, by detecting a change in the ATP hydrolysis activity of HSP90, e.g., HSP90α and/or HSP90β, by detecting a change in the folding of client proteins of the specific HSP90. Methods for detection of ATP hydrolysis are well known in the art. Folding of client proteins can be assessed, for example, by determining the amount of a client protein present in the sample or by determining the activity of the client protein in the sample when the client protein is a signaling protein that has enzymatic activity, e.g., kinase activity. Kits to assay HSP90α and HSP90β activity are also commercially available (e.g., from BPS Bioscience).

As used herein, a subject suffering from "metabolic syndrome" is intended to refer to a subject having one or more of the following conditions: type 2 diabetes, insulin resistance, insulin insufficiency, obesity, hyperinsulinemia, or impaired glucose tolerance (IGT); or as having three or more of the following signs of metabolic syndrome.
   a) Blood pressure equal to or higher than 130/85 mmHg;
   b) Fasting blood glucose equal to or higher than 100 mg/dL;
   c) Large waist circumference wherein a large waist circumference is 40 inches or more for men and 35 inches or more for women;
   d) Low HDL cholesterol wherein low LDH cholesterol is under 40 mg/dL for men and under 50 mg/dL; and
   e) Triglycerides equal to or higher than 150 mg/dL.
Methods to diagnose the indicated conditions and to detect the indicated signs of metabolic syndrome are routine in the art. In certain embodiments, metabolic syndrome further includes type 1 diabetes. In certain embodiments, metabolic syndrome does not include type 1 diabetes. Associated diseases and signs include hyperuricemia, fatty liver (especially in concurrent obesity) progressing to non-alcoholic fatty liver disease (NAFLD), polycystic ovarian syndrome (in women), and acanthosis nigricans. In certain embodiments, the invention includes treatment of one or more of these associated diseases or signs. In certain embodiments, the invention does not include treatment of one or more of these associated diseases or signs.

As used herein, "diabetes" is intended to refer to either type 1 diabetes or type 2 diabetes, or both type 1 and type 2 diabetes. In certain embodiments, diabetes includes pre-diabetes. In certain embodiments, diabetes does not include pre-diabetes.

As used herein, "insulin resistance" and "insulin insensitivity" can be used interchangeably and refers to conditions wherein the amount of insulin is less effective at lowering blood sugar than in a normal subject resulting in an increase in blood sugar above the normal range that is not due to the absence of insulin. Without being bound by mechanism, the conditions are typically associated with a decrease in signaling through the insulin receptor. Typically, insulin resistance in muscle and fat cells reduces glucose uptake and storage as glycogen and triglycerides, respectively. Insulin resistance in liver cells results in reduced glycogen synthesis and a failure to suppress glucose production and release into the blood.

Insulin resistance is often present in the same subject together with "insulin insufficiency", which also results in an increase in blood sugar above the normal range that is not due to the absence of insulin. Insulin insufficiency is a condition related to a lack of insulin action in which insulin is present and produced by the body. It is distinct from type 1 diabetes in which insulin is not produced due to the lack of islet cells.

For the purposes of determining if a subject has metabolic syndrome, it is not important to distinguish if a subject suffers from insulin resistance, insulin insufficiency, or both.

As used herein, "obesity" can be defined using any clinically relevant definitions. For example, in adults, body mass index (BMI, $kg/m^2$) is frequently used as a measure of overweight and obesity, with overweight being defined as a BMI 25-29.9 $kg/m^2$, obesity as a BMI equal to or greater than 30 $kg/m^2$, and morbid obesity being defined as BMIs over 40 $kg/m^2$. Obesity can also be defined in adults by central adiposity as measured by waist circumference, with raised waist circumference defined as equal to or greater than 102 cm in men and equal to or greater than 88 cm in women. Treatment of obesity does not require a decrease of BMI or waist circumference to normal levels. Instead, treatment preferably includes a decrease of at least 2%, at least 3%, at least 4%, at least 5%, at least 7%, at least 10%, at least 15%, at least 20%, 30%, 40%, 50%, 60%, 70%, or more of the excess BMI value or excess waist circumference over an upper normal limit for the subject. For example a woman with a waist circumference of 100 cm would have an excess waist circumference of 12 cm (100 cm–88 cm). Reduction of the excess by 20% would be a 2.4 cm reduction.

"Hyperinsulinemia" is defined as the condition in which a subject with insulin resistance, with or without euglycemia, in which the fasting or postprandial serum or plasma insulin concentration is elevated above that of normal, lean individuals without insulin resistance (i.e., 100 mg/dl in a fasting plasma glucose test or 140 mg/dl in an oral glucose tolerance test), further having a waist-to-hip ratio <1.0 (for men) or <0.8 (for women).

The term "impaired glucose tolerance" (IGT) or "pre-diabetes" is used to describe a person who, when given a glucose tolerance test, has a blood glucose level that falls between normal and hyperglycemic. Such a person is at a higher risk of developing diabetes although they are not considered to have diabetes. For example, impaired glucose tolerance refers to a condition in which a patient has a fasting blood glucose concentration or fasting serum glucose concentration greater than 110 mg/dl and less than 126 mg/dl (7.00 mmol/L), or a 2 hour postprandial blood glucose or serum glucose concentration greater than 140 mg/dl (7.78 mmol/L) and less than 200 mg/dl (11.11 mmol/L). Mounting evidence suggests that the pre-diabetes condition may be a risk factor for developing cardiovascular disease (Diabetes Care 26:2910-2914, 2003). Prediabetes, also referred to as impaired glucose tolerance or impaired fasting glucose is a major risk factor for the development of type 2 diabetes mellitus, cardiovascular disease and mortality. Much focus has been given to developing therapeutic interventions that prevent the development of type 2 diabetes by effectively treating prediabetes (Pharmacotherapy, 24:362-71, 2004).

The condition of "hyperglycemia" (high blood sugar) is a condition in which the blood glucose level is too high. Typically, hyperglycemia occurs when the blood glucose level rises above 180 mg/dl. Symptoms of hyperglycemia include frequent urination, excessive thirst and, over a longer time span, weight loss.

The condition of "hypoglycemia" (low blood sugar) is a condition in which the blood glucose level is too low. Typically, hypoglycemia occurs when the blood glucose level falls below 70 mg/dl. Symptoms of hypoglycemia include moodiness, numbness of the extremities (especially in the hands and arms), confusion, shakiness or dizziness. Since this condition arises when there is an excess of insulin over the amount of available glucose it is sometimes referred to as an insulin reaction.

As used herein, an "HbA1c level" is understood as a hemoglobin A1e (HbA1c) level determined from an HbA1c test, which assesses the average blood glucose levels during the previous two and three months, may be employed. A person without diabetes typically has an HbA1c value that ranges between 4% and 6%. Prediabetes is characterized by an HbA1c level of 5.7% to 6.5%, with an Hb1Ac level greater than 6.5% being indicative of diabetes. For every 1% increase in HbA1c, blood glucose levels increases by approximately 30 mg/dL and the risk of complications due to persistent elevated blood glucose increases. Preferably, the HbA1c value of a patient being treated according to the present invention is reduced to less than 9%, less than 7%, less than 6%, and most preferably to around 5%. Thus, the excess HbA1c level of the patient being treated (i.e., the Hb1Ac level in excess of 5.7%) is preferably lowered by at least 10%, 20%, 30%, 40%, 50%, 60%, 70%, 80%, 90%, or more relative to such levels prior to treatment.

As used herein, the term "subject" refers to human and non-human animals, including veterinary subjects. The term "non-human animal" includes all vertebrates, e.g., mammals and non-mammals, such as non-human primates, mice, rabbits, sheep, dog, cat, horse, cow, chickens, amphibians, and reptiles. In a preferred embodiment, the subject is a human and may be referred to as a patient.

As used herein, the terms "treat," "treating" or "treatment" refer, preferably, to an action to obtain a beneficial or desired clinical result including, but not limited to, alleviation or amelioration of one or more signs or symptoms of a disease or condition, diminishing the extent of disease, stability (i.e., not worsening) state of disease, amelioration or palliation of the disease state. As used herein, treatment can include one or more of reduction of insulin resistance, increasing insulin sensitivity, decreasing insulin deficiency, improving or normalizing HbAcl levels, improving or normalizing blood glucose levels, reducing body weight, reducing waist measurement, normalizing or reducing HDL levels, normalizing or reducing triglyceride levels, and ameliorating at least one sign or symptom of diabetes. Treatment does not need to be curative. Treatment outcomes need not be determined quantitatively. However, in certain embodiments, treatment outcomes can be quantitated by considering percent improvement towards a normal value at the end of a range. For example, metabolic syndrome is characterized by an excess of some measures (e.g., weight/BMI, waist circumference, triglyceride levels) and a deficiency in other measures (e.g., a deficiency in HDL cholesterol or insulin response). A woman with a waist circumference of 100 cm would have an excess waist circumference of 12 cm (100 cm-88 cm, the maximum normal waist circumference). Reduction of the excess waist circumference by 20% would be a 2.4 cm reduction in excess waist circumference. Similar calculations can be made for other values. A man with an HDL of 30 mg/dl would have a deficiency of 20 mg/dl (normal value for men is at least 50 mg/dl). An increase of 5 mg/dl to 25 mg/dl would be considered to reduce the deficiency of HLD by 25%.

As used herein, "reducing glucose levels" means reducing the elevated level of glucose by at least 10%, 20%, 30%, 40%, 50%, 60%, 70%, 80%, 90%, 95%, or more to achieve a normalized glucose level, i.e., a glucose level no greater than 150 mg/dl. Desirably, glucose levels are reduced to normoglycemic levels, i.e., between 150 to 60 mg/dL, between 140 to 70 mg/dL, between 130 to 70 mg/dL, between 125 to 80 mg/dL, and preferably between 120 to 80 mg/dL. Such reduction in glucose levels may be obtained by increasing any one of the biological activities associated with the clearance of glucose from the blood. Accordingly, an agent having the ability to reduce glucose levels may increase insulin production, secretion, or action. Insulin action may be increased, for example, by increasing glucose uptake by peripheral tissues and/or by reducing hepatic glucose production. Alternatively, the agent of the invention may reduce the absorption of carbohydrates from the intestines, alter glucose transporter activity (e.g., by increasing GLUT4 expression, intrinsic activity, or translocation), increase the amount of insulin-sensitive tissue (e.g., by increasing muscle cell or adipocyte cell differentiation), or alter gene transcription in adipocytes or muscle cells (e.g., altered secretion of factors from adipocytes expression of metabolic pathway genes). Desirably, the agent of the invention increases more than one of the activities associated with the clearance of glucose.

By "reducing lipid levels" is meant reducing the level of excess lipids by at least 1%, 5%, 10%, 20%, 30%, 40%, 50%, 60%, 70%, 80%, 90%, 95%, or more to achieve a normal lipid level, i.e., no greater than 150 mg/dl.

By "alter insulin signaling pathway such that glucose levels are reduced" is meant to alter (by increasing or reducing) any one of the activities involved in insulin signaling such that the overall result is an increase in the clearance of glucose from plasma. For example, altering the insulin signaling pathway thereby causing an increase in insulin production, secretion, or action, an increasing glucose uptake by peripheral tissues, a reducing hepatic glucose production, or a reducing the absorption of carbohydrates from the intestines.

A "therapeutically effective amount" is that amount sufficient to treat a disease in a subject. A therapeutically effective amount can be administered in one or more administrations.

By "diagnosing" and the like, as used herein, refers to a clinical or other assessment of the condition of a subject based on observation, testing, or circumstances for identifying a subject having a disease, disorder, or condition based on the presence of at least one indicator, such as a sign or symptom of the disease, disorder, or condition. Typically, diagnosing using the method of the invention includes the observation of the subject for multiple indicators of the disease, disorder, or condition in conjunction with the methods provided herein. Diagnostic methods provide an indicator that a disease is or is not present. A single diagnostic test typically does not provide a definitive conclusion regarding the disease state of the subject being tested.

As used herein, "monitoring" is understood as assessing at least one sign or symptom of a disease in a subject at a first time point and at a later second time point, comparing the severity of the sign(s) or symptom(s) of the condition, and determining of the condition became more or less severe over time.

The terms "administer", "administering" or "administration" include any method of delivery of a pharmaceutical composition or agent into a subject's system or to a particular region in or on a subject. In certain embodiments, the agent is administered enterally or parenterally. In certain embodiments of the invention, an agent is administered intravenously, intramuscularly, subcutaneously, intradermally, intranasally, orally, transcutaneously, or mucosally. In certain preferred embodiments, an agent is administered intravenously. In certain embodiments, the agent is administered locally or systemically. Administering an agent can be performed by a number of people working in concert. Administering an agent includes, for example, prescribing an agent to be administered to a subject and/or providing instructions, directly or through another, to take a specific agent, either by self-delivery, e.g., as by oral delivery, subcutaneous delivery, intravenous delivery through a central line, etc.; or for delivery by a trained professional, e.g., intravenous delivery, intramuscular delivery, etc.

The term "sample" as used herein refers to a collection of similar fluids, cells, or tissues isolated from a subject. The term "sample" includes any body fluid (e.g., urine, serum, blood fluids, lymph, gynecological fluids, cystic fluid, ascetic fluid, ocular fluids, and fluids collected by bronchial lavage and/or peritoneal rinsing), ascites, tissue samples (e.g., tumor samples) or a cell from a subject. Other subject samples include tear drops, serum, cerebrospinal fluid, feces, sputum, and cell extracts. In a particular embodiment, the sample is urine or serum. In another embodiment, the sample does not include ascites or is not an ascites sample. In one embodiment, the sample comprises cells. In another embodiment, the sample does not comprise cells.

The term "control sample," as used herein, refers to any clinically relevant comparative sample, including, for example, a sample from a healthy subject not afflicted with metabolic syndrome or a sample from a subject from an earlier time point, e.g., prior to treatment, at an earlier stage of treatment. A control sample can be a purified sample, protein, and/or nucleic acid provided with a kit. Such control samples can be diluted, for example, in a dilution series to allow for quantitative measurement of analytes in test samples. A control sample may include a sample derived from one or more subjects. A control sample may also be a sample made at an earlier time point from the subject to be assessed. For example, the control sample could be a sample taken from the subject to be assessed before the onset of metabolic syndrome, at an earlier stage of disease, or before the administration of treatment or of a portion of treatment. The control sample may also be a sample from an animal model, or from a tissue or cell lines derived from the animal model of metabolic syndrome. The level of HSP90, e.g., HSP90α and/or HSP90β, activity or expression in a control sample that consists of a group of measurements may be determined, e.g., based on any appropriate statistical measure, such as, for example, measures of central tendency including average, median, or modal values.

The term "control level" refers to an accepted or predetermined level of a sign of a metabolic disorder in a subject or a subject sample. The following levels are considered to be normal levels:

Blood pressure less than or equal to 120/80 mmHG
Fasting blood glucose less than or equal to 100 mg/dl.
Waist cirucumference, less than 40 inches (102 cm) for men and less than 35 inches (88 cm) for women.
HDL at least 50 mg/dl for women, at least 40 mg/dl for men.
Triglycerides less than or equal to 150 mg/dl.
HbA1c less than or equal to 5.7%.
Oral glucose tolerance test less than or equal to 140 mg/dl.

As used herein, the term "obtaining" is understood to refer to manufacturing, purchasing, or otherwise coming into possession of.

As used herein, "detecting", "detection" and the like are understood to refer to an assay performed for identification of a specific analyte in a sample, e.g., an HSP90, e.g., HSP90α and/or HSP90β, expression or activity level in a sample. The amount of analyte or activity detected in the sample can be none or below the level of detection of the assay or method.

The terms "modulate" or "modulation" refer to upregulation (i.e., activation or stimulation), downregulation (i.e., inhibition or suppression) of a level, or the two in combination or apart. A "modulator" is a compound or molecule that modulates, and may be, e.g., an agonist, antagonist, activator, stimulator, suppressor, or inhibitor.

The term "expression" is used herein to mean the process by which a polypeptide is produced from DNA. The process involves the transcription of the gene into mRNA and the translation of this mRNA into a polypeptide. Depending on the context in which used, "expression" may refer to the production of RNA, or protein, or both.

The terms "level of expression of a gene" or "gene expression level" refer to the level of mRNA, as well as pre-mRNA nascent transcript(s), transcript processing intermediates, mature mRNA(s) and degradation products, or the level of protein, encoded by the gene in the cell.

As used herein, "level of activity" is understood as the amount of protein activity, typically enzymatic activity, as determined by a quantitative, semi-quantitative, or qualitative assay. Activity is typically determined by monitoring the amount of product produced in an assay using a substrate that produces a readily detectable product, e.g., colored product, fluorescent product, or radioactive product. The specific assay performed depends, for example, on the activity to be measured.

The articles "a", "an" and "the" are used herein to refer to one or to more than one (i.e. to at least one) of the grammatical object of the article unless otherwise clearly indicated by contrast. By way of example, "an element" means one element or more than one element.

The term "including" is used herein to mean, and is used interchangeably with, the phrase "including but not limited to".

The term "or" is used herein to mean, and is used interchangeably with, the term "and/or," unless context clearly indicates otherwise.

The term "such as" is used herein to mean, and is used interchangeably, with the phrase "such as but not limited to".

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

The recitation of a listing of chemical group(s) in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Reference will now be made in detail to preferred embodiments of the invention. While the invention will be described in conjunction with the preferred embodiments, it will be understood that it is not intended to limit the invention to those preferred embodiments. To the contrary, it is intended to cover alternatives, modifications, and equivalents as may be included within the spirit and scope of the invention as defined by the appended claims.

I. Metabolic Syndrome

Metabolic syndrome (Syndrome X) is a name for a group of risk factors that occur together and increase the risk for coronary artery disease, stroke, and type 2 diabetes (www.ncbi.nlm.nih.gov/pubmedhealth/PMH0004546/). Metabolic syndrome is becoming more and more common in the United States. Researchers are not sure whether the syndrome is due to one single cause, but all of the risks for the syndrome are related to obesity. As used herein, metabolic syndrome is understood to include insulin resistance, insulin insufficiency, pre-diabetes, type 2 diabetes, and obesity. A subject who meets the diagnostic criteria below is also understood as having metabolic syndrome. In some embodiments of the invention, metabolic syndrome can also include type 1 diabetes. In other embodiments, metabolic syndrome does not include type 1 diabetes.

The two most important risk factors for metabolic syndrome are extra weight around the middle and upper parts of the body (central obesity) and insulin resistance, in which the body cannot use insulin effectively. Insulin controls the amount of sugar in the body. In subjects in which the body does not produce enough insulin and/or the body does not respond to the level of insulin that is produce, blood sugar and fat levels rise. Other risk factors for metabolic syndrome include aging, genetic factors, hormone changes, and a sedentary lifestyle. People with metabolic syndrome frequently suffer from one or both of excessive blood clotting and low levels of systemic inflammation, both of which can exacerbate the condition.

The American Heart Association and the National Heart, Lung, and Blood Institute, consider metabolic syndrome to be present in subjects having three or more of the following signs:
  Blood pressure equal to or higher than 130/85 mmHg
  Fasting blood sugar (glucose) equal to or higher than 100 mg/dL
  Large waist circumference (length around the waist):
    Men—40 inches or more
    Women—35 inches or more
  Low HDL cholesterol:
    Men—under 40 mg/dL
    Women—under 50 mg/dL
  Triglycerides equal to or higher than 150 mg/dL Treatment includes recommended lifestyle changes or medicines to help reduce blood pressure, LDL cholesterol, and blood sugar, e.g., lose weight, increase exercise. Blood pressure and cholesterol may also be regulated using appropriate drugs.

In addition to having an increased long-term risk for developing cardiovascular disease and type 2 diabetes, complications of metabolic syndrome further include atherosclerosis, heart attack, kidney disease, non-alcoholic fatty liver disease, peripheral artery disease, and stroke, as well as complications typically associated with diabetes.

A. Diabetes, Insulin Resistance, and Insulin Insufficiency

Diabetes mellitus (DM), often simply referred to as diabetes, is a group of metabolic diseases in which a person has high blood sugar, either because the body does not produce enough insulin, or because cells do not respond to the insulin that is produced. This high blood sugar produces the classical symptoms of polyuria (frequent urination), polydipsia (increased thirst) and polyphagia (increased hunger).

Type 2 diabetes results from insulin resistance, a condition in which cells fail to use insulin properly, sometimes combined with an absolute insulin deficiency. The defective responsiveness of body tissues to insulin is believed, at least in part, to involve the insulin receptor. However, the specific defects are not known.

In the early stage of type 2 diabetes, the predominant abnormality is reduced insulin sensitivity. At this stage, hyperglycemia can be reversed by a variety of measures and medications that improve insulin sensitivity or reduce glucose production by the liver. Prediabetes indicates a condition that occurs when a person's blood glucose levels are higher than normal but not high enough for a diagnosis of type 2 diabetes.

Type 2 diabetes is due to insufficient insulin production from beta cells in the setting of insulin resistance. Insulin resistance, which is the inability of cells to respond adequately to normal levels of insulin, occurs primarily within the muscles, liver and fat tissue. In the liver, insulin normally suppresses glucose release. However in the setting of insulin resistance, the liver inappropriately releases glucose into the blood. The proportion of insulin resistance verses beta cell dysfunction differs among individuals with some having primarily insulin resistance and only a minor defect in insulin secretion and others with slight insulin resistance and primarily a lack of insulin secretion.

Other potentially important mechanisms associated with type 2 diabetes and insulin resistance include: increased breakdown of lipids within fat cells, resistance to and lack of incretin, high glucagon levels in the blood, increased retention of salt and water by the kidneys, and inappropriate regulation of metabolism by the central nervous system. However not all people with insulin resistance develop diabetes, since an impairment of insulin secretion by pancreatic beta cells is also required.

Type 1 diabetes results from the body's failure to produce insulin, and presently requires treatment with injectable insulin. Type 1 diabetes is characterized by loss of the insulin-producing beta cells of the islets of Langerhans in the pancreas, leading to insulin deficiency. Most affected people are otherwise healthy and of a healthy weight when onset occurs. Sensitivity and responsiveness to insulin are usually normal, especially in the early stages. However, particularly in late stages, insulin resistance can occur.

B. Secondary Pathologies of Diabetes, Insulin Resistance, and Insulin Insufficiency Abnormal glucose regulation resulting from diabetes, both type 1 and type 2, insulin resistance, and insulin insufficiency are associated with secondary pathologies, many of which result from poor circulation. Such secondary pathologies include macular degeneration, peripheral neuropathies, ulcers and decrease wound healing, and decreased kidney function. It has been suggested that maintaining glucose levels and/or HbAcl levels within normal ranges decreases the occurrence of these secondary pathologies. It is understood that normalization of blood glucose, insulin, and Hb1Ac levels will reduce the development of secondary pathologies by limiting the primary pathology, e.g., metabolic syndrome. In certain embodiments, HSP90 inhibitors, especially HSP90β inhibitors and HSP90β specific inhibitors, are not used for the treatment of secondary pathologies associated with diabetes and metabolic syndromes. In certain embodiments, HSP90 inhibitors, especially HSP90β inhibitors and HSP90β specific inhibitors, are used for the treatment of secondary pathologies associated with diabetes and metabolic syndromes.

II. Dosages and Modes of Administration

Techniques and dosages for administration vary depending on the type of compound (e.g., chemical compound, antibody, or nucleic acid) and are well known to those skilled in the art or are readily determined.

Therapeutic compounds of the present invention may be administered with a pharmaceutically acceptable diluent, carrier, or excipient, in unit dosage form. Administration may be parenteral, intravenous, subcutaneous, oral, topical, or local. Administering an agent can be performed by a number of people working in concert. Administering an agent includes, for example, prescribing an agent to be administered to a subject and/or providing instructions, directly or through another, to take a specific agent, either by self-delivery, e.g., as by oral delivery, subcutaneous delivery, intravenous delivery through a central line, etc; or for delivery by a trained professional, e.g., intravenous delivery, intramuscular delivery, intratumoral delivery, etc.

The composition can be in the form of a pill, tablet, capsule, liquid, or sustained release tablet for oral administration; or a liquid for intravenous, subcutaneous, or parenteral administration; or a polymer or other sustained release vehicle for local administration.

Methods well known in the art for making formulations are found, for example, in "Remington: The Science and Practice of Pharmacy" (20th ed., ed. A. R. Gennaro, 2000, Lippincott Williams & Wilkins, Philadelphia, Pa.). Formulations for parenteral administration may, for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. The concentration of the compound in the formulation varies depending upon a number of factors, including the dosage of the drug to be administered, and the route of administration.

The compound may be optionally administered as a pharmaceutically acceptable salt, such as non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids and the like; polymeric acids such as tannic acid, carboxymethyl cellulose, and the like; and inorganic acid such as hydrochloric acid, hydrobromic acid, sulfuric acid phosphoric acid, and the like. Metal complexes include zinc, iron, and the like.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and anti-adhesives (e.g., magnesium stearate, zinc stearate, stearic acid, silicas, hydrogenated vegetable oils, or talc). Formulations for oral use may also be provided as chewable tablets, or as hard gelatin capsules wherein the active ingredient is mixed with an inert solid diluent, or as soft gelatin capsules wherein the active ingredient is mixed with water or an oil medium.

The dosage and the timing of administering the compound depend on various clinical factors including the overall health of the subject and the severity of the symptoms of disease, e.g., diabetes, metabolic syndrome.

III. Nucleic Acid Therapeutics

Nucleic acid therapeutics are well known in the art. Nucleic acid therapeutics include both single stranded and double stranded (i.e., nucleic acid therapeutics having a complementary region of at least 15 nucleotides in length) nucleic acids that are complementary to a target sequence in a cell. Nucleic acid therapeutics can be delivered to a cell in culture, e.g., by adding the nucleic acid to culture media either alone or with an agent to promote uptake of the nucleic acid into the cell. Nucleic acid therapeutics can be delivered to a cell in a subject, i.e., in vivo, by any route of administration. The specific formulation will depend on the route of administration.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

Sequences can be "fully complementary" with respect to each when there is base-pairing of the nucleotides of the first nucleotide sequence with the nucleotides of the second nucleotide sequence over the entire length of the first and second nucleotide sequences. However, where a first sequence is referred to as "substantially complementary" with respect to a second sequence herein, the two sequences can be fully complementary, or they may form one or more, but generally not more than 4, 3 or 2 mismatched base pairs upon hybridization, while retaining the ability to hybridize under the conditions most relevant to their ultimate application. However, where two oligonucleotides are designed to form, upon hybridization, one or more single stranded overhangs as is common in double stranded nucleic acid therapeutics, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes described herein.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled. Such non-Watson-Crick base pairs includes, but not limited to, G:U Wobble or Hoogstein base pairing.

The terms "complementary," "fully complementary" and "substantially complementary" herein may be used with respect to the base matching between the sense strand and the antisense strand of a dsRNA, or between an antisense nucleic acid or the antisense strand of dsRNA and a target sequence, as will be understood from the context of their use.

As used herein, a polynucleotide that is "substantially complementary to at least part of" a messenger RNA (mRNA) refers to a polynucleotide that is substantially complementary to a contiguous portion of the mRNA of interest (e.g., an mRNA encoding HSP90, especially HSP90β) including a 5' UTR, an open reading frame (ORF), or a 3' UTR. For example, a polynucleotide is complementary to at least a part of a HSP90, especially HSP90β mRNA if the sequence is substantially complementary to a non-interrupted portion of an mRNA encoding HSP90, especially HSP90β.

Patents directed to antisense nucleic acids, chemical modifications, and therapeutic uses are provided, for example, in U.S. Pat. No. 5,898,031 related to chemically modified RNA-containing therapeutic compounds, and U.S. Pat. No. 6,107,094 related methods of using these compounds as therapeutic agent. U.S. Pat. No. 7,432,250 related to methods of treating patients by administering single-stranded chemically modified RNA-like compounds; and U.S. Pat. No. 7,432,249 related to pharmaceutical compositions containing single-stranded chemically modified RNA-like compounds. U.S. Pat. No. 7,629,321 is related to methods of cleaving target mRNA using a single-stranded oligonucleotide having a plurality RNA nucleosides and at least one chemical modification. Each of the patents listed in the paragraph are incorporated herein by reference.

Therapeutic nucleic acid may include natural (i.e. A, G, U, C, or T) or modified (7-deazaguanosine, inosine, etc.) bases. In addition, the bases in nucleotide may be joined by a linkage other than a phosphodiester bond, so long as it does not interfere with hybridization. Thus, inhibitory nucleic acids may be peptide nucleic acids in which the constituent bases are joined by peptide bonds rather than phosphodiester linkages. The inhibitory nucleic acids may be prepared by converting the RNA to cDNA using known methods (see, e.g., Ausubel et. al., Current Protocols in Molecular Biology Wiley 1999). The inhibitory nucleic acids can also be cRNA (see, e.g., Park et. al, (2004) Biochem. Biophys. Res. Commun. 325(4): 1346-52).

Therapeutic nucleic acids can be produced from synthetic methods such as phosphoramidite methods, H-phosphonate methodology, and phosphite trimester methods. Inhibitory nucleic acids can also be produced by PCR methods. Such methods produce cDNA and cRNA sequences complementary to the mRNA. The method of synthesis of a therapeutic nucleic acid is not a limitation of the invention.

Nucleic acid therapeutics typically include one or more chemical modifications to improve their stability and to modulate their pharmacokinetic and pharmacodynamic properties. For example, the modifications on the nucleotides can include, but are not limited to, LNA, HNA, CeNA, 2'-methoxyethyl, 2'-O-alkyl, 2'-O-allyl, 2'-C— allyl, 2'-fluoro, 2'-deoxy, 2'-hydroxyl, and combinations thereof.

Nucleic acid therapeutics may further comprise at least one phosphorothioate or methylphosphonate internucleotide linkage. The phosphorothioate or methylphosphonate internucleotide linkage modification may occur on any nucleotide of the sense strand or antisense strand or both (in nucleic acid therapeutics including a sense strand) in any position of the strand. For instance, the internucleotide linkage modification may occur on every nucleotide on the sense strand or antisense strand; each internucleotide linkage modification may occur in an alternating pattern on the sense strand or antisense strand; or the sense strand or antisense strand may contain both internucleotide linkage modifications in an alternating pattern. The alternating pattern of the internucleotide linkage modification on the sense strand may be the same or different from the antisense strand, and the alternating pattern of the internucleotide linkage modification on the sense strand may have a shift relative to the alternating pattern of the internucleotide linkage modification on the antisense strand.

Other modifications include the incorporation of modified bases (or modified nucleoside or modified nucleotides) that are variations of standard bases, sugars and/or phosphate backbone chemical structures occurring in ribonucleic (i.e., A, C, G and U) and deoxyribonucleic (i.e., A, C, G and T) acids. Included within this scope are, for example: Gm (2'-methoxyguanylic acid), Am (2'-methoxyadenylic acid), Cf (2'-fluorocytidylic acid), Uf (2'-fluorouridylic acid), Ar (riboadenylic acid). The aptamers may also include cytosine or any cytosine-related base including 5-methylcytosine, 4-acetylcytosine, 3-methylcytosine, 5-hydroxymethyl cytosine, 2-thiocytosine, 5-halocytosine (e.g., 5-fluorocytosine, 5-bromocytosine, 5-chlorocytosine, and 5-iodocytosine), 5-propynyl cytosine, 6-azocytosine, 5-trifluoromethylcytosine, N4, N4-ethanocytosine, phenoxazine cytidine, phenothiazine cytidine, carbazole cytidine or pyridoindole cytidine. The aptamer may further include guanine or any guanine-related base including 6-methylguanine, 1-methylguanine, 2,2-dimethylguanine, 2-methylguanine, 7-methylguanine, 2-propylguanine, 6-propylguanine, 8-haloguanine (e.g., 8-fluoroguanine, 8-bromoguanine, 8-chloroguanine, and 8-iodoguanine), 8-aminoguanine, 8-sulfhydrylguanine, 8-thioalkylguanine, 8-hydroxylguanine, 7-methylguanine, 8-azaguanine, 7-deazaguanine or 3-deazaguanine. The aptamer may still further include adenine or any adenine-related base including 6-methyladenine, N6-isopentenyladenine, N6-methyladenine, 1-methyladenine, 2-methyladenine, 2-methylthio-N6-isopentenyladenine, 8-haloadenine (e.g., 8-fluoroadenine, 8-bromoadenine, 8-chloroadenine, and 8-iodoadenine), 8-aminoadenine, 8-sulfhydryladenine, 8-thioalkyladenine, 8-hydroxyladenine, 7-methyladenine, 2-haloadenine (e.g., 2-fluoroadenine, 2-bromoadenine, 2-chloroadenine, and 2-iodoadenine), 2-aminoadenine, 8-azaadenine, 7-deazaadenine or 3-deazaadenine. Also included are uracil or any uracil-related base including 5-halouracil (e.g., 5-fluorouracil, 5-bromouracil, 5-chlorouracil, 5-iodouracil), 5-(carboxyhydroxylmethyl)uracil, 5-carboxymethylaminomethyl-2-thiouracil, 5-carboxymethylaminomethyluracil, dihydrouracil, 1-methylpseudouracil, 5-methoxyaminomethyl-2-thiouracil, 5'-methoxycarbonylmethyluracil, 5-methoxyuracil, 5-methyl-2-thiouracil, 2-thiouracil, 4-thiouracil, 5-methyluracil, uracil-5-oxyacetic acid methylester, uracil-5-oxyacetic acid, pseudouracil, 5-methyl-2-thiouracil, 2-thiouracil, 3-(3-amino-3-N2-carboxypropyl)uracil, 5-methylaminomethyluracil, 5-propynyl uracil, 6-azouracil, or 4-thiouracil.

Examples of other modified base variants known in the art include, without limitation, e.g., 4-acetylcytidine, 5-(carboxyhydroxylmethyl) uridine, 2'-methoxycytidine, 5-carboxymethylaminomethyl-2-thioridine, 5-carboxymethylaminomethyluridine, dihydrouridine, 2'-O-methylpseudouridine, b-D-galactosylqueosine, inosine, N6-isopentenyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, b-D-mannosylqueosine, 5-methoxycarbonylmethyluridine, 5-methoxyuridine, 2-methylthio-N6-isopentenyladenosine, N-((9-b-D-ribofuranosyl-2-methylthiopurine-6-yl)carbamoyl)threonine, N-((9-b-D-ribofuranosylpurine-6-yl)N-methyl-carbamoyl) threonine, urdine-5-oxyacetic acid methylester, uridine-5-oxyacetic acid (v), wybutoxosine, pseudouridine, queosine, 2-thiocytidine, 5-methyl-2-thiouridine, 2-thiouridine, 4-thiouridine, 5-methyluridine, N-((9-b-D-ribofuranosylpurine-6-yl)carbamoyl)threonine, 2'-O-methyl-5-methyluridine, 2'-O-methyluridine, and wybutosine, 3-(3-amino-3-carboxypropyl)uridine.

Also included are the modified nucleobases described in U.S. Pat. Nos. 3,687,808, 3,687,808, 4,845,205, 5,130,302, 5,134,066, 5,175,273, 5,367,066, 5,432,272, 5,457,187, 5,459,255, 5,484,908, 5,502,177, 5,525,711, 5,552,540, 5,587,469, 5,594,121, 5,596,091, 5,614,617, 5,645,985, 5,830,653, 5,763,588, 6,005,096, and 5,681,941, each of which is incorporated herein by reference in its entirety. Examples of modified nucleoside and nucleotide sugar backbone variants known in the art include, without limitation, those having, e.g., 2' ribosyl substituents such as F, SH, $SCH_3$, $OCN$, Cl, Br, CN, $CF_3$, $OCF_3$, $SOCH_3$, $SO_2$, $CH_3$, $ONO_2$, $NO_2$, $N_3$, $NH_2$, $OCH_2CH_2OCH_3$, $O(CH_2)_2ON(CH_3)_2$, $OCH_2OCH_2N(CH_3)_2$, $O(C_{1-10}$ alkyl), $O(C_{2-10}$ alkenyl), $O(C_{2-10}$ alkynyl), $S(C_{1-10}$ alkyl), $S(C_{2-10}$ alkenyl), S(C2-10 alkynyl), NH(C1-10 alkyl), $NH(C_{2-10}$ alkenyl), NH(C2-10 alkynyl), and O-alkyl-O-alkyl. Desirable 2' ribosyl substituents include 2'-methoxy(2'-$OCH_3$), 2'-aminopropoxy (2' $OCH_2CH_2CH_2NH_2$), 2'-O-allyl (2'-$CH_2$—CH=$CH_2$), 2'-O-allyl (2'-O—$CH_2$—CH=$CH_2$), 2'-amino (2'-$NH_2$), and 2'-fluoro (2'-F). The 2'-substituent may be in the arabino (up) position or ribo (down) position.

A. Single Stranded Nucleic Acid Therapeutics

Antisense nucleic acid therapeutic agents are single stranded nucleic acid therapeutics, typically about 16 to 30 nucleotides in length, and are complementary to a target nucleic acid sequence in the target cell, either in culture or in an organism.

In another aspect, the agent is a single-stranded antisense RNA molecule. An antisense RNA molecule is complementary to a sequence within the target mRNA. Antisense RNA can inhibit translation in a stoichiometric manner by base pairing to the mRNA and physically obstructing the translation machinery, see Dias, N. et al., (2002) *Mol Cancer Ther* 1:347-355. The antisense RNA molecule may have about 15-30 nucleotides that are complementary to the target mRNA. For example, the antisense RNA molecule may have a sequence of at least 15, 16, 17, 18, 19, 20 or more contiguous nucleotides that are complementary to the target mRNA.

Patents directed to antisense nucleic acids, chemical modifications, and therapeutic uses are provided, for example, in U.S. Pat. No. 5,898,031 related to chemically modified RNA-containing therapeutic compounds, and U.S. Pat. No. 6,107,094 related methods of using these compounds as therapeutic agent. U.S. Pat. No. 7,432,250 related to methods of treating patients by administering single-stranded chemically modified RNA-like compounds; and U.S. Pat. No. 7,432,249 related to pharmaceutical compositions containing single-stranded chemically modified RNA-like compounds. U.S. Pat. No. 7,629,321 is related to methods of cleaving target mRNA using a single-stranded oligonucleotide having a plurality RNA nucleosides and at least one chemical modification. The entire contents of each of the patents listed in this paragraph are incorporated herein by reference.

B. Double Stranded Nucleic Acid Therapeutics

Nucleic acid therapeutic agents of the invention also include double stranded nucleic acid therapeutics. An "RNAi agent," "double stranded RNAi agent," double-stranded RNA (dsRNA) molecule, also referred to as "dsRNA agent," "dsRNA", "siRNA", "iRNA agent," as used interchangeably herein, refers to a complex of ribonucleic acid molecules, having a duplex structure comprising two anti-parallel and substantially complementary, as defined below, nucleic acid strands. As used herein, an RNAi agent can also include dsiRNA (see, e.g., US Patent publication 20070104688, incorporated herein by reference). In general, the majority of nucleotides of each strand are ribonucleotides, but as described herein, each or both strands can also include one or more non-ribonucleotides, e.g., a deoxyribonucleotide and/or a modified nucleotide. In addition, as used in this specification, an "RNAi agent" may include ribonucleotides with chemical modifications; an RNAi agent may include substantial modifications at multiple nucleotides. Such modifications may include all types of modifications disclosed herein or known in the art. Any such modifications, as used in a siRNA type molecule, are encompassed by "RNAi agent" for the purposes of this specification and claims.

The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the dsRNA minus any overhangs that are present in the duplex. In addition to the duplex structure, an RNAi agent may comprise one or more nucleotide overhangs. The term "siRNA" is also used herein to refer to an RNAi agent as described above.

In many embodiments, the duplex region is 15-30 nucleotide pairs in length. In some embodiments, the duplex region is 17-23 nucleotide pairs in length, 17-25 nucleotide pairs in length, 23-27 nucleotide pairs in length, 19-21 nucleotide pairs in length, or 21-23 nucleotide pairs in length.

In certain embodiments, each strand has 15-30 nucleotides.

The RNAi agents that are used in the methods of the invention include agents with chemical modifications as disclosed, for example, in U.S. Provisional Application No. 61/561,710, filed on Nov. 18, 2011, International Application No. PCT/US2011/051597, filed on Sep. 15, 2010, and PCT Publication WO 2009/073809, the entire contents of each of which are incorporated herein by reference. The term "antisense strand" refers to the strand of a double stranded RNAi agent which includes a region that is substantially complementary to a target sequence (e.g., a human TTR mRNA). As used herein, the term "region complementary to part of an mRNA encoding transthyretin" refers to a region on the antisense strand that is substantially complementary to part of a TTR mRNA sequence. Where the region of complementarity is not fully complementary to the target sequence, the mismatches are most tolerated in the terminal regions and, if present, are generally in a terminal region or regions, e.g., within 6, 5, 4, 3, or 2 nucleotides of the 5' and/or 3' terminus.

The term "sense strand," as used herein, refers to the strand of a dsRNA that includes a region that is substantially complementary to a region of the antisense strand.

IV. Diagnostic and Therapeutic Antibodies

Both diagnostic and therapeutic methods of the invention can include the use of antibodies, including polyclonal and monoclonal antibodies. The term "monoclonal antibody" or "monoclonal antibody composition", as used herein, refers to a population of antibody molecules that contain only one species of an antigen binding site capable of immunoreacting with a particular epitope. Antibodies for use in the invention include antibodies that bind to HSP90, preferably antibodies that are HSP90β-specific. Antibodies can be obtained from commercial sources or produced using known methods.

Polyclonal antibodies can be prepared by immunizing a suitable subject with a protein of the invention as an immunogen. The antibody titer in the immunized subject can be monitored over time by standard techniques, such as with an enzyme linked immunosorbent assay (ELISA) using immobilized polypeptide. At an appropriate time after immunization, e.g., when the specific antibody titers are highest, antibody-producing cells can be obtained from the subject and used to prepare monoclonal antibodies (mAb) by standard techniques, such as the hybridoma technique originally described by Kohler and Milstein (1975) *Nature* 256:495-497, the human B cell hybridoma technique (see Kozbor et ah, 1983, *Immunol. Today* 4:72), the EBV-hybridoma technique (see Cole et al., pp. 77-96 In *Monoclonal Antibodies and Cancer Therapy*, Alan R. Liss, Inc., 1985) or trioma techniques. The technology for producing hybridomas is well known (see generally *Current Protocols in Immunology*, Coligan et al. ed., John Wiley & Sons, New York, 1994). Hybridoma cells producing a monoclonal antibody of the invention are detected by screening the hybridoma culture supernatants for antibodies that bind the polypeptide of interest, e.g., using a standard ELISA assay.

Alternative to preparing monoclonal antibody-secreting hybridomas, a monoclonal antibody directed against a protein of the invention can be identified and isolated by screening a recombinant combinatorial immunoglobulin library (e.g., an antibody phage display library) with the polypeptide of interest. Kits for generating and screening phage display libraries are commercially available (e.g., the Pharmacia *Recombinant Phage Antibody System*, Catalog No. 27-9400-01; and the Stratagene *SurfZAP Phage Display Kit*, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) *Bio/Technology* 9:1370-1372; Hay et al. (1992) *Hum. Antibod. Hybridomas* 3:81-85; Huse et al. (1989) Science 246:1275-1281; Griffiths et al. (1993) *EMBO J.* 12:725-734.

Recombinant antibodies that specifically bind a protein of interest can also be used in the methods of the invention. In preferred embodiments, the recombinant antibodies specifically binds a protein of interest or fragment thereof. Recombinant antibodies include, but are not limited to, chimeric and humanized monoclonal antibodies, comprising both human and non-human portions, single-chain antibodies and multi-specific antibodies. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816,397, which are incorporated herein by reference in their entirety.) Single-chain antibodies have an antigen binding site and consist of a single polypeptide. They can be produced by techniques known in the art, for example using methods described in Ladner et. al U.S. Pat. No. 4,946,778 (which is incorporated herein by reference in its entirety); Bird et al., (1988) *Science* 242: 423-426; Whitlow et al., (1991) *Methods in Enzymology* 2:1-9; Whitlow et al., (1991) *Methods in Enzymology* 2:97-105; and Huston et al., (1991) *Methods in Enzymology Molecular Design and Modeling: Concepts and Applications* 203:46-88. Multi-specific antibodies are antibody molecules having at least two antigen-binding sites that specifically bind different antigens. Such molecules can be produced by techniques known in the art, for example using methods described in Segal, U.S. Pat. No. 4,676,980 (the disclosure of which is incorporated herein by reference in its entirety); Holliger et al., (1993) *Proc. Natl. Acad. Sci. USA* 90:6444-6448; Whitlow et al., (1994) *Protein Eng.* 7:1017-1026 and U.S. Pat. No. 6,121,424.

Humanized antibodies are antibody molecules from non-human species having one or more complementarity determining regions (CDRs) from the non-human species and a framework region from a human immunoglobulin molecule. (See, e.g., Queen, U.S. Pat. No. 5,585,089, which is incorporated herein by reference in its entirety.) Humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Cancer Res.* 47:999-1005; Wood et al. (1985) *Nature* 314:446-449; and Shaw et al. (1988) *J. Natl. Cancer Inst.* 80:1553-1559); Morrison (1985) *Science* 229:1202-1207; Oi et al. (1986) *Bio/Techniques* 4:214; U.S. Pat. No. 5,225,539; Jones et al. (1986) *Nature* 321:552-525; Verhoeyan et al. (1988) *Science* 239: 1534; and Beidler et al. (1988) *J. Immunol.* 141:4053-4060.

More particularly, humanized antibodies can be produced, for example, using transgenic mice which are incapable of expressing endogenous immunoglobulin heavy and light chains genes, but which can express human heavy and light chain genes. The transgenic mice are immunized in the normal fashion with a selected antigen, e.g., all or a portion of a polypeptide corresponding to a marker of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995) *Int. Rev. Immunol.* 13:65-93). For a detailed discussion of this technology for producing human antibodies and human monoclonal antibodies and protocols for producing such antibodies, see, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806. In addition, companies can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a murine antibody, is used to guide the selection of a completely human antibody recognizing the same epitope (Jespers et al., 1994, Bio/technology 12:899-903).

The antibodies of the invention can be isolated after production (e.g., from the blood or serum of the subject) or synthesis and further purified by well-known techniques. For example, IgG antibodies can be purified using protein A chromatography. Antibodies specific for a protein of the invention can be selected or (e.g., partially purified) or purified by, e.g., affinity chromatography. For example, a recombinantly expressed and purified (or partially purified) protein of the invention is produced as described herein, and covalently or non-covalently coupled to a solid support such as, for example, a chromatography column. The column can then be used to affinity purify antibodies specific for the proteins of the invention from a sample containing antibodies directed against a large number of different epitopes, thereby generating a substantially purified antibody composition, i.e., one that is substantially free of contaminating antibodies. By a substantially purified antibody composition is meant, in this context, that the antibody sample contains at most only 30% (by dry weight) of contaminating antibodies directed against epitopes other than those of the desired protein of the invention, and preferably at most 20%, yet more preferably at most 10%, and most preferably at most 5% (by dry weight) of the sample is contaminating antibodies. A purified antibody composition means that at least 99% of the antibodies in the composition are directed against the desired protein of the invention.

An antibody directed against a protein can be used to isolate the protein by standard techniques, such as affinity chromatography or immunoprecipitation. Moreover, such an antibody can be used to detect the marker protein, e.g., HSP90β, or fragment thereof (e.g., in a cellular lysate or cell supernatant) in order to evaluate the level and pattern of expression of the marker. The antibodies can also be used diagnostically to monitor protein levels in tissues or body fluids (e.g. in disease state or toxicity state associated body fluid) as part of a clinical testing procedure, e.g., to, for example, determine the efficacy of a given treatment regimen. Detection can be facilitated by the use of an antibody derivative, which comprises an antibody of the invention coupled to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibodies may also be used as therapeutic agents in treating metabolic syndrome and/or diabetes.

V. Small Molecule Inhibitors of HSP90

Small molecule inhibitors of HSP90 include, but are not limited to, geldanamycin (GM) analog (e.g., IPI-493

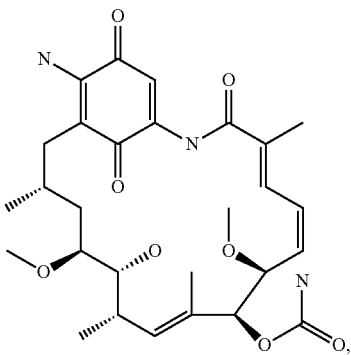 [SMILES: CO[C@H]1/C=C\C=C(/C)C(=O)NC2=CC(=O)C(N)=C(C[C@@H](C)C[C@H](OC)[C@H](O)[C@@H](C)/C=C(\C)[C@@H]1OC(N)=O)C2=O]

IPI-504

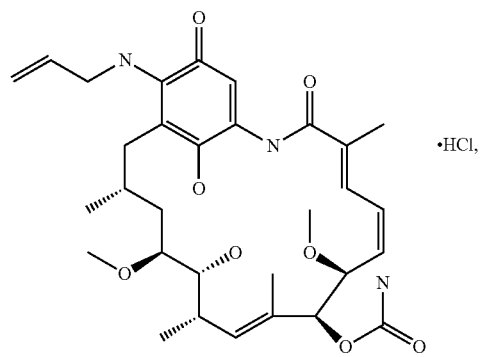

17-AAG (tanespimycin)

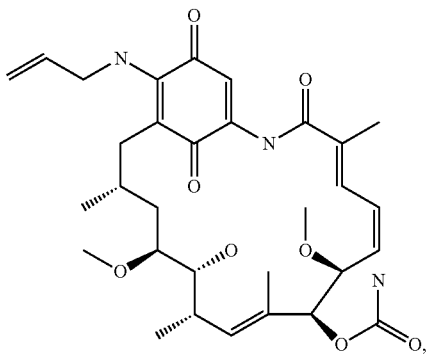 [SMILES: C=CCNC1=C2C[C@@H](C)C[C@H](OC)[C@H](O)[C@@H](C)/C=C(\C)[C@H](OC(N)=O)[C@@H](OC)/C=C\C=C(/C)C(=O)NC(=CC1=O)C2=O]

and 17-DMAG
(alvespimycin)
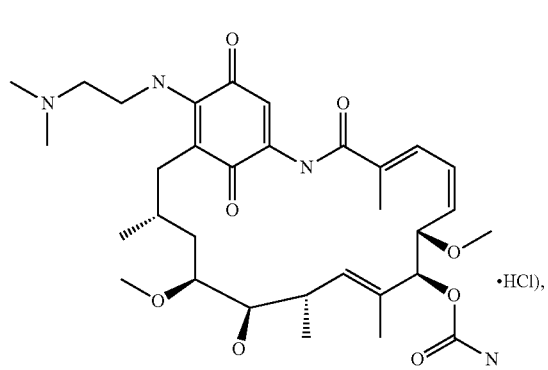 [SMILES: CO[C@H]1/C=C\C=C(/C)C(=O)NC2=CC(=O)C(NCCN(C)C)=C(C[C@@H](C)C[C@H](OC)[C@H](O)[C@@H](C)/C=C(\C)[C@@H]1OC(N)=O)C2=O]
·HCl),
macbecin analog (e.g., BC-274
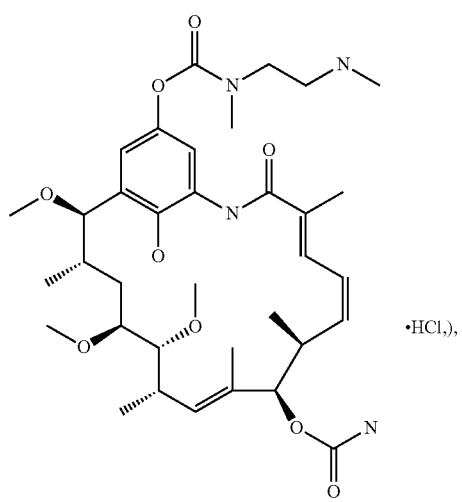
·HCl,),
tripterin (celastrol)
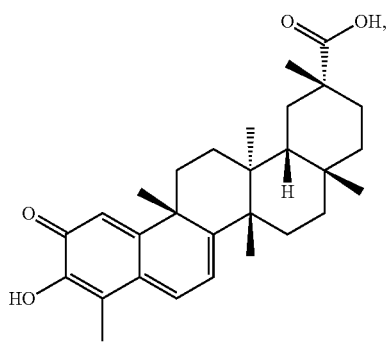
radicicol analog (e.g., KF-55823
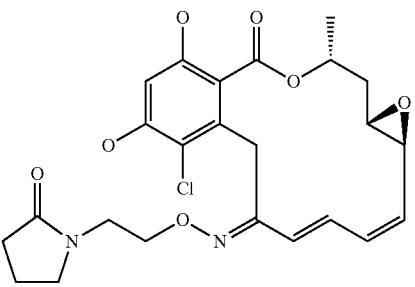 [SMILES: C[C@@H]1C[C@@H]2O[C@H]2\C=C/C=C/C(=N/OCCN2CCCC2=O)Cc2c(Cl)c(O)cc(O)c2C(=O)O1]
and KF-58333
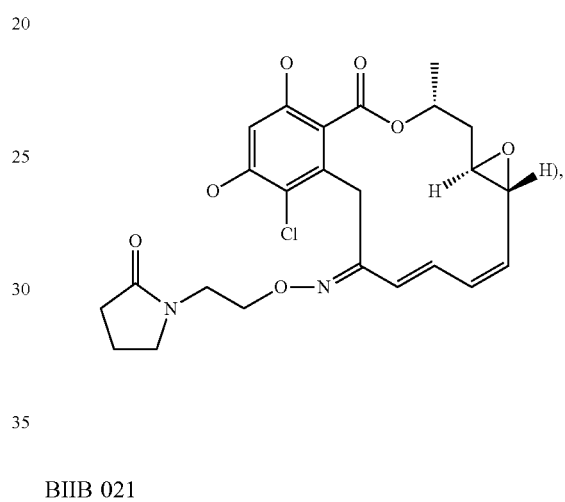
BIIB 021
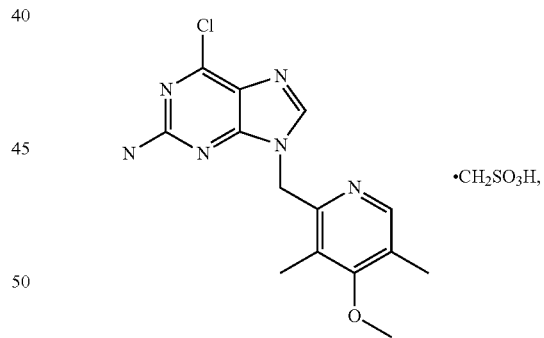
·CH₂SO₃H,
BIIB-028, PU-H64
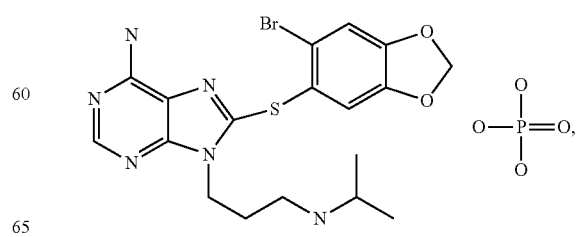

PU-H71
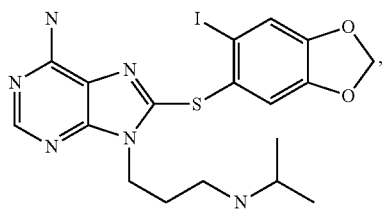 [SMILES: CC(C)NCCCn1c(Sc2cc3c(cc2I)OCO3)nc2c(N)ncnc21]
PU-DZ8
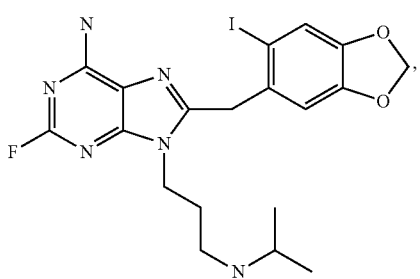 [SMILES: CC(C)NCCCn1c(Cc2cc3c(cc2I)OCO3)nc2c(N)nc(F)nc21]
PU-HZ151
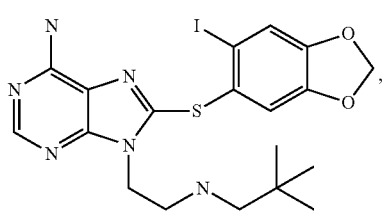 [SMILES: CC(C)(C)CNCCn1c(Sc2cc3c(cc2I)OCO3)nc2c(N)ncnc21]
PU-DZ13
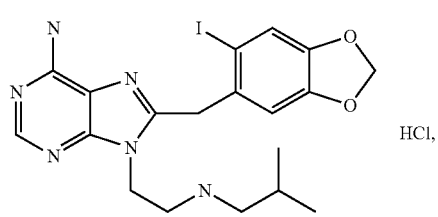 [SMILES: CC(C)CNCCn1c(Cc2cc3c(cc2I)OCO3)nc2c(N)ncnc21] HCl,
SNX-2112
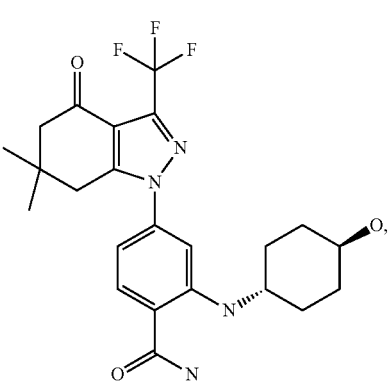
SNX-5422
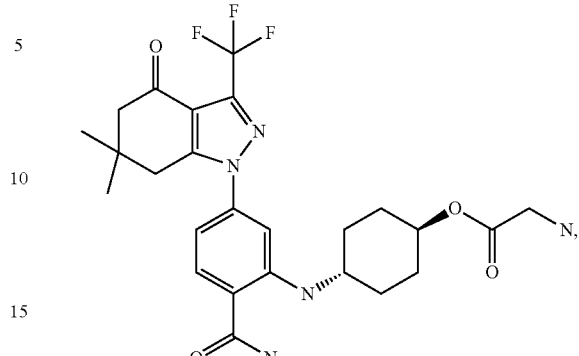
SNX-2321
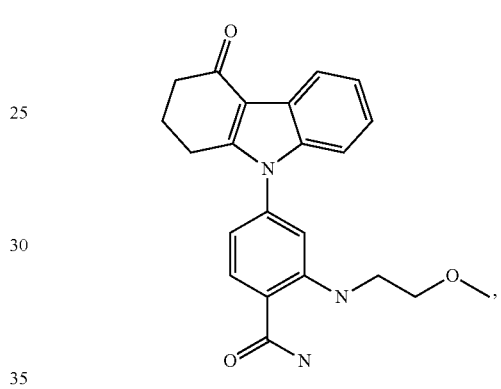
SNX-7081
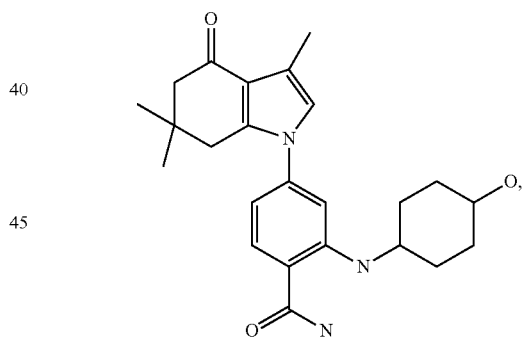
SNX-8891, SNX-0723
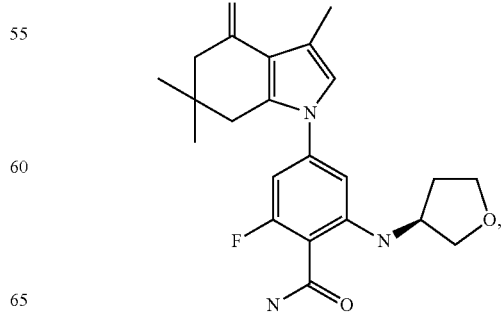

33
SAR-567530, ABI-287, ABI-328, AT-13387
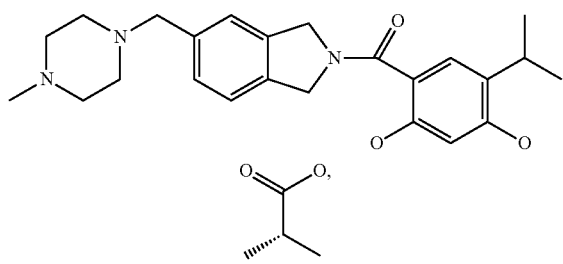
NSC-113497
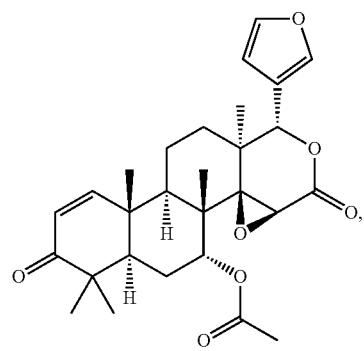
PF-3823863
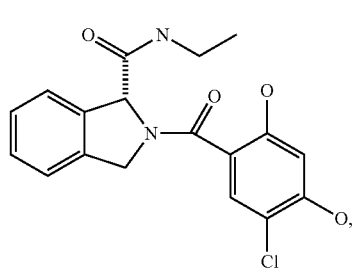
PF-4470296
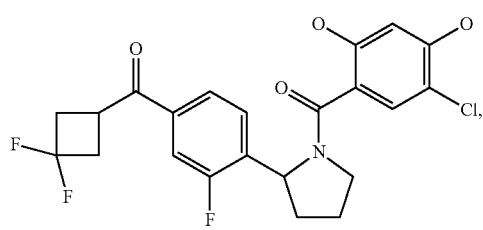 [SMILES: O=C(c1ccc(C2CCCN2C(=O)c2cc(Cl)c(O)cc2O)c(F)c1)C1CC(F)(F)C1]
EC-102, EC-154, ARQ-250-RP, VER-50589
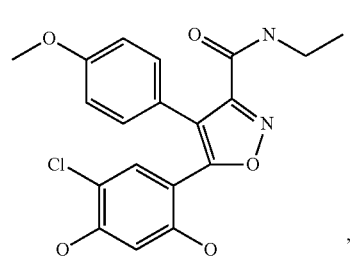 [SMILES: CCNC(=O)c1noc(-c2cc(Cl)c(O)cc2O)c1-c1ccc(OC)cc1]
34
VER-51047
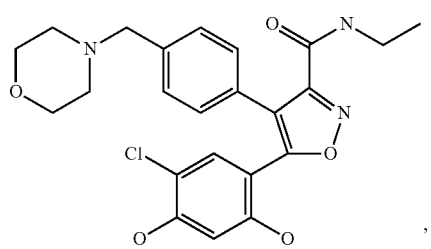 [SMILES: CCNC(=O)c1noc(-c2cc(Cl)c(O)cc2O)c1-c1ccc(CN2CCOCC2)cc1]
VER-82576
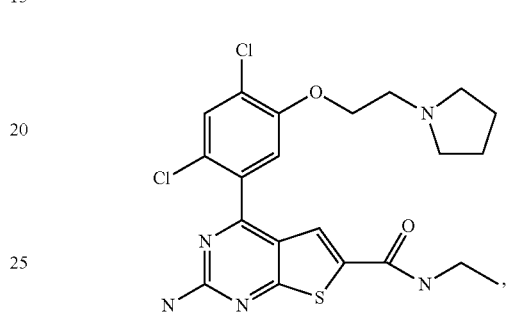
VER-82160
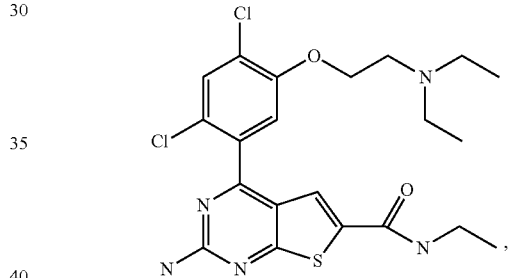
KW-2478
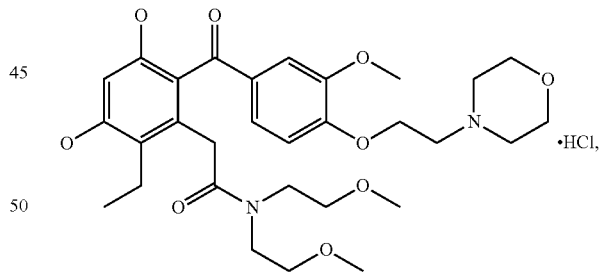
BHI-001, AUY-922
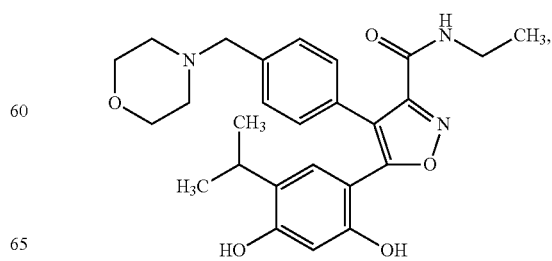

EMD-614684
CH-5164840
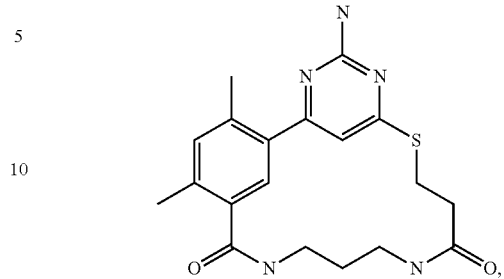
EMD-683671, XL-888
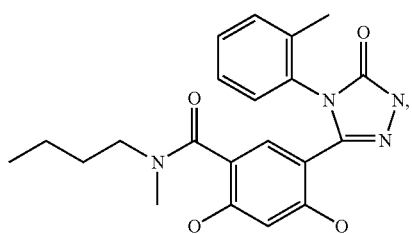
NXD-30001
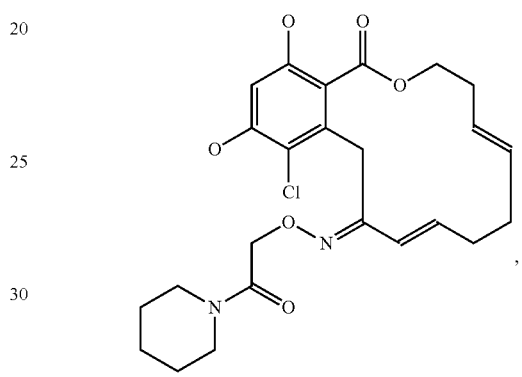
KOS-2484, KOS-2539, CUDC-305
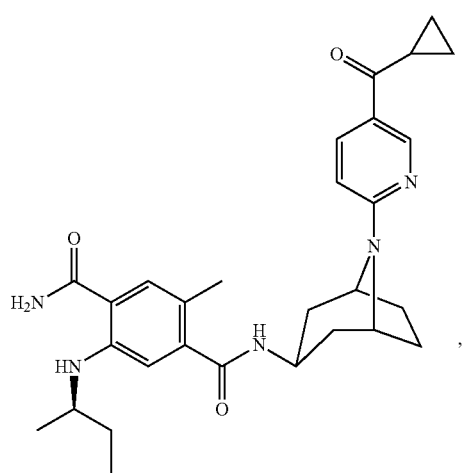 [SMILES: CC[C@@H](C)Nc1cc(C(=O)NC2CC3CCC(C2)N3c2ccc(C(=O)C3CC3)cn2)c(C)cc1C(N)=O]
NVP-HSP990
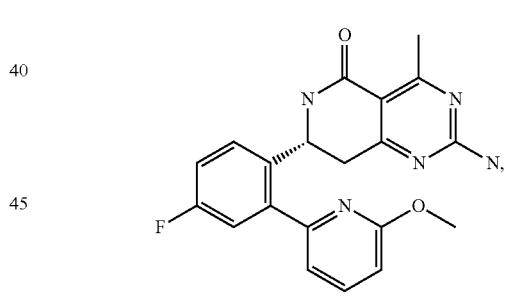
MPC-3100
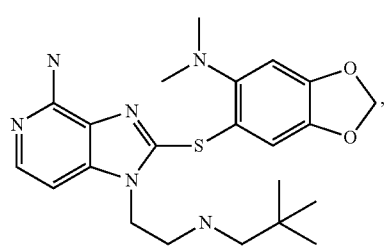 [SMILES: CN(C)c1cc2c(cc1Sc1nc3c(N)nccc3n1CCNCC(C)(C)C)OCO2]
SST-0201CL1
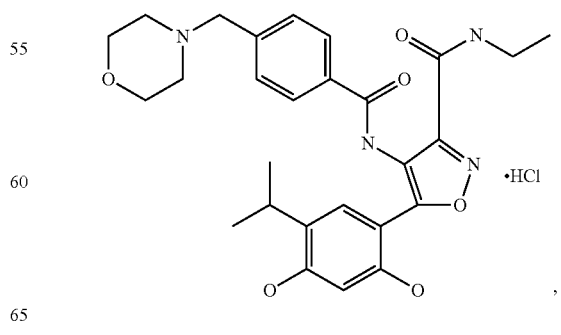
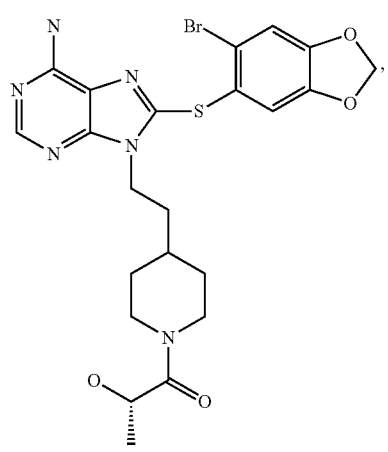 [SMILES: C[C@H](O)C(=O)N1CCC(CCn2c(Sc3cc4c(cc3Br)OCO4)nc3c(N)ncnc32)CC1]

SST-0115AA1
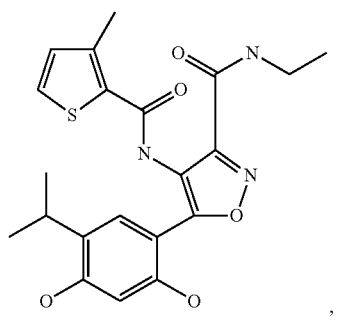 [SMILES: CCNC(=O)c1noc(-c2cc(C(C)C)c(O)cc2O)c1NC(=O)c1sccc1C]
CCT018059, KU32
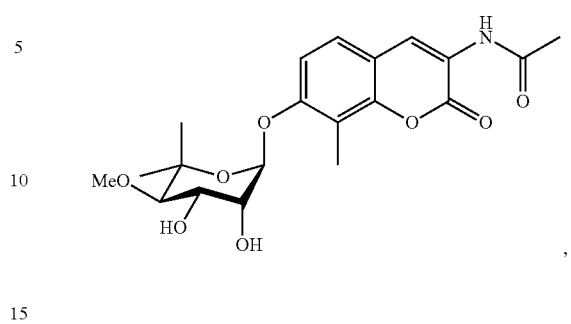
SST-0221AA1
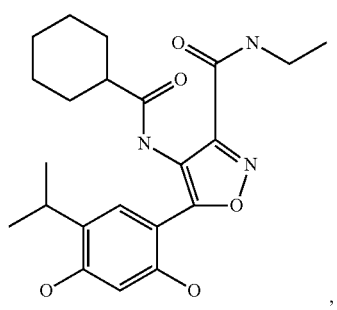 [SMILES: CCNC(=O)c1noc(-c2cc(C(C)C)c(O)cc2O)c1NC(=O)C1CCCCC1]
KU135,
SST-0223AA1
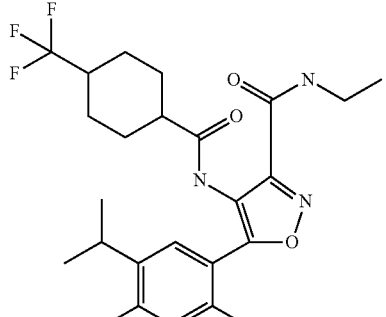
KU174
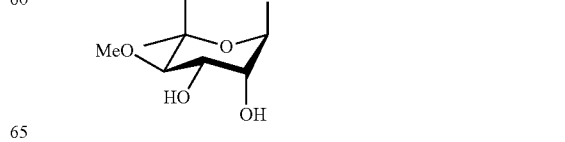
novobiocin (a C-terminal Hsp90i), herbinmycin A, ganetespib
A4
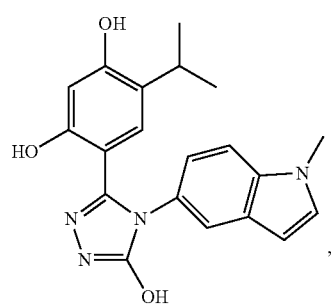

A4Dimer

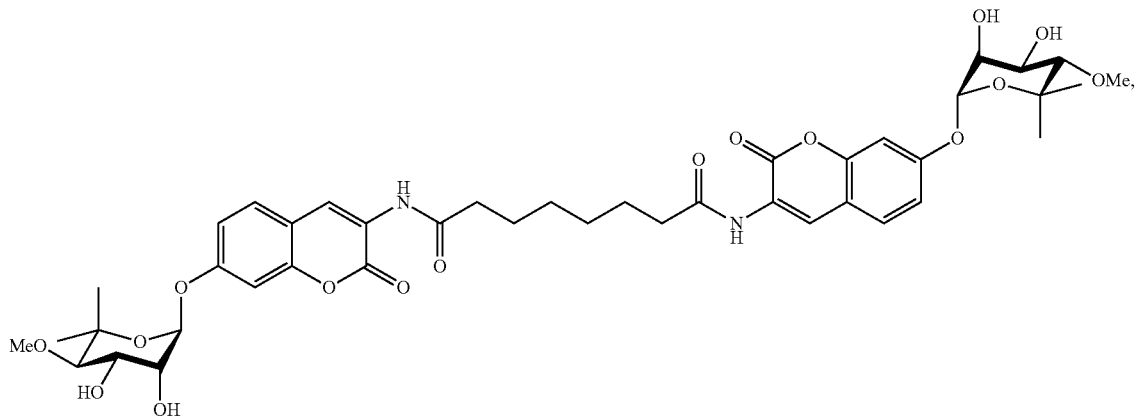

coumermycin, Gedunin, gamendazole

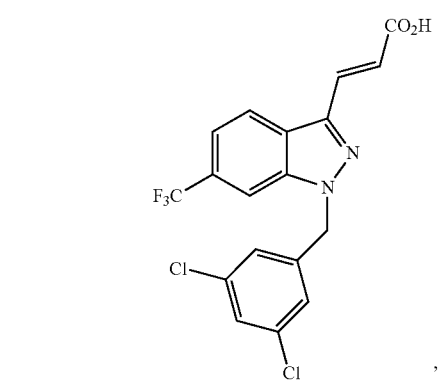 [SMILES: O=C(O)/C=C/c1nn(Cc2cc(Cl)cc(Cl)c2)c2cc(C(F)(F)F)ccc12]

or H2-gamendazole

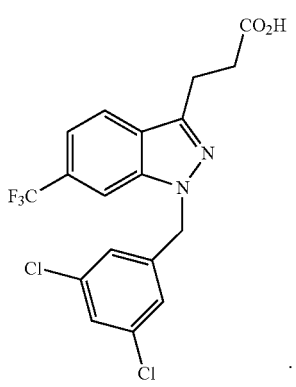

Depending on their mechanism of action, some small molecule inhibitors preferably inhibit HSP90 by interfering with the binding and/or hydrolysis of ATP at the N-terminal ATP-bindind domain, e.g., geldanamycin (see Sausville, et al., Annu Rev Pharmacol Toxicol 2003; 43: 199-231, incorporated herein by reference). Other HSP90 inhibitors inhibit HSP90 by interfering with the binding and/or hydrolysis of ATPat the C-terminal ATP-binding domain, e.g., novobiocin (see Marcu, et al., J Biol Chem 2000; 275: 37181-37186, incorporated herein by reference). Not all HSP90 inhibitors act on HSP90 by interacting with the ATP-binding site at either terminus of Hsp90 protein, Examples of those HSP90 inhibitors include KU174, coumermycin A1, celastrol, gedunin, H2-gamendazole, and gamendazole (see Matts, et al., Bioorganic & Medicinal Chemistry 19 (2011) 684-692 and Tash, et al., Biology of Reproduction 2008; 78, 1139-1152, incorporated herein by reference). Among these inhibitors, for example, celastrol disrupts interaction between Hsp90 and the kinase co-chaperone Cdc37 to effectively disable Hsp90 (see Matts, et al, Bioorganic & Medicinal Chemistry 19 (2011) 684-692, incorporated herein by reference).

Many known HSP 90 inhibitors inhibit both the HSP90α and HSP90β isoforms, e.g., geldanamycin and NVP-HS990. Others inhibitors show a preference for one of the two isotypes, such as gamendazole and H2-gamendazole, which are specific for HSP90β (see Tash, et al., Biology of Reproduction 2008; 78, 1139-1152). In addition, HSP90β is more sensitive to radicicol than HSP90α (see Millson et al, FEBS J 2007; 274, 4453-4463, incorporated herein by reference). Additionally, novel inhibitors that are specific for HSP90β can be selected from known HSP90β inhibitors or developed by the skilled artisan by modifying the known specific inhibitors, such as gamendazole, or by designing inhibitors based on the binding domain determined by co-crystalography of HSP90β and an HSP90β-specific inhibitor, e.g., gamendazol.

The above-mentioned gamendazole, an HSP90β-specific inhibitor, is an analogue of lonidamine. Lonidamine analogs are known in the art. Some non-limiting examples of lonidamine analogues are described in WO2006/023704 and WO2011/005759 (the entire contents of both of which are incorporated herein by reference) and represented by the following formula:

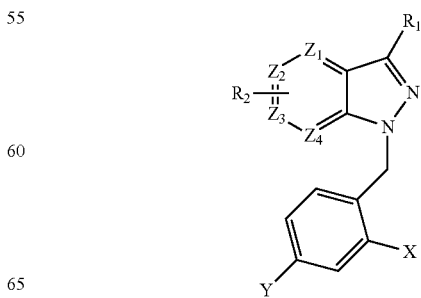

Wherein $R_1$ is carboxyl,

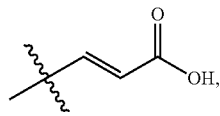 [SMILES: */C=C/C(=O)O]

or carboxylic acid hydrazide;
wherein $R_2$ is hydrogen, halogen, alcohol, alkyl, alkoxy, aralkyl, cycloalkyl, haloalkyl, haloalkoxy, amino, or carboxyl;
wherein X and Y are the same or different from each other and are halogen or lower alkyl;
wherein $Z_1$, $Z_2$, $Z_3$, and $Z_4$ are independently nitrogen or carbon; and pharmaceutically acceptable salts and esters thereof.

Examples of such lonidamine analogues include,
6-chloro-1-(2,4-dichlorobenzyl)-1H-indazole-3-carboxylic acid hydrazide;
1-(2,4-dichlorobenzyl)-6-fluoro-1H-indazole-3-carboxylic acid methyl ester;
6-fluoro-1-(2,4-dichlorobenzyl)-1H-indazole-3-carboxylic acid hydrazide;
3-[1-(2,4-dichlorobenzyl)-6-fluoro-1H-indazol-3-yl]-acrylic acid;
3-[1-(2,4-dichlorobenzyl)-6-chloro-1H-indazol-3-yl]-acrylic acid;
3-[1-(2,4-dichlorobenzyl)-6-trifluoromethoxy-1H-indazol-3-yl]acrylic acid;
3-[1-(2,4-dichlorobenzyl)-6-chloro-1H-indazol-3-yl]-propionic acid;
3-[1-(2,4-dichlorobenzyl)-6-methyl-1H-indazol-3-yl]acrylic acid (TH 2-192);
1-(2,4-dichlorobenzyl)-6-methyl-1H-indazole-3-carboxylic acid (TH 2-178);
1-(2,4-dichlorobenzyl)-6-methyl-1H-indazole-3-carboxylic acid hydrazide (TH 2-179);
3-[1-(2,4-dichlorobenzyl)-6-chloro-1H-indazol-3-yl]-acrylic acid (JWS 1-190);
1-(2-chloro-4-fluorobenzyl)-6-chloro-1H-indazole-3-carboxylic acid hydrazide (JWS 2-22); and
1-(2,4-difluorobenzyl)-6-chloro-1H-indazole-3-carboxylic acid hydrazide (JWS 1-282).

Additional lonidamine analogues are further described in WO2006/015263 and WO2006/015191 and also in Mok et al, Reproduction, 2011, 141, 571-580 (each of which is incorporated herein by reference). Examples of such lonidamine analogues include lonidamin, Adjudin (AF-2364), AF2785, and CDB-4022.

Some analogues of coumermycin and coumermycin A1 are described in WO2001/87309 and WO2012/162054 (both of which is incorporated herein by reference), in which a cumermycin analog is represented by the following formula:

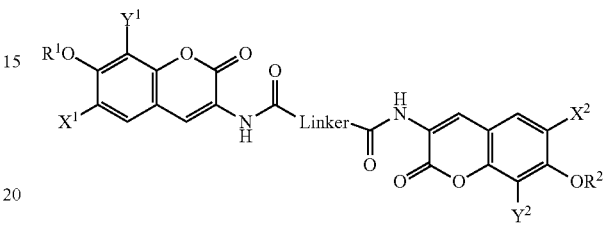

wherein:
$R^1$, $R^2$, $X^1$, $X^2$, $Y^1$ and $Y^2$ includes a moiety independently selected from hydrogen, halogens, hydroxyls, alkoxys, straight aliphatics, branched aliphatics, cyclic aliphatics, heterocyclic aliphatics, substituted aliphatics, unsubstituted aliphatics, saturated aliphatics, unsaturated aliphatics, aromatics, polyaromatics, substituted aromatics, hetero-aromatics, amines, primary amines, secondary amines, tertiary amines, aliphatic amines, carbonyls, carboxyls, amides, esters, amino acids, peptides, polypeptides, sugars, sugar mimics, derivatives thereof, or combinations thereof, the aliphatic groups having carbon chains of about 0-20 carbons or hetero atoms or O, N, S, or P; and linker including a straight aliphatic, branched aliphatic, cyclic aliphatic, heterocyclic aliphatic, substituted aliphatic, unsubstituted aliphatic, saturated aliphatic, unsaturated aliphatic, aromatic, polyaromatic, substituted aromatic, heteroaromatic, amine, primary amine, secondary amine, tertiary amine, aliphatic amine, carbonyl, carboxyl, amide, ester, amino acid, peptide, polypeptide, sugars, sugar mimic, derivatives thereof, or combinations thereof.

Examples of the coumermycin analogs are represented by the following formula:

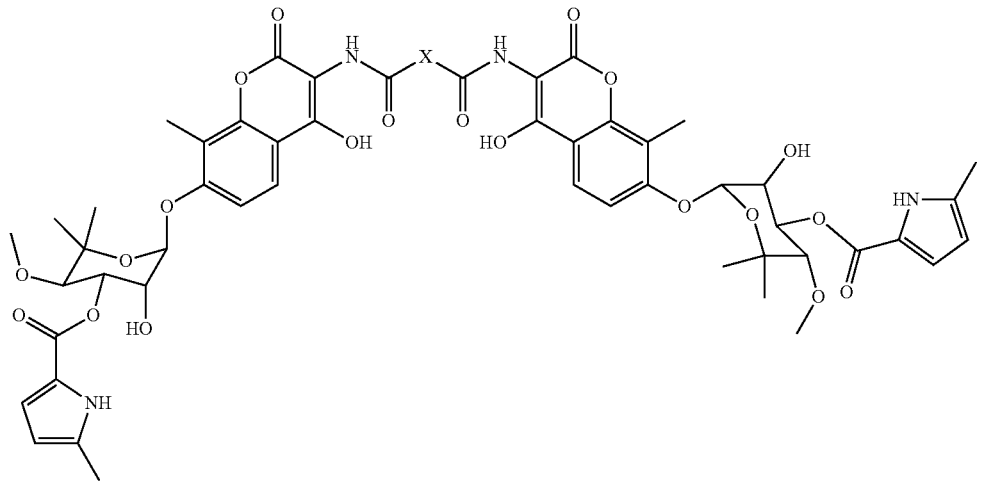

wherein X is a linker containing from about 1 to about 54 atoms that connects the two halves of the molecule.

Some analogues of celastrol and gendunin are described in WO2007/117466 (which is incorporated herein by reference). In certain embodiments, the small molecule inhibitors of HSP90 inhibit HSP90β. In certain embodiments, the small molecule inhibitors of HSP90 specifically inhibit HSP90β.

VI. Diagnostic Methods for Metabolic Syndrome

The invention further provides methods of identifying a subject as having or being at risk of having metabolic syndrome and/or diabetes comprising detecting the level of expression of a marker protein and/or a nucleic acid in a sample from the subject.

An exemplary method for detecting the presence or absence of a marker protein or nucleic acid in a biological sample, e.g., HSP90, particularly HSP90β, involves obtaining a biological sample (e.g. tissue sample) from a test subject and contacting the biological sample with a compound or an agent capable of detecting the polypeptide or nucleic acid (e.g., mRNA, genomic DNA, or cDNA). The detection methods of the invention can thus be used to detect mRNA, protein, cDNA, or genomic DNA, for example, in a biological sample in vitro as well as in vivo for the diagnosis of metabolic syndrome. For example, in vitro techniques for detection of mRNA include northern hybridizations and in situ hybridizations. In vitro techniques for detection of a marker protein include enzyme linked immunosorbent assays (ELISAs), western blots, immunoprecipitations and immunofluorescence. In vitro techniques for detection of genomic DNA include Southern hybridizations. In vivo techniques for detection of mRNA include polymerase chain reaction (PCR), northern hybridizations and in situ hybridizations. Furthermore, in vivo techniques for detection of a marker protein include introducing into a subject a labeled antibody directed against the protein or fragment thereof. For example, the antibody can be labeled with a radioactive marker whose presence and location in a subject can be detected by standard imaging techniques.

A general principle of such diagnostic and prognostic assays involves preparing a sample or reaction mixture that may contain a marker, and a probe, under appropriate conditions and for a time sufficient to allow the marker and probe to interact and bind, thus forming a complex that can be removed and/or detected in the reaction mixture. These assays can be conducted in a variety of ways.

For example, one method to conduct such an assay would involve anchoring the marker or probe onto a solid phase support, also referred to as a substrate, and detecting target marker/probe complexes anchored on the solid phase at the end of the reaction. In one embodiment of such a method, a sample from a subject, which is to be assayed for presence and/or concentration of marker, can be anchored onto a carrier or solid phase support. In another embodiment, the reverse situation is possible, in which the probe can be anchored to a solid phase and a sample from a subject can be allowed to react as an unanchored component of the assay.

There are many established methods for anchoring assay components to a solid phase. These include, without limitation, marker or probe molecules which are immobilized through conjugation of biotin and streptavidin. Such biotinylated assay components can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the surfaces with immobilized assay components can be prepared in advance and stored.

Other suitable carriers or solid phase supports for such assays include any material capable of binding the class of molecule to which the marker or probe belongs. Well-known supports or carriers include, but are not limited to, glass, polystyrene, nylon, polypropylene, nylon, polyethylene, dextran, amylases, natural and modified celluloses, polyacrylamides, gabbros, and magnetite.

In order to conduct assays with the above mentioned approaches, the non-immobilized component is added to the solid phase upon which the second component is anchored. After the reaction is complete, uncomplexed components may be removed (e.g., by washing) under conditions such that any complexes formed will remain immobilized upon the solid phase. The detection of marker/probe complexes anchored to the solid phase can be accomplished in a number of methods outlined herein.

In a preferred embodiment, the probe, when it is the unanchored assay component, can be labeled for the purpose of detection and readout of the assay, either directly or indirectly, with detectable labels discussed herein and which are well-known to one skilled in the art.

It is also possible to directly detect marker/probe complex formation without further manipulation or labeling of either component (marker or probe), for example by utilizing the technique of fluorescence energy transfer (see, for example, Lakowicz et ah, U.S. Pat. No. 5,631,169; Stavrianopoulos, et ah, U.S. Pat. No. 4,868,103). A fluorophore label on the first, 'donor' molecule is selected such that, upon excitation with incident light of appropriate wavelength, its emitted fluorescent energy will be absorbed by a fluorescent label on a second 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. A FRET binding event can be conveniently measured through standard fluorometric detection means well known in the art (e.g., using a fluorimeter).

In another embodiment, determination of the ability of a probe to recognize a marker can be accomplished without labeling either assay component (probe or marker) by utilizing a technology such as real-time Biomolecular Interaction Analysis (BIA) (see, e.g., Sjolander, S, and Urbaniczky, C, 1991, *Anal. Chem.* 63:2338-2345 and Szabo et al., 1995, *Curr. Opin. Struct. Biol.* 5:699-705). As used herein, "BIA" or "surface plasmon resonance" is a technology for studying biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

Alternatively, in another embodiment, analogous diagnostic and prognostic assays can be conducted with marker and probe as solutes in a liquid phase. In such an assay, the complexed marker and probe are separated from uncomplexed components by any of a number of standard techniques, including but not limited to: differential centrifugation, chromatography, electrophoresis and immunoprecipitation. In differential centrifugation, marker/probe complexes may be separated from uncomplexed assay components through a series of centrifugal steps, due to the different sedimentation equilibria of complexes based on their different sizes and densities (see, for example, Rivas, G., and Minton, A. P., 1993, *Trends Biochem Sci.* 18(8):284-7). Standard chromatographic techniques may also be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the marker/probe complex as compared to the uncomplexed components may be exploited to differentiate the complex from uncomplexed components, for example through the utilization of ion-exchange chromatography resins. Such resins and chromatographic techniques are well known to one skilled in the art (see, e.g., Heegaard, N. H., 1998, *J. Mol. Recognit. Winter* 11(1-6): 141-8; Hage, D. S., and Tweed, S. A. *J Chromatogr B Biomed Sci Appl* 1997 Oct. 10; 699(1-2):499-525). Gel electrophoresis may also be employed to separate complexed assay components from unbound components (see, e.g., Ausubel et ah, ed., *Current Protocols in Molecular Biology*, John Wiley & Sons, New York, 1987-1999). In this technique, protein or nucleic acid complexes are separated based on size or charge, for example. In order to maintain the binding interaction during the electrophoretic process, non-denaturing gel matrix materials and conditions in the absence of reducing agent are typically preferred. Appropriate conditions to the particular assay and components thereof will be well known to one skilled in the art.

In a particular embodiment, the level of marker mRNA can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from cells (see, e.g., Ausubel et ah, ed., *Current Protocols in Molecular Biology*, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding a marker of the present invention. Other suitable probes for use in the diagnostic assays of the invention are described herein. Hybridization of an mRNA with the probe indicates that the marker in question is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in an Affymetrix gene chip array. A skilled artisan can readily adapt known mRNA detection methods for use in detecting the level of mRNA encoded by the markers of the present invention.

An alternative method for determining the level of mRNA marker in a sample involves the process of nucleic acid amplification, e.g., by RT-PCR (the experimental embodiment set forth in Mullis, 1987, U.S. Pat. No. 4,683,202), ligase chain reaction (Barany, 1991, *Proc. Natl. Acad. Sci. USA*, 88:189-193), self sustained sequence replication (Guatelli et al., 1990, *Proc. Natl. Acad. Sci. USA* 87:1874-1878), transcriptional amplification system (Kwoh et al., 1989, *Proc. Natl. Acad. Sci. USA* 86:1173-1177), Q-Beta Replicase (Lizardi et al, 1988, *Bio/Technology* 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the prior to detection. In such methods, a cell or tissue sample is prepared/processed using known histological methods. The sample is then immobilized on a support, typically a glass slide, and then contacted with a probe that can hybridize to mRNA that encodes the marker.

As an alternative to making determinations based on the absolute expression level of the marker, determinations may be based on the normalized expression level of the marker. Expression levels are normalized by correcting the absolute expression level of a marker by comparing its expression to the expression of a gene that is not a marker, e.g., a housekeeping gene that is constitutively expressed. Suitable genes for normalization include housekeeping genes such as the actin gene, or epithelial cell-specific genes. This normalization allows the comparison of the expression level in one sample, e.g., a patient sample, to another sample, e.g., a non-disease samples from different sources.

Alternatively, the expression level can be provided as a relative expression level. To determine a relative expression level of a marker, the level of expression of the marker is determined for 10 or more samples of normal versus disease cell isolates, preferably 50 or more samples, prior to the determination of the expression level for the sample in question. The mean expression level of each of the genes assayed in the larger number of samples is determined and this is used as a baseline expression level for the marker. The expression level of the marker determined for the test sample (absolute level of expression) is then divided by the mean expression value obtained for that marker. This provides a relative expression level.

Preferably, the samples used in the baseline determination will be from non-disease cells. The choice of the cell source is dependent on the use of the relative expression level. Using expression found in normal tissues as a mean expression score aids in validating whether the marker assayed is disease specific (versus normal cells). In addition, as more data is accumulated, the mean expression value can be revised, providing improved relative expression values based on accumulated data. Expression data from disease cells provides a means for grading the severity of the disease state.

In another embodiment of the present invention, a marker protein, HSP90, preferably HSP90β, is detected. A preferred agent for detecting marker protein of the invention is an antibody capable of binding to such a protein or a fragment thereof, preferably an antibody with a detectable label. Antibodies can be polyclonal, or more preferably, monoclonal. An intact antibody, or a fragment or derivative thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

Proteins from cells can be isolated using techniques that are well known to those of skill in the art. The protein isolation methods employed can, for example, be such as those described in Harlow and Lane (Harlow and Lane, 1988, *Antibodies: A Laboratory Manual*, Cold Spring Harbor Laboratory Press, Cold Spring Harbor, N.Y.).

A variety of formats can be employed to determine whether a sample contains a protein that binds to a given antibody. Examples of such formats include, but are not limited to, enzyme immunoassay (EIA), radioimmunoassay (RIA), western blot analysis and enzyme linked immunoabsorbant assay (ELISA). A skilled artisan can readily adapt known protein/antibody detection methods for use in determining whether cells express a marker of the present invention.

In one format, antibodies, or antibody fragments or derivatives, can be used in methods such as western blots or immunofluorescence techniques to detect the expressed proteins. In such uses, it is generally preferable to immobilize either the antibody or proteins on a solid support. Suitable solid phase supports or carriers include any support capable of binding an antigen or an antibody. Well-known supports or carriers include glass, polystyrene, polypropylene, polyethylene, dextran, nylon, amylases, natural and modified celluloses, polyacrylamides, gabbros, and magnetite.

One skilled in the art will know many other suitable carriers for binding antibody or antigen, and will be able to adapt such support for use with the present invention. For example, protein isolated from disease cells can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound detectably labeled antibody. The amount of bound labeled antibody on the solid support can then be detected by conventional means.

The invention also encompasses kits for detecting the presence of a marker protein or nucleic acid in a biological sample. Such kits can be used to determine if a subject is suffering from or is at increased risk of developing certain diseases, e.g., diabetes and/or metabolic syndrome. For example, the kit can comprise a labeled compound or agent capable of detecting a marker protein or nucleic acid in a biological sample and means for determining the amount of the protein or mRNA in the sample (e.g., an antibody which binds the protein or a fragment thereof, or an oligonucleotide probe which binds to DNA or mRNA encoding the protein). Kits can also include instructions for interpreting the results obtained using the kit.

For antibody-based kits, the kit can comprise, for example: (1) a first antibody (e.g., attached to a solid support) which binds to a marker protein; and, optionally, (2) a second, different antibody which binds to either the protein or the first antibody and is conjugated to a detectable label.

For oligonucleotide-based kits, the kit can comprise, for example: (1) an oligonucleotide, e.g., a detectably labeled oligonucleotide, which hybridizes to a nucleic acid sequence encoding a marker protein or (2) a pair of primers useful for amplifying a marker nucleic acid molecule. The kit can also comprise, e.g., a buffering agent, a preservative, or a protein stabilizing agent. The kit can further comprise components necessary for detecting the detectable label (e.g., an enzyme or a substrate). The kit can also contain a control sample or a series of control samples which can be assayed and compared to the test sample. Each component of the kit can be enclosed within an individual container and all of the various containers can be within a single package, along with instructions for interpreting the results of the assays performed using the kit.

In the methods provided herein, a modulated level of HSP90, specifically HSP90β, may be used as a diagnostic indicator in conjunction with one or more indicators of metabolic syndrome such as those provided herein.

Repeated diagnostic assays can be used to monitor the disease state of the subject.

VII. Treatment of Metabolic Syndrome

As demonstrated herein, inhibition of HSP90 expression or activity, specifically HSP90β expression or activity, improves glucose uptake, insulin signaling, and lipid metabolism. The invention provides methods of treatment of subjects suffering from metabolic syndrome comprising administering an inhibitor of HSP90, preferably an HSP90β inhibitor, more preferably an HSP90β inhibitor, such as those provided herein, to ameliorate at least one sign or symptom of metabolic syndrome. In certain embodiments, the inhibitor of HSP90, preferably the HSP90β-specific inhibitor, can be administered to a subject wherein at least one additional agent for the treatment of metabolic syndrome is administered to the subject. As used herein, the agents can be administered sequentially, in either order, or at the same time. Administration of multiple agents to a subject does not require co-formulation of the agents or the same administration regimen.

The method of treatment of metabolic syndrome using HSP90β inhibitors can be combined with known methods and agents for the treatment of metabolic syndrome. Many agents and regimens are currently available for treatment of metabolic syndrome and diabetes. The specific agent selected for treatment depends upon the subject, the specific symptoms and the severity of the disease state. For example, in certain embodiments, the HSP90β inhibitors can be administered in conjunction with dietary and/or behavior modification, e.g., caloric restriction, alone or in combination with bariatric surgery, and/or with increased physical activity. In certain embodiments, the HSP90β inhibitors can be administered with agents for the treatment of type 2 diabetes, e.g., metformin (Glucophage, Glumetza, others), glitazones, e.g., pioglitazone (Actos), glipizide (Glucotrol), glyburide (Diabeta, Glynase), glimepiride (Amaryl), acarbose (Precose), metformin (Glucophage), Sitagliptin (Januvia), Saxagliptin (Onglyza), Repaglinide (Prandin), Nateglinide (Starlix), Exenatide (Byetta), Liraglutide (Victoza), or insulin.

VIII. Animal Models of Metabolic Syndrome

A number of genetic and induced animal models of metabolic syndromes such as type 1 and type 2 diabetes, insulin resistance, hyperlipidemia, are well characterized in the art. Such animals can be used to demonstrate the effect of HSP90 inhibitors, e.g., HSP90β inhibitors in the treatment of diabetes. Models of type 1 diabetes include, but are not limited to, NOD mice and streptozotocin-induced diabetic rats and mice (models of type 1 diabetes). Genetic and induced models of type 2 diabetes include, but are not limited to, the leptin deficient ob/ob mouse, the leptin receptor deficient db/db mouse, and high fat fed mouse or rat models. In each of the models, the timeline for development of specific disease characteristics are well known. HSP90 inhibitors can be administered before or after the appearance of symptoms of diabetes to demonstrate the efficacy of HSP90 inhibitors, particularly HSP90β inhibitors, in the prevention or treatment of diabetes in these animal models.

Depending on the specific animal model selected and the time of intervention, e.g., before or after the appearance of metabolic syndrome, the animal models can be used to demonstrate the efficacy of the methods provide herein for the prevention, treatment, diagnosis, and monitoring of metabolic syndrome.

IX. Kits

The invention also provides compositions and kits for diagnosing a disease state, e.g. metabolic syndrome. These kits include one or more of the following: a detectable antibody that specifically binds to HSP90β and one or more of a detectable antibody that specifically binds to the HSP90β antibody, reagents for obtaining and/or preparing subject tissue samples for staining, and instructions for use.

The kits of the invention may optionally comprise additional components useful for performing the methods of the invention. By way of example, the kits may comprise fluids (e.g., SSC buffer, TBST) suitable for annealing complementary nucleic acids or for binding an antibody with a protein with which it specifically binds, one or more sample compartments, an instructional material which describes performance of a method of the invention and tissue specific controls/standards.

The invention also provides kits for treatment of metabolic disorder. The kits include at least one HPS90 inhibitor, preferably an HSP90β-specific inhibitor, and one or more of instructions for use and a device for administration, as appropriate.

EXAMPLES

Example 1

Employing Platform Technology to Identify HSPAB1 (HSP90β) as an Important Node of Activity in the Etiology of Diabetes In this example, the platform technology described in detail in international Patent Application No. PCT/US2012/027615 was employed to integrate data obtained from a custom built diabetes model, and to identity novel proteins/pathways driving the pathogenesis of diabetes. Relational maps resulting from this analysis have identified HSPAB1 (HSP90β) as an important node of activity in the etiology of diabetes. Therefore, HSPAB1 (HSP90β) is an important diabetes treatment target, as well as a diagnostic/prognostic marker associated with diabetes.

Five primary human cell lines, namely adipocytes, myotubes, hepatocytes, aortic smooth muscle cells (HASMC), and proximal tubular cells (HK2) were subject to one of five conditions simulating an environment experienced by these disease-relevant cells in vivo. Specifically, each of the five cell lines were exposed separately to each of the following conditions: hyperglycemic conditions, hyperlipidemic conditions, hyperinsulinemic conditions, hypoxic conditions and exposure to lactic acid. The hyperglycemic condition was induced by culturing cells in media containing 22 mM glucose. The hyperlipidemic condition was induced by culturing the cells in media containing 0.15 mM sodium palmitate. The hyperinsulinemic condition was induced by culturing the cells in media containing 1000 nM insulin. The hypoxic condition was induced by placing the cells in a Modular Incubator Chamber (MIC-101, Billups-Rothenberg Inc. Del Mar, Calif.), which was flooded with an industrial gas mix containing 5% $CO_2$, 2% $O_2$ and 93% nitrogen. Each cell line was also treated with 0 or 12.5 mM lactic acid.

In addition, cross talk experiments between two different pairs of cells, human aortic smooth muscle cells (HASMC) (cell system 1) and human kidney 2 (HK2) cells (cell system 2); or liver cells (cell system 1) and adipocytes (cell system 2) were carried out in which the paired cells were co-cultured. This co-culturing approach is referred to as an extracellular secretome (ECS) experiment. The first cell system (e.g., HASMC) was first seeded in the inserts of the wells of a transwell type growth chamber. Six well plates were used to enable better statistical analysis. At the time of seeding with the first cell system in the inserts, the inserts were placed in a separate 6-well plate. The second cell system (e.g., HK2) was seeded on the primary tray. The insert tray containing the first cell system and the primary tray containing the second cell system were incubated at 37° C. overnight. Each of the cell systems was grown in the specific cell specific media (wherein alternatively, each of the cell systems could be grown in a medium adapted to support the growth of both cell types). On the second day, the pre-determined treatment was given by media exchange. Specifically, the inserts containing the first cell system were placed into the primary tray containing the second cell system. The tray was then incubated for a pre-determined time period, e.g., 24 hour or 48 hours. Duplicate wells were set up with the same conditions, and cells were pooled to yield sufficient material for 2D analysis. The media (1 ml aliquot), the cells from the inserts and the cells from the wells of the primary tray were harvested as separate samples. The experiments were conducted in triplicate in order to provide better statistical analysis power.

Cross-talk experiments were also conducted by "media swap" experiments. Specifically, a cultured media or "secretome" from the first cell system, HASMC was collected after 24 hrs or 48 hrs following perturbation or conditioning and then added to the second cell system, Adipoctes, for 24-48 hrs. The final cultured media or "secretome" from the second cell system was then collected. All final secretomes were subjected to proteomic analysis.

The cell model comprising the above-mentioned cells, wherein the cells were exposed to each condition described above, was additionally "interrogated" by exposing the cells to an "environmental perturbation" by treating with Coenzyme Q10. Specifically, the cells were treated with Coenzyme Q10 at 0, 50 μM, or 100 μM.

Cell samples for each cell line, condition and Coenzyme Q10 treatment were collected at various times following treatment, including after 24 hours and 48 hours of treatment. For certain cells and under certain conditions, media samples were also collected and analyzed.

iProfiling of changes in total cellular protein expression by quantitative proteomics was performed for cell and media samples collected for each cell line at each condition and with each "environmental perturbation", i.e, Coenzyme Q10 treatment, using the techniques described above in the detailed description.

Proteomics data collected for each cell line listed above at each condition and with each perturbation, and bioenergetics profiling data collected for each cell line at each condition and with each perturbation, were then processed by the REFS™ system. A composite perturbed network was generated from combined data obtained from all the cell lines for one specific condition (e.g., hyperglycemia) exposed to perturbation (CoQ10). A composite unperturbed network was generated from combined data obtained from all of the cell lines for the same one specific condition (e.g., hyperglycemia), without perturbation (without CoQ10). Similarly, a composite perturbed network was generated from combined data obtained from all of the cell lines for a second, control condition (e.g., normal glycemia) exposed to perturbation (CoQ10). A composite unperturbed network was generated from combined data obtained from all of the cell lines for the same second, control condition (e.g., normal glycemia), without perturbation (without CoQ10).

Each node in the consensus composite networks described above was simulated (by increasing or decreasing by 10-fold) to generate simulation networks using REFS™, as described in detail above in the detailed description.

The area under the curve and fold changes for each edge connecting a parent node to a child node in the simulation networks were extracted by a custom-built program using the R programming language, where the R programming language is an open source software environment for statistical computing and graphics.

Delta networks were generated from the simulated composite networks. To generate a Diabetes disease condition vs. normal condition differential network in response to Coenzyme Q10 (delta-delta network), steps of comparison were performed as illustrated in FIG. 1, by a custom built program using the PERL programming language.

Specifically, as shown in FIG. 1, Treatment T1 refers to Coenzyme Q10 treatment and NG and HG refer to normal and hyperglycemia as conditions. Unique edges from NG in the NG∩HG delta network was compared with unique edges of HGT1 in the HG∩HGT1 delta network. Edges in the intersection of NG and HGT1 are HG edges that are restored to NG with T1. HG edges restored to NG with T1 were superimposed on the NG∩HG delta network (shown in darker colored circles in FIG. 2).

Specifically, a simulated composite map of normal glycemia (NG) condition and a simulated composite map of hyperglycemia (HG) condition were compared using a custom-made PERL program to generate unique edges of the normal glycemia condition. A simulated composite map of hyperglycemia condition without Coenzyme Q10 treatment (HG) and a simulated map of hyperglycemia condition with Coenzyme Q10 treatment (HGT1) were compared using a custom-made PERL program to generate unique edges of the hyperglycemia condition with Coenzyme Q10 treatment (HGT1). Edges in the intersection of the unique edges from normal glycemia condition (NG) and the unique edges from hyperglycemia condition with Coenzyme Q10 treatment (HGT1) were identified using the PERL program. These edges represent factors/networks that are restored to normal glycemia condition from hyperglycemia condition by the treatment of Coenzyme Q10. The delta-delta network of hyperglycemic edges restored to normal with Coenzyme Q10 treatment was superimposed on the normal glycemia ∩ hyperglycemia delta network.

Figure 2:
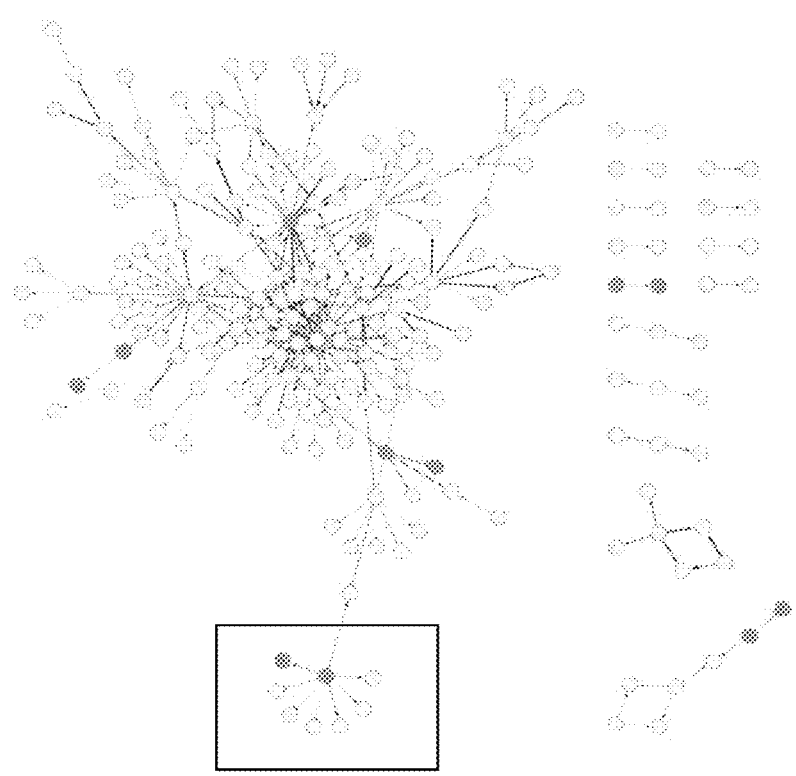
FIG. 2 is a schematic representation of a network in diabetic versus normal cellular models that were generated by the interrogatory platform method discussed herein. The darker nodes represent the five predominant hubs of activity identified using the method.

Output from the PERL and R programs were inputted into Cytoscape, an open source program, to generate a visual representation of the superimposed network between the hyperglycemic edges restored to normal condition with Coenzyme Q10 treatment delta-delta network and the normal glycemia vs. hyperglycemia delta network. An output from the Cytpscape program representing the superimposed network is shown in FIG. 2. Darker colored circles in FIG. 2 are identified edges which were restored to a normal glycemia condition from a hyperglycemia condition by the treatment of Coenzyme Q10. Lighter colored circles in FIG. 2 are identified unique normal hypercemia edges. The subnetwork in the box shown in FIG. 2 is enlarged and represented in FIG. 3. HSP90AB1 (HSP90β) is one of the identified markers which are edges restored to a normal glycemia condition from a hyperglycemia condition by the treatment of Coenzyme Q10 (see FIG. 3).

Figures 3, 4:
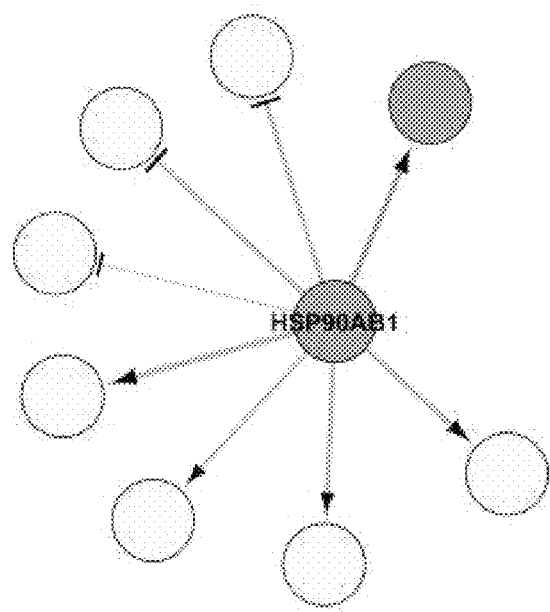
FIG. 3 is a magnified version of the section of the network indicated by the box in FIG. 2, showing an association map of HSP90AB1 (HSP90β) and causal nodes of interest from the platform method diabetes output discussed herein.
FIG. 4 provides a key to the symbols and color codes used to delineate causal protein associations in delta-delta networks.

FIG. 3 represents an association map of HSP90AB1 (HSP90β) and causal nodes of interest from the Interrogative Biology® diabetes outputs. FIG. 4 represents list of symbols and color codes used in the differential network maps to delineate causal associations of proteins in disease and normal cell models. HSP90AB1 (HSP90β) was identified in this superimposed delta-delta network as a potential therapeutic factor, drug target and biomarker for diabetes.

Example 2

HSP90β Regulation of Cellular Substrate Metabolism and Insulin Signaling

A. Materials and Methods:

1. Differentiation of Human Myoblasts into Myotubes:

Human skeletal muscle myoblasts (HSMM) were procured from PromoCell and were cultured in growth media recommended by the vendor. Confluent cultures were replaced with differentiation media (DMEM, 2% horse serum, pyruvate and HEPES) and cells allowed to differentiate for 7 to 10 days.

2. siRNA of Hsp90β/Inhibition of HSP90:

Commercially available trifecta siRNA from IDT® was used for specific knockdown of Hsp90β. As a control a scrambled siRNA was included in all experiments. All three siRNA provided by IDT® was separately transfected using a Mirus® TKO® transfection reagent. Hsp90β knockdown was confirmed by western blotting and qPCR using commercially available antibody and primer probes that are specific to human Hsp90β protein and mRNA. HSP90 inhibitor CCT018159 was obtained from Tocris Bioscience.

3. siHsp90β Sequence Information:

H1:
Duplex Sequences (SEQ ID NO: 1)
5'-rArGrG rCrCrG rArCrA rArGrA rArUrG rArUrA rArGr
G rCrAG T-3'

(SEQ ID NO: 2)
5'-rArCrU rGrCrC rUrUrA rUrCrA rUrUrC rUrUrG rUrCr
G rGrCrC rUrCrA-3'

H2:
Duplex Sequences (SEQ ID NO: 3)
5'-rCrArA rCrGrA rUrGrA rUrGrA rArCrA rGrUrA rUrGr
C rUrUG G-3'

(SEQ ID NO: 4)
5'-rCrCrA rArGrC rArUrA rCrUrG rUrUrC rArUrC rArUr
C rGrUrU rGrUrG-3'

H3:
Duplex Sequences (SEQ ID NO: 5)
5'-rCrGrU rUrGrC rUrCrA rCrUrA rUrUrA rCrGrU rArUr
A rArUC C-3'

(SEQ ID NO: 6)
5'-rGrGrA rUrUrA rUrArC rGrUrA rArUrA rGrUrG rArGr
C rArArC rGrUrA-3'

4. Insulin Signaling Experiments:

Human HSMM myotubes cells that were plated in 12 well plates the previous week were used. The media was aspirated and fresh media with appropriate dilutions of the NC and H3 siRNA for Hsp90 knockdown were added such that the final concentration in the wells of the plate was 100 nM. Mirus TKO transfection reagent was used for transfecting the cells. The plate was then incubated at 37° C. overnight.

The media was aspirated and the cells were washed off twice—first with warm PBS and second with 0.1% BSA containing growth media. The cells were then serum starved for 2-3 hours in 0.1% differentiation media containing the appropriate inhibitors at 37° C. followed by insulin stimulation for 5 minutes (0, 10, and 100 nM insulin).

The wells were then washed once with PBS and harvested into 100 μl of RIPA buffer containing protease and phosphatase inhibitors. The plate was placed on ice and, using a cell scraper, the cells were scraped from the plate. The lysates were collected in 1.5 ml Eppendorf tubes and homogenized by using a syringe and needle. The lysates were then centrifuged at 4° C. for 10 mins at 14,000 RPM. The lysates can be stored at −20° C. for future use.

Protein content was estimated by BCA assay and samples were prepared for gel electrophoresis and western blotting as described in subsequent sections. The total volume required to load 10 μg of total protein was calculated.

The samples were loaded onto a bis-tris or a tris-glycine-SDS gel. Proteins were transferred to a PVDF or a nitrocellulose membrane using routine wet or dry transfer methods. The membranes were then blocked for at least an hour using the blocking buffer. The membranes were then cut prior to exposure to the appropriate primary antibodies diluted in blocking buffer for incubation. Primary antibodies to pAKT (p-Akt, S473), pERK (p-Erk, Phospho-p44/42 MAPK (Erk1/2) (Thr202/Tyr204), and pGSK3β (Phospho-GSK-3β (Ser9) were obtained from Cell Signaling Inc.® Other antibodies were also obtained from commercial sources. The membrane was placed in the shaker and incubated in the refrigerator (4° C.) overnight.

Visualization of proteins and quantification of western blots was performed as follows. The membranes were washed thrice using 1×PBS-T (10 minutes each). The appropriate HRP conjugated secondary antibodies were diluted (1:10,000) in blocking buffer and added to each of the membranes. Membranes were incubated for at least an hour in the shaker at room temperature. The membranes were washed three times (10 minutes each) with PBS-T. After the final wash the membranes were kept in the PBS-T until detection of the proteins.

Each strip of membrane was taken out arranged in a clean flat surface. The chemiluminescent substrate (Pierce® PICO or DURA) was added to each of the membranes and incubated for 5 minutes. The membranes were then placed in a clean sheet of plastic for visualization using the BIO-RAD® chemiluminescence imager. The bands were quantified using the BIORAD® software.

5. Insulin Stimulated Glucose Uptake:

HSMM myoblasts (20,000 cells/well) were differentiated with 2% horse serum in 96 well plates for 7 days before experiment. Cells were washed twice with 200 ul MBSS buffer containing 0.1% BSA, and then serum starved with 100 ul MBSS 0.1% BSA for 4 hours. Some wells were also pretreated with 25 uM LY compound for 20 minutes. Upon initiation of insulin stimulation, 100 ul 2× reagents in MBSS 0.1% BSA buffer was added to 100 ul starvation media to make 1× concentration for the experiment. The 2× reagents are: insulin (0, 20 nM, and 200 nM); 2NBDG (500 uM). Cells were treated with insulin and 2NBDG for 30 min, then washed twice with MBSS buffer, then 50 ul MBSS buffer were added to wells. Glucose uptake was detected with fluorometer along with background detection with wells with no cells in them. After fluorometer readout, a fixative (formalin, 50 ul) was added to 50 ul MBSS in the wells, then 100 ul 1 uM DAPI was added to 100 ul formalin and MBSS mixture.

6. Bioenergetic Profiling of Myotubes:

HSMM myotubes cultured in wells in a Seahorse® assay cartridge were differentiated with 2% horse serum myocyte differentiation media for 7 days. Cells were transfected with either negative control scrambled siRNA or siHsp siRNA with TKO transfection reagents at concentration of 50 nM following vendor instructions as described above (Mirus Bio®). After 48 hours transfection, cells were subjected to Seahorse® bioenergetics analysis using drugs to modulate cell energetics, i.e., oligomycin, carbonyl cyanide-M-chlorophenyl hydrazine (CCCP), and rotenone. Oligomycin inhibits mitochondrial ATP synthase (complex V of ET chain) and allows analysis of glycolytic capacity. CCCP is an uncoupler that pumps proton out of the mitochondrial membrane, thereby inducing maximum compensatory oxygen consumption, and allows analysis of uncoupled OCR. Rotenone inhibits NADH dehydrogenase (complex I of ET chain) and allows analysis of non-mitochondrial OCR.

To perform the assay, each well of the Seahorse® assay cartridge was washed with 1 ml running media. 500 ul of running media was added to each well and the plate was placed in an 37° C. ($CO_2$ free) incubator. Drugs to modulate mitochondrial activity were prepared at a 10× (10 uM) concentration, so that after addition to the cartridge, the final concentration would be 1× (1 μM). Oligomycin (50 ul), CCCP (55 ul) and rotenone (55 ul) were added to ports A, B, and C of the cartridge and the cartridge was placed back in the incubator. The Seahorse® assay wizard was opened and the cycle parameters and times were setup. The Seahorse® assay was then performed using the instrument. After the Seahorse® assay, cells were lysed with 50 ul 450 mM NaOH and then neutralized with 5 ul Tris 6.8. DNA lysates were subjected to spectrophotometric analysis at OD260 using BioTek® Take3 DNA plate reader. The data were normalized with DNA contents of the cells.

B. Results

Figure 5:
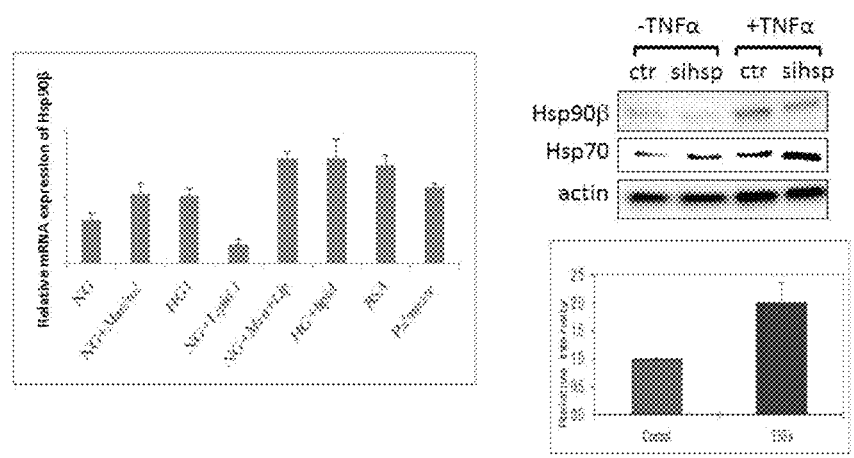
FIG. 5 shows the induction of Hsp90β expression mRNA and protein in response to metabolic factors and inflammation.

1. Metabolic and Stress Factors Induce Expression of Hsp90β:

Acute treatment of myotubes with metabolic and stress factors was shown to modulate expression of Hsp90β. HSMM myoblasts were differentiated in media containing 2% horse serum for 7 days, then subjected to different nutrient conditions for 24 hours including: normal glucose (NG 5 mM glucose), high glucose (HG 25 mM), NG+mannitol (mannitol is used to equilibrate the osmotic pressure), mixture of oleic acid and linoleic acid (150 uM), palmitate (150 uM), and a combination of these different conditions. Results showed that after 24 hours, high glucose did not have significant effects on Hsp90β mRNA expression, despite the effects induced by osmotic stress. With normal glucose conditions, the lipid mixture suppressed HSP90β mRNA expression, while it elevated HSP90β mRNA expression at high glucose condition. Palmitate with NG suppressed HSP90β mRNA expression as compared with BSA control. These data indicated that HSP90β expression is regulated by different metabolic factors such as lipidemia, demonstrating a relationship with oxidative metabolism and stress responses. Hsp90β expression was induced upon treatment of myotubes with TNFα (FIG. 5).

Figure 6:
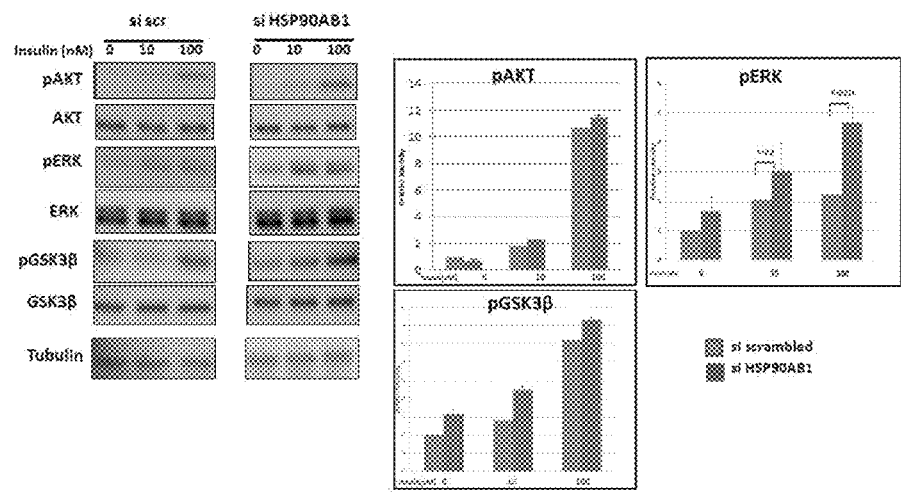
FIG. 6 shows the results of knockdown of Hsp90β in myotubes leading to a significant increase in insulin stimulated phosphorylation of AKT, ERK, and GSK3β. The effect of knockdown on pERK was significant when compared to scrambled siRNA.

2. Knockdown of Hsp90β in Myotubes Resulted in Increased Insulin Signaling:

HSMM myotubes were sequentially (1) transfected with 3 different siRNAs targeting HSP90AB1 for 48 hours, (2) serum starved for 3 hours, and (3) subjected to stimulation of different concentrations of insulin (0, 10, 100 nM). Signaling events downstream of insulin stimulation were assessed by western blotting for levels of total and phosphorylated Akt, Erk, and GSK3β. Quantification of western blots showed that HSP90AB1 knockdown induced significantly elevated insulin stimulated phosphorylation of Akt, ERK, and GSK3β. Akt is activated by phospholipid binding and activation loop phosphorylation at Thr308 by PDK1 and by phosphorylation within the carboxy terminus at Ser473. MEK1 and MEK2 activate p44 and p42 through phosphorylation of activation loop residues Thr202/Tyr204 and Thr185/Tyr187, respectively. GSK-3 is a critical downstream element of the PI3K/Akt cell survival pathway whose activity can be inhibited by Akt-mediated phosphorylation at Ser21 of GSK-3α and Ser9 of GSK-3β (FIG. 6).

Figure 7:
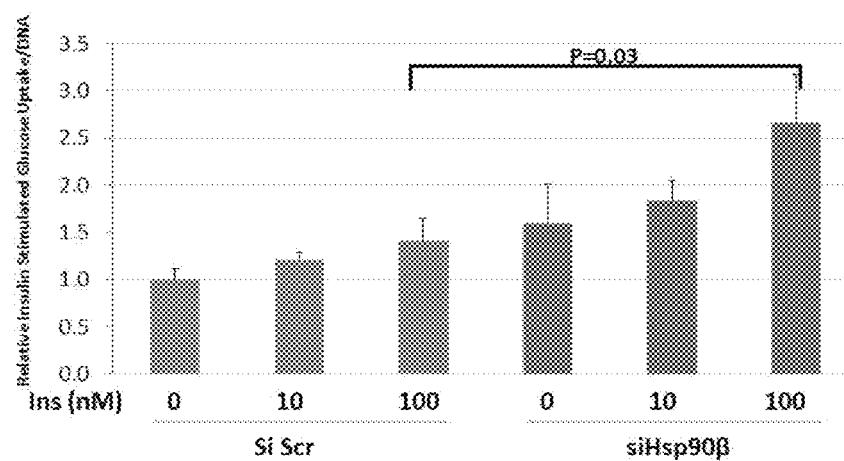
FIG. 7 shows the results of knockdown of Hsp90β in myotubes, leading to a significant increase in insulin stimulated glucose uptake when compared to a scrambled siRNA (si scrambled).

3. Knockdown of Hsp90β in Myotubes Resulted in Increased Insulin Stimulated Glucose Uptake:

Consistent with elevated signaling events induced by Hsp90β knockdown, glucose induced glucose uptake was measured in HSMM myotubes using the fluorescent glucose analog 2-NBDG. Using the methods provided above, cells were sequentially transfected with either control or Hsp90β siRNA for 48 hours, serum starved for 4 hours, and stimulated with different concentrations of insulin with presence of 250 uM 2-NBDG for 30 min. The cells were then washed with PBS and fluorescence was detected using a plate reader. The fluorescence of the cell reflects the amount of the glucose taken up by the cells. The results demonstrated that the siHsp90β treated cells, with reduced HSP90β expression, showed significantly enhanced insulin stimulated glucose uptake when compared to cells treated with the non-specific si-srambled under the same conditions. These data demonstrate that inhibition or knockdown of Hsp90β in myotubes enhances insulin stimulated glucose uptake (FIG. 7).

4. Knockdown of Hsp90β in Myotubes Resulted in Increased Mitochondrial Efficiency:

HSMM myotubes were transfected with siRNA of either control or siHsp90β for 48 hours as described above, then subjected to Seahorse® bioenergetic profiling (XF24 Analyzer) using different mitochondrial drugs including oligomycin, CCCP, and rotenone; and monitored changes on oxygen consumption rate (OCR) that reflects either basal or maximum mitochondrial oxidative capacity. The results were normalized by DNA content.

Figure 8:
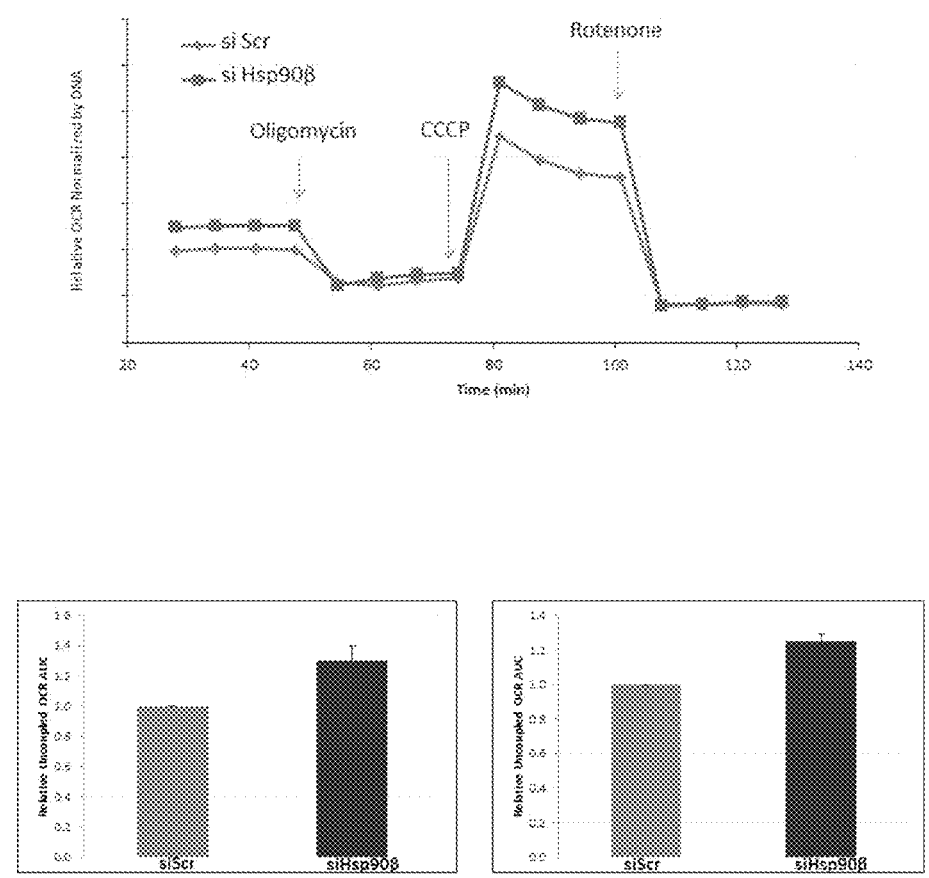
FIG. 8 shows the results of knockdown of Hsp90β in myotubes, leading to a significant increase in CCCP induced uncoupling in comparison with scrambled siRNA. Basal respiration in myotubes in which Hsp90β was knocked down was observed to be moderately higher than in myotubes treated with a scrambled siRNA (si scrambled).

The results demonstrated that in both basal and uncoupled conditions, HSP90β knockdown myotubes displayed enhanced oxidative respiration. This demonstrates that Hsp90β knockdown induces profound metabolic changes on mitochondrial in myotubes, indicating a role for Hsp90β in regulation of mitochondrial functions via its chaperone activity, likely by targeting the incorporation of different mitochondrial proteins. Quantification of area under the curve (AUC) for both basal and uncoupled OCR in myotubes, with either control or siHSP90AB1 siRNAs from the bioenergetics profiling study, revealed significantly increased basal and uncoupled OCR in Hsp90β knockdown cells, thereby demonstrating improved mitochondrial efficiency (FIG. 8) upon knockdown of Hsp90β expression.

Figure 9A:
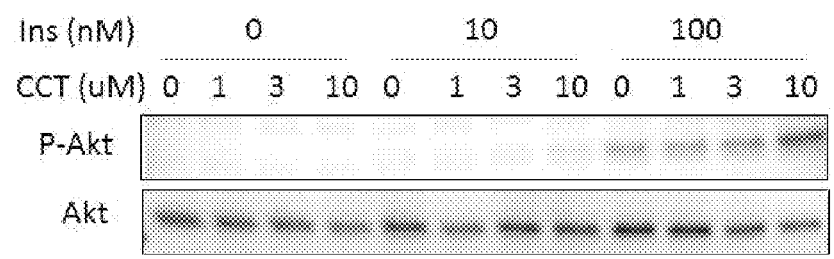
FIGS. 9A and 9B show (A) a western blot and (B) quantitative analysis demonstrating the effects of the treatment of myotubes with Hsp90 inhibitor (CCT018159), which was observed to increase levels of phospho-AKT in comparison with untreated cultures. No significant changes in pERK or pGSK3β was observed.
Figure 9B:
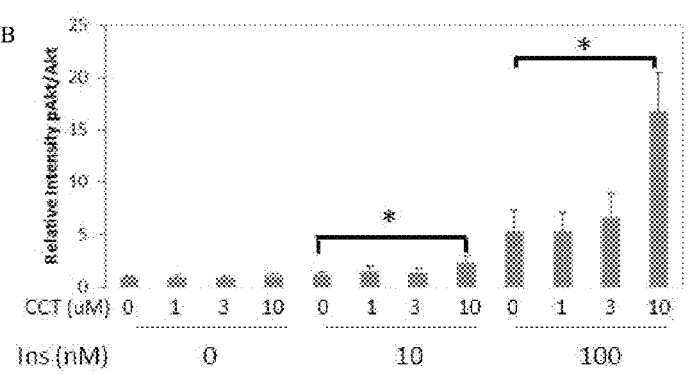

5. HSP90 Inhibition by Small Molecule Inhibitor (CCT018159) Increased Phosphorylation of AKT, but not ERK and GSK3β:

Myotubes were treated with a small molecule inhibitor of HSP90 (CCT018159) then subjected to insulin stimulation. The small molecule inhibitor of HSP90 (CCT018159) inhibits both HSP90α and HSP90β. The effect of the small molecule inhibitor on insulin signaling was assessed by measuring insulin stimulated phosphorylation of the downstream targets Akt, ERK, and GSK3β by western blot. The results demonstrated that the higher concentration of CCT018159, specifically 10 uM, significantly enhanced insulin stimulated phosphorylation of Akt, indicating that the HSP90 inhibition enhanced insulin sensitivity in myotubes. However, no change in the level of pERK or pGSK3β was observed (FIG. 9).

Figure 10:
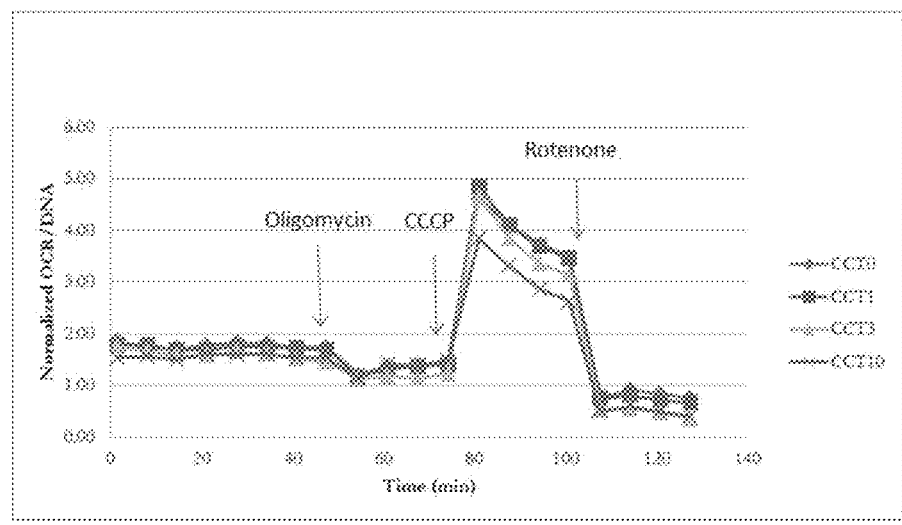
FIG. 10 shows the results from the treatment of skeletal muscle myotubes with Hsp90 inhibitor (CCT018159) at 1 μM, 3 μM, and 10 μM, which did not have a significant effect on CCCP induced uncoupling response on mitochondrial metabolism.

A differential effect of Hsp90 small molecule inhibitors on cellular bioenergetics was observed in comparison with that of Hsp90β-specific knockdown. The bioenergetic profile of myotubes following treatment with CCT018159 at different concentrations showed a different profile from what was observed with Hsp90β knockdown cells. There was no observed change on basal OCR, and yet the uncoupled OCR was actually decreased in a concentration dependent manner, where 10 uM CCT018159 induced greater suppression of CCCP induced OCR. This different profile indicates that increased OCR in both basal and uncoupled states is Hsp90β specific, while CCT018159 inhibits both Hsp90α and Hsp90β by blocking their ATP binding pockets. At a lower concentration of CCT018159 (1 μM), increased uncoupled OCR was observed in treated myotubes (FIG. 10).

C. Conclusions:

In summary, Hsp90β regulates insulin signaling, glucose uptake, and substrate metabolism in skeletal muscle myotubes. Induction of Hsp90β mRNA and protein in response to hyperlipidemia, hyperglycemia and pro-inflammatory cues demonstrates a role of the protein in the pathophysiology of diabetes. Knockdown of Hsp90β in myotubes resulted in a significant increase in glucose uptake demonstrating its role in glucose regulation. Knockdown of Hsp90β in myotubes also resulted in a large increase in phosphorylation of ERK and as well as an increase in the phosphorylation of AKT and GSK3β, demonstrating a functional bifurcation of insulin signaling and indicating that Hsp90β is involved in a selective mechanism. Hsp90β knockdown has a significant effect on bioenergetics and mitochondrial substrate metabolism. The HSP90 inhibitor CCT018159, which inhibits both Hsp90α and Hsp90β, had a less profound effect on insulin signaling and bioenergetics, indicating that Hsp90β-specific inhibition is more efficacious than a pan Hsp90 inhibition approach.

Example 3

HSP90β Regulation of Metabolic Enzyme Expression in Skeletal Muscle Myotubes

Figure 11A:
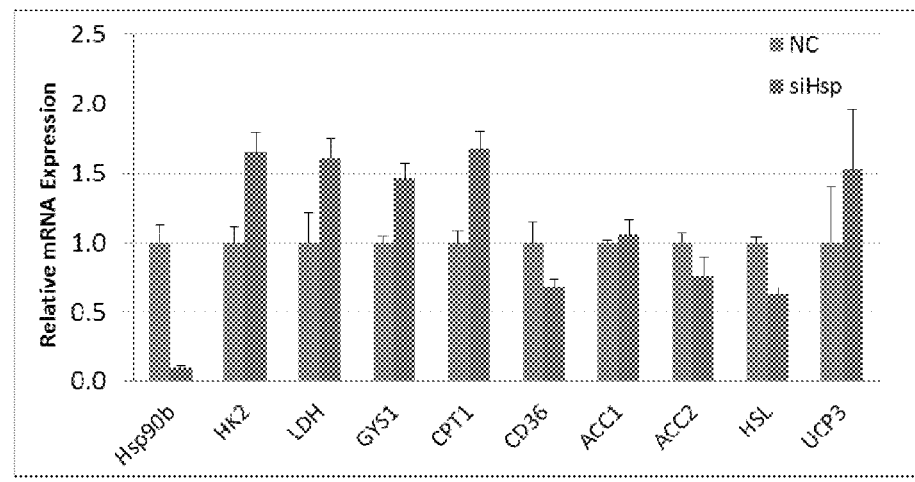
FIGS. 11A and 11B show the effects of knockdown of Hsp90β in myotubes on (A) metabolic enzyme gene expression (hexokinase 2 (HK2); lactate dehydrogenase (LDH); glycogen synthase 1 (GYS1); carnitine palmitoyl transferase 1 (CPT-1); Acetyl CoA carboxylase 1 and 2 (ACC1 and ACC2); hormone sensitive lipase (HSL); and mitochondrial uncoupling protein 3 (UCP 3)); and on (B) UCP3 expression in skeletal muscle myotubes.
Figure 11B:
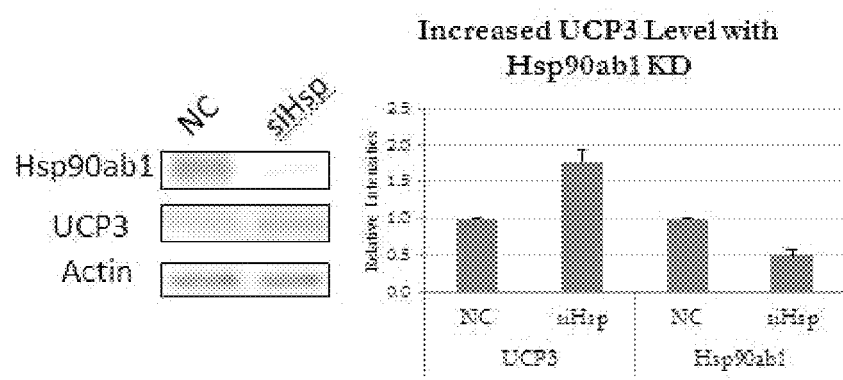

Myoblasts were cultured and differentiated into myotubes and treated with siRNAs essentially as described above. mRNA expression of a series of metabolic enzymes involved in various metabolic pathways was assayed by rtPCR using routine methods. The enzymes include those involved in glycolysis (HK2, LDH, GYS1), lipid oxidation (CPT1, UCP3), fatty acid transport (CD36), and fatty acid synthesis (ACC1 and ACC2), lipolysis (HSL). mRNA expression in the cells treated with the HSP90β siRNA was normalized to the expression of the gene in the cells treated with the scrambled siRNA. The results are shown in FIG. 11A. mRNA expression levels of HK2, LDH, GYS1, CPT1 and UCP3 were found to be increased upon knockdown of HSP90β expression, whereas the expression levels of CD36 and HSL were found to be decreased upon knockdown of HSP90β expression. A decreasing trend of expression of ACC2, involved in fatty acid synthesis, was also observed. UCP3 protein levels were found to be substantially increased upon knockdown of HSP90 (FIG. 11B). The UPC3 protein expression level in skeletal muscle is typically low in diabetics, but its expression is induced by exercise. Without being bound by mechanism, it is suggested that knockdown of HSP90β expression could be exerting a beneficial effect in the treatment of metabolic syndrome by modulation of proteins such as UCP3.

Example 4

HSP90β Regulation of Glycolytic Flux in Skeletal Muscle Myotubes

Myoblasts were cultured and differentiated into myotubes essentially as described above, subject to growth under normoglycemic and hyperglycemic conditions. The cells subject to hyperglycemic conditions were grown and differentiated in 5 mM glucose, and cultured in 11 mM glucose prior to transfection with siRNA. Cells grown under both normoglycemic and hyperglycemic conditions were transfected with HSP90β siRNA or a scrambled control siRNA. The cells were then subject to Searhorse® analysis as described above to analyze glycolytic flux, with the hyperglycemic cells being assayed in 11 mM glucose.

Figure 12:
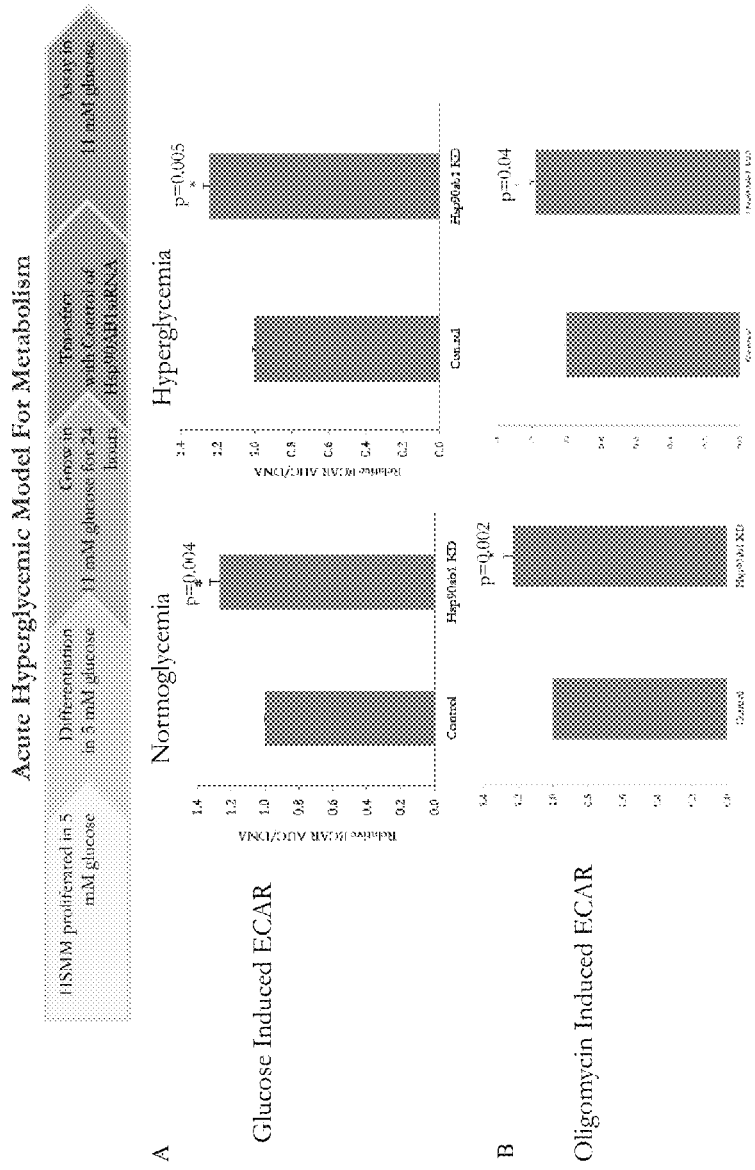
FIGS. 12A-12D show the effect of knockdown of HSP90β on glycolytic flux in skeletal muscle myotubes in (A) glucose induced ECAR; (B) oligomycin induced ECAR; (C) basal OCR; and (D) uncoupled OCR.
Figure 12:
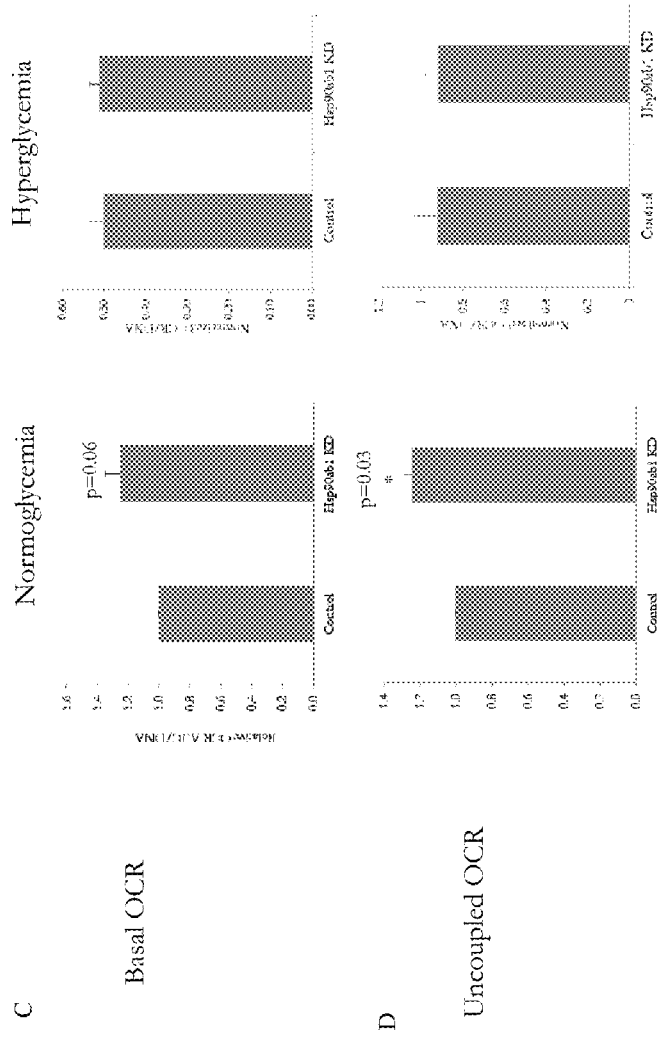

As shown in FIGS. 12A and 12B, knockdown of HSP90β increased glucose induced ECAR and oligomycin induced ECAR under both normoglycemic and hyperglycemic conditions. However, although knockdown of HSP90β increased basal OCR and uncoupled OCR under normoglycemic conditions, no change in basal OCR or uncoupled OCR were observed under hyperglycemic conditions (FIGS. 12C and 12D). These results demonstrate the Hsp90AB1 regulates both mitochondrial respiration and glycolysis under different conditions. Without wishing to be bound by mechanism, these results suggest that reduced Hsp90AB1 protein levels may elevate the overall substrate metabolism, thereby improving systemic metabolism in vivo.

Example 5

Figure 13A:
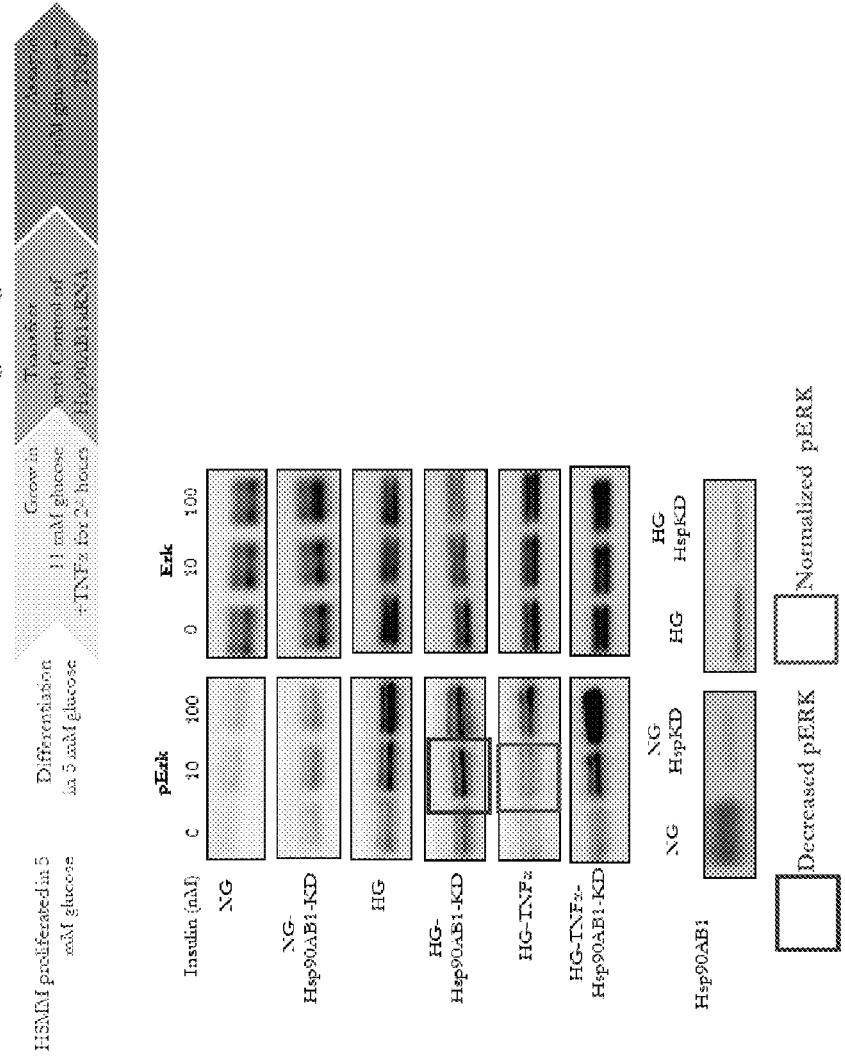
FIGS. 13A and 13B show the effect of knockdown of HSP90β on the ratio of phosphorylated-Erk levels to total Erk levels in an inflammatory insulin resistance model in muscle myotubes as shown in (A) western blot and (B) quantitatively.

HSP90β Regulation of pERK Levels in an Inflammatory Insulin Resistance Model in Skeletal Muscle Myotubes Myoblasts were cultured and differentiated into myotubes essentially as described above, subject to growth under normoglycemic and hyperglycemic conditions. The cells subject to hyperglycemic conditions were grown and differentiated in 5 mM glucose, and cultured in 11 mM glucose for 24 hours prior to transfection with siRNA and/or treatment with TNF-α. Cells grown under normoglycemic conditions, hyperglycemic conditions, or hyperglycemic conditions in the presence of TNF-α were transfected with HSP90β siRNA or a scrambled control siRNA. Cells grown under hyperglycemic conditions were then cultured in the presence of 11 mM glucose and/or TNF-α accordingly. Cells were exposed to increasing concentrations of insulin (0, 10, 100 nM) for 5 min prior to harvest and analysis by western blot. Briefly, cells were harvested into RIPA buffer containing protease and phosphatase inhibitors. Cells were lysed using a syringe and needle. Total protein concentrations were determined for each of the samples. Equivalent amounts of proteins were resolved by SDS-PAGE. Proteins were transferred to nitrocellulose and probed with commercially available antibodies for the detection of both total and phosphorylated ERK (FIG. 13A). The amount of total ERK and phosphorylated ERK were determined quantitatively using a phosphorimager and ratios of phosphorylated ERK to total ERK were calculated (FIG. 13B).

Figure 13B:
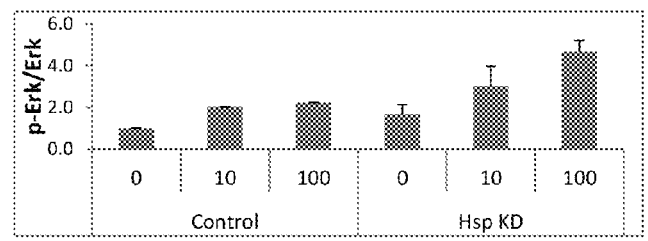
Figure 13B:
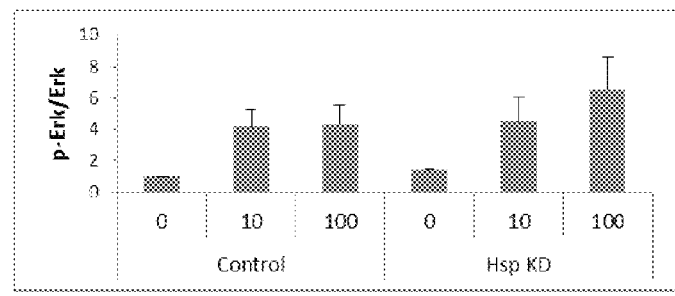
Figure 13B:
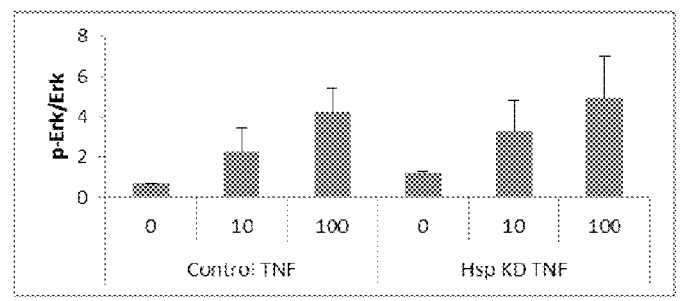

As shown in FIGS. 13A and 13B, under normoglycemic conditions, both basal levels of ERK phosphorylation and insulin signaling, as determined by ERK phosphorylation, is increased by the knockdown of HSP90β expression. Increased insulin stimulated ERK phosphorylation in NG skeletal muscle myotubes was observed with Hsp90AB1 knockdown. Although HG alone did not suppress insulin signaling and ERK phosphorylation, HG conditions in the presence of TNFα strongly suppressed insulin stimulated ERK phosphorylation in the presence of HSP90β. However, under the same HG and TNFα condition, Hsp90AB1 knockdown rescued ERK phosphorylation suppressed by TNFα, indicating the Hsp90AB1 knockdown rescued TNFα induced insulin resistance in HG condition.

Example 6

HSP90β Regulation of Lipid Metabolism in Skeletal Muscle Myotubes

Figure 14:
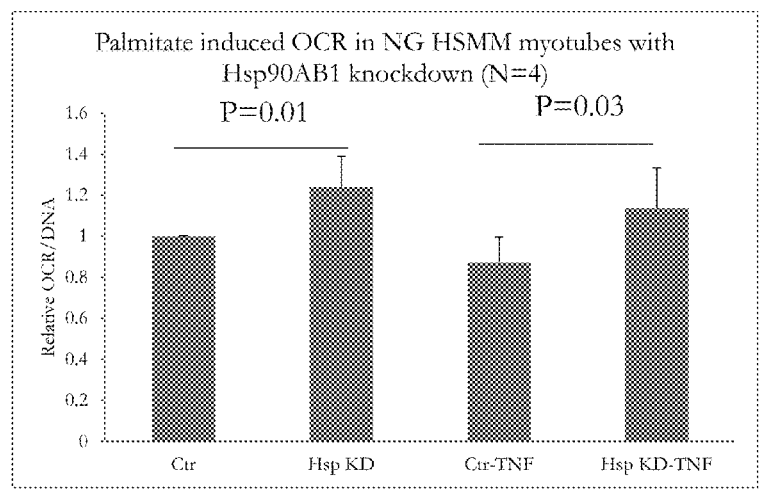
FIG. 14 shows the effect of HSP90β knockdown on the relative OCR/DNA ratio in a palmitate induced OCR under normal-glucose conditions in skeletal muscle myotubes.

Having demonstrated the effects of both HSP90β knockdown in the presence and absence of TNF-α on insulin signaling in skeletal muscle, the effects of HSP90β and TNF-α on lipid metabolism were analyzed. Briefly, myocytes were cultured and differentiated under normal and glycemic conditions essentially as described above and treated with HSP90β or scrambled siRNA. Lipid metabolism was analysed using an OCR Seahorse® assay essentially as described above. As shown in FIG. 14, in the presence of HSP90β, TNF-α decreases lipid metabolism.

However, knockdown of HSP90β increases OCR under normoglycemic conditions in muscle myotubes both in the absence and the presence of TNF-α. These results demonstrate that HSP90β regulates lipid metabolism, as measured by the Seahorse® assay. Although TNF-α decreases lipid metabolism in the presence of HSP90β, knockdown of HSP90β re-establishes lipid metabolism in the presence of TNF-α induced decrease in lipid metabolism.

Example 7

Treatment of Metabolic Syndrome Using an HSP90 Inhibitor

A number of genetic and induced animal models of metabolic syndromes such as type 1 and type 2 diabetes, insulin resistance, and hyperlipidemia, are well characterized in the art. Such animals are used to demonstrate the effect of HSP90 inhibitors, e.g., HSP90β inhibitors, in the treatment of metabolic syndrome, including diabetes. Models of type 1 diabetes include, but are not limited to, NOD mice and streptozotocin-induced diabetic rats and mice (models of type 1 diabetes). Genetic and induced models of type 2 diabetes include, but are not limited to, the leptin deficient ob/ob mouse, the leptin receptor deficient db/db mouse, and high fat fed mouse or rat models. In each of the models, the timeline for development of specific disease characteristics are well known. HSP90 inhibitors can be administered before or after the appearance of symptoms of diabetes to demonstrate the efficacy of HSP90 inhibitors, particularly HSP90β inhibitors in the treatment of diabetes, metabolic disorder, and/or one or more signs of metabolic disorder.

Animals with or without genetic predispositions to metabolic syndrome are raised under appropriate conditions to induce the desired disease state. The animals are divided into at least two groups, treated and control. Treated animals are treated with one or more doses of HSP90 inhibitors, e.g., siRNAs targeted to HSP90, antibodies targeted to HSP90, or small molecule inhibitors of HSP90. Preferably, the small molecules, siRNAs, and antibodies are targeted specifically to HSP90α or HSP90β. The animals are monitored for the development of metabolic syndrome by any of a number of known methods. For example, basal insulin secretion, glucose levels, Hb1Ac levels, inflammatory marker levels, cholesterol and triglyceride levels, weight, fat deposition including fat deposition in the liver, blood pressure, urine output and urine glucose levels, and other relevant markers can be monitored or measured. Markers are analyzed after a period of fast, e.g., overnight fast, or in response to glucose challenge or other metabolic challenge. At predetermined intervals, or at the end of the experiment, animals are euthanized to assess fat deposition, kidney status, and other appropriate indicators of metabolic syndrome.

The outcome of the treatment group(s) is compared to the outcome of the control (untreated or vehicle treated) group. Inhibitors of HSP90β are demonstrated to ameliorate metabolic syndrome in various assessment methods.

Example 8

Validation of HSP90β as a Liver Target for Treatment of Metabolic Syndrome

The liver plays an essential role in the regulation of blood glucose. In a healthy subject, insulin promotes glucose uptake by the liver for conversion into glycogen, reducing blood glucose levels. In metabolic syndrome, the liver does not respond to insulin, either due to insensitivity to insulin or insufficient insulin production, or both, resulting in elevated levels of glucose in the blood, which is toxic.

Hepatic cells (e.g., THLE-2 cells) are analyzed using methods similar to those set forth above for the analysis of insulin signaling and glucose uptake. Briefly, cells are treated with HSP90 inhibitors, preferably HSP90β inhibitors, and assayed for insulin signaling, e.g., by analysis of phosphorylation of AKT, ERK, and GSK3β; glucose uptake, glycogen synthesis; bioenergetics; gene expression of genes involved in gluconeogenesis or lipid/cholesterol metabolism, e.g., by qPCR. Markers of inflammation and endoplasmic reticulum (ER) stress can also be assessed.

Hepatic cells treated with HSP90 inhibitors, particularly HSP90β inhibitors, are found to have better insulin signaling, glucose uptake, and/or lipid metabolism as compared to cells not treated with the inhibitors. The hepatic cells treated with the inhibitors are also found to have less ER stress and/or lower expression of inflammatory markers.

Example 9

Validation of HSP90β as Adipose Target for Treatment of Metabolic Syndrome

Similar to hepatic cells, adipose tissue takes up glucose from the blood in response to insulin, converting the sugar into fat. Fat cells are assessed for insulin responsiveness and glucose uptake using the methods set forth above for analysis of muscle cells and liver cells. Similarly, inflammation and ER stress can also be assessed in the cells.

Adipose cells treated with HSP90 inhibitors, particularly HSP90β inhibitors, are found to have better insulin signaling, glucose uptake, and/or lipid metabolism as compared to cells not treated with the inhibitors. The adipose cells treated with the inhibitors are also found to have less ER stress and/or lower expression of inflammatory markers.

Example 10

Classification of the Specificity of an HSP90 Inhibitor

A number of HSP90 inhibitors are available, such as those provided herein, many of which have undergone or will undergo clinical trials for use in the treatment of various diseases or conditions, most commonly cancer. Depending on the specific mechanism of action or binding site of the inhibitor on the HSP90 transcript, protein, or HSP90 binding protein, the inhibitor may inhibit the activity of one or more HSP90 isoforms, e.g., HSP90α or HSP90β. For example, inhibitors that act at the ATP binding site of HSP90 are likely to have inhibitor activity against both HSP90α and HSP90β. Further, agents can be selected that inhibit interaction of an HSP90 with a specific binding partner (see, e.g., Tsaytler et al., 2009, Cell Stress Chap. 14:629). Similarly, based on the specific nucleic acid or amino acid sequence of the HSP90, nucleic acid based or antibody based inhibitors can be designed to specifically inhibit the expression or activity of HSP90α or HSP90β. Alternatively, nucleic acid based or antibody based inhibitors can be designed to specifically the expression or activity of both HSP90α or HSP90β. Alignments of the HSP90α and HSP90β nucleic acid and amino acid sequences are provided in FIG. 17. One of skill in the art can readily review the alignments to design nucleic acid inhibitors or identify epitopes on HSP90α and HSP90β that could be cross-reactive or specific for a single isoform of HSP90.

Methods to determine if an agent is an inhibitor of the expression or activity of HSP90α, HSP90β or both are well within the ability of those of skill in the art. For example, nucleic acid and antibody inhibitors that inhibit the expression of at least one HSP90 can be tested for specificity in a cell culture system. For example, cells that express both HSP90α and HSP90β are contacted with a series of concentrations of the nucleic acid or antibody, and appropriate controls (e.g., scrambled nucleic acid, non-immune IgG) for an appropriate amount of time. Cells and/or media are harvested, as appropriate. Routine nucleic acid (e.g., RT-PCR, northern blot) and protein (e.g., ELISA, western blot) detection methods are used to determine the expression level of HSP90α and HSP90β as compared to an appropriate control. The specificity of the HSP90 inhibitor can be readily determined.

Competition assays and methods to perform ATP binding and hydrolysis assays are well known in the art and can be used to determine if an agent is an inhibitor of HSP90α, HSP90β, or both, i.e., if the agent can inhibit ATP binding or hydrolysis in one or both isoforms.

Yeast contain only a single copy of HSP90. Yeast strains not expressing HSP90 can be transformed with either HSP90α or HSP90β and the ability to fold client proteins can be monitored. Similarly, mammalian cell lines that express only a single HSP90 isoform, e.g., derived from HSP90α knockout mice, or cells treated with siRNA to inhibit expression of one HSP90 isoform, can be used to distinguish activity of an agent against one or both HSP90 isoforms.

Commercially available kits can also be used to distinguish between inhibitors for inhibitors of HSP90α and HSP90β (BPS Bioscience).

Example 11

Evaluation of Antisense Oligonucleotides (ASO) for Proof of Concept Knockdown of HSP90β in a Diet Induced Obese Model of Insulin Resistance An exemplary animal study model is provided below to further validate HSP90β as a therapeutic target in the prevention and/or treatment of metabolic syndrome, obesity, insulin resistance, and/or type 2 diabetes.

1. Purpose and Rationale

The goals of the study are

1. To identify and characterize antisense oligonucleotides (ASO) for efficient knock down the expression of HSP90β in appropriate in vivo models.

2. To demonstrate that knockdown of HSP90β in vivo results in a functional physiological response with therapeutic benefits.

The desired outcome is the prevent the obese phenotype and diabetic phenotype with knockdown of HSP90β.

The Proof of Concept (PoC) studies are carried out in diet induced obesity (DIO) and insulin resistance (IR) mouse models.

The study is carried out in two parts:
1. Identification of one or more ASOs that significantly knockdown HSP90β expression in the in vivo model by analysis of expression of HSP90β in various tissues.
2. Administration of the ASO(s) to mice subject to diet induced obesity and insulin resistance to demonstrate that inhibition of HSP90β expression prevents, diminishes, or delays the onset of weight gain and the development of a metabolic syndrome.

It is understood that the experimental methods provided below can be readily modified to assay other nucleic acid therapeutics (siRNA, dsiRNA, shRNA), antibody based therapeutics, and small molecule based therapeutics. Further, the study may be modified to include the use of other models of diabetes and metabolic disorders (such as those provided above). As discussed below, depending on the specific results obtained, the time and dosage ranges can be modified based on preliminary analyses of efficacy and toxicity. Such modifictaions are well within the ability of those of skill in the art.

2. Significance

The knockdown of expression of HSP90β delays, diminishes, or prevents weight gain as a result of a high fat diet and diet induced insulin resistance demonstrating the utility of HSP90β as a target for the treatment or management of one or more of obesity, insulin resistance, type 2 diabetes, and metabolic syndrome including one or more of elevated blood pressure, elevated lipid levels, central adiposity, low HDL, and elevated glucose at fasting and/or during a glucose tolerance test.

3. Experimental Approach

Part I: ASO mediated Knockdown of HSP90β and In Vivo (Dose Escalation Study)

Oligonucleotide Selection.

Antisense oligonucleotides are made and tested in vitro to identify ASOs effective in the specific inhibition of expression of HSP90β. One or more ASOs identified in the preliminary in vitro assays are used for the subsequent in vivo studies.

Analysis of Efficacy and Toxicity.

A total of 6 groups of mice, containing 5 mice per group, are maintained on standard chow diet. Mice in Cohort 1, including two groups of 5 mice each, receive an intraperitoneal injection of a normal dose of ASO (30-40 mg/kg) or a high dose of ASO (100-150 mg/kg) twice a week for 2 weeks. Treatment of Cohort 2 and Cohort 3 is initiated after evaluation of the efficacy and toxicity of the preceding cohort (Cohort 1 for Cohort 2 and Cohort 2 for Cohort 3). Sequentially for each cohort, the treatment time increases by two weeks (Cohort 1, 2 weeks; Cohort 2, 4 weeks; Cohort 3, 6 weeks). The following decisions are made based on the results obtained in the prior cohort:

No efficacy—No toxicity: The treatment methods for Cohort Part 1 are repeated with the treatment dosage increased 10-fold. In addition the treatment time is extended by 2 weeks.

Efficacy—No toxicity: The treatment in Part 2 as set forth below is immediately initiated for this ASO. In addition, treatment methods of Part 1 are repeated with a four week dosing schedule rather that a 2 week dosing schedule as with Cohort 1, with the treatment dosage increased 50-fold in order to determine the toxic threshold.

Efficacy—toxicity: The treatment of Part 1 is repeated with the treatment dosage decreased 10 times and the same treatment time is used.

No efficacy—toxicity: This ASO is not be considered for further study.

For each cohort and in all groups, body weight, glucose level and plasma insulin level are measured before every injection and before sacrificing. In addition, plasma level of ASO is measured using a commercially available kit, e.g., OliGreen® ssDNA Quantitation Assay and Kit from Invitrogen®. After 2 weeks, mice are sacrificed and a cardiac puncture with a needle (0.5-1 mL) is immediately performed to retrieve blood. Necropsies are then performed. Selected tissues are collected, weighed, and snap frozen prior to storage at −80° C. until use (with exception of adipose tissues and liver).

The following samples and tissues are collected in a sequential manner:

Blood for plasma preparation
Liver (snap frozen, fixative for paraffin embedding)
Skeletal muscles (snap frozen), including hindlimb and dorsal muscles stored in separate vials.
Adipose tissues (snap frozen and fixed for paraffin embedding), including white adipose tissues (perigonadal, and inguinal) and brown adipose tissue stored in separate vials.
Pancreas (snap frozen)
Kidney (snap frozen)

The knockdown efficiency of HSP90β is determined by measuring expression level of the target using qPCR, western blotting, and/or immunohistochemistry. In addition, plasma insulin, plasma level of leptin, adiponectin, TNFα, PAI-1, serum amyloid A, and IL6 are measured using ELISA. The ASO with the most efficient knockdown is selected and used for subsequent experiments provided below in Part II.

Plasma and liver collected from animals are used for preliminary assessment of toxicity. LDH release assays along with ELISA for inflammatory markers is performed. In addition alanine amino transferase (ALT), aspartate aminotransferase (AST), glutamate dehydrogenase (GLDH) activity assays are performed on plasma and liver homogenates. GSH levels in the liver is ascertained as an additional readout of liver function.

Part II—Proof of Concept Study on Metabolic Effects of HSP90β Knockdown on High Fat Diet Induced Obesity and Insulin Resistance Model A proof of concept study on metabolic effects includes analysis of the following parameters: body weight, fed and fasting blood glucose levels, food intake, water intake, body mass composition, $O_2$ consumption, $CO_2$ production, glucose tolerance test (GTT), insulin tolerance test (ITT), pyruvate tolerance test (PTT), and voluntary activity.

Eight weeks old male lean C57BL/6 mice subject to a 60% kcal % fat high fat diet (HFD) are treated with empirically pre-determined dosages of HSP90β ASO, control ASO, or saline twice a week via intraperitoneal injections (IP). Separate lean control groups receive either saline or control ASO, and are maintained with a standard low fat chow diet (low fat standard diet (LFD) 10% kcal % fat). The treatment groups are shown below:

LFD saline treatment (21 mice)
LFD control ASO treatment (21 mice)
HFD saline treatment (21 mice)
HFD control ASO treatment (21 mice)
HFD HSP90β ASO treatment (21 mice)

Each of the groups of 21 mice are divided into 3 cohorts of animals with 7 mice each. The mice are treated and assessed for a duration of 4 weeks, 6 weeks, and 8 weeks. There are 2 weeks delay for the latter cohorts, i.e. Cohort 2 starts the ASO and HFD treatments 2 weeks after the initiation of treatment of Cohort 1. In this way, Cohort 2 treatment can be modified to 4 weeks treatment instead of 6 weeks treatment upon observation of encouraging results in Cohort 1. If Cohort 1 does not show expected results, the Cohort 2 undergoes 6 weeks treatments. In addition, for each cohort (4 weeks, 6 weeks and 8 weeks), upon demonstration of efficacy in the GTT and ITT studies, the treatments are extended by 1 week to accommodate an PTT (4 weeks become 5 weeks, 6 weeks become 7 weeks, 8 weeks become 9 weeks).

Body weight and fed blood glucose are monitored twice a week before the weekly IP injections from the beginning of the treatment.

For Cohort 1 (4 weeks ASO treatment), GTT and ITT are performed on day 17 and day 24 after the start of ASO treatment. If positive results from GTT and ITT are observed, and PTT is performed on day 31. After 4 weeks (or 5 weeks) of ASO and control treatment, mice from Cohort 1 are euthanized, and tissue and blood samples are collected for further analysis.

For Cohort 2 (6 weeks ASO treatment), GTT and ITT are performed on day 31 and day 38 after the start of ASO treatment. If positive results from GTT and ITT are observed, and PTT is performed on day 45. The mice of Cohort 2 are euthanized, and tissue and blood samples are collected for further analysis after the 6th week or 7th week of treatment.

For Cohort 3 (8 weeks ASO treatment), GTT and ITT are performed on day 45 and day 52 after the start of ASO treatment. If positive results from GTT and ITT are observed, and PTT are performed on day 59. The mice of Cohort 3 are euthanized, and tissue and blood samples are collected for further analysis after the 8th or 9th week of treatment.

The collected tissues are analyzed by qPCR, western blotting, and/or IHC for gene expression and target silencing. Expression of other genes and proteins in insulin signaling pathways can also be analyzed. Blood collected at each time point is processed into plasma and subjected to different biochemical analysis including: TG, FFA, total cholesterol, insulin, serum amyloid A (SAA), adiponectin, TNFα, and PAI-1.

An additional cohort of 10 animals is treated with the following regimens:

HFD control ASO treatment (5 mice)
HFD HSP90β ASO treatment (5 mice)

The mice are subject to monitoring in metabolic cages utilizing the Comprehensive Laboratory Animal Monitoring System (CLAMS) to assess food intake, water intake, voluntary activity and respiration by measuring $VO_2$, $VCO_2$, RQ (respiratory quotient) and heat production, from Day 54 to Day 57. Body composition is determined the same week by dual-energy x-ray absorptiometry (DEXA) on Day 51. This cohort is injected twice a week with different ASOs for 8 weeks.

Materials and Methods.

Animals

Mice of the same gender (male), age and genetic background are used for all comparisons. Male C57BL/6J mice (7 week-old) are obtained from Jackson Laboratories (Bar Harbor, Me.) and initially housed 4-5 per cage at 22° C. on a 12:12 hr day-night cycle. Mice are acclimated at the local animal facility for one week before treatment with the compounds.

Beginning at 8 weeks of age, mice are fed with a high fat diet (Research Diets Cat #: D12492; 60 kcal % fat, 20 kcal % protein, and 20 kcal % carbohydrate) or a standard, low fat diet (10% kcal % fat), depending of the study stage (Part I or Part II). Mice are injected with ASO or saline twice a week. Body weight, glucose level and plasma insulin level are measured before every injection.

Intraperitoneal Glucose Tolerance Test (IPGTT)

Glucose tolerance tests (GTT) are performed after 6 h of fasting. Initial fasting blood glucose levels are determined, followed by intraperitoneal (ip) injection of 20% dextrose solution at a dose of 2.0 g/kg body weight (2 g/kg body weight). Blood glucose levels are measured from the tail vein at 15, 30, 60, 90, 120, 150, and 180 minutes after the glucose injection using a commercially available glucose monitor, e.g., an Accu-chek® Advantage glucometer (Roche Diagnostics®, Indianapolis, Ind.). The area under the curve (AUC) during the GTT is calculated using a commercially available software program, e.g., GraphPad Prism software. GTT experiments for different groups are run in parallel. At each time point of the tail vein glucose measurements, ~40 µL of tail vein blood is collected and plasma is prepared for subsequent insulin level assays using ELISA/RIA for time points at 0, 15, and 30 min after glucose injections.

Intraperitoneal Insulin Tolerance Test (IPITT)

Insulin tolerance test (ITT) is performed after 1 hour fasting. Initial blood glucose levels is determined, followed by injection (ip) of human insulin (1-2 U/kg; Humulin R; Eli Lilly, Indianapolis, Ind.). Blood glucose levels are measured from the tail vein as described above at 15, 30, 60, 90, and 120 min after the insulin injection. The insulin injection amount is determined empirically by insulin response due to the onset of the hepatic insulin resistance in the mice subjected to the high fat diet.

Intraperitoneal Pyruvate Tolerance Test (IPPTT)

Pyruvate challenge test is administered after 6 h of fasting. Initial blood glucose levels are determined, followed by injection (ip) of pyruvate dissolved in saline (2 g/kg; Sigma, St. Louis, Mo.). Blood glucose levels are measured from the tail vein as described above at 15, 30, 60, 90, and 120 min after the pyruvate injection. The area under the curve (AUC) during the test is calculated.

Dual-Energy X-Ray Absorptiometry (DEXA)

The body mass composition of different treatment groups is determined by dual-energy x-ray absorptiometry (DEXA) scanning using LUNAR PIXImus® mouse densitometer following the procedures recommended by the manufacturer. Lean body mass, fat body mass, total body tissue weight, bone density, and bone mineral content are recorded and analyzed.

Comprehensive Lab Animal Monitoring System (CLAMS)

The CLAMS (Columbus Instruments, Columbus, Ohio, USA) metabolic monitoring cages are used to simultaneously monitor horizontal and vertical activity, feeding and drinking, oxygen consumption, and $CO_2$ production. ASO injected and control mice are individually placed in CLAMS cages and monitored over a 4-day period after acclimation to the cages for 1-2 days. The various parameters are recorded in both fasted and fed conditions. Food and water consumption are measured directly as accumulated data. Hourly files display all measurements for each parameter: volume of oxygen consumed, ml/kg per h ($VO_2$), volume of carbon dioxide produced, ml/kg per h ($VCO_2$), respiratory exchange ratio, heat (kcal/h), accumulated food (g), accumulated drink (g), XY total activity (all horizontal beam breaks in counts), XY ambulatory activity (minimum three different, consecutive horizontal beam breaks in counts), and Z activity (all vertical beam breaks in counts). The data are recorded during the 30-s sampling period. The CLAMS data are analyzed by normalizing with lean body mass.

Tissue Collection

At the end of each protocol, mice are euthanized in the following week, and tissues are collected and weighed prior to preservation by snap freezing prior to storage at −80° C. or fixation in formalin for paraffin embedding using standard methods. Blood is collected by cardiac puncture and plasma is prepared.

The following samples and tissues are collected:

Liver (snap frozen, fixative for paraffin embedding)

Skeletal muscles (snap frozen), including hindlimb and dorsal muscles stored in separate vials.

Adipose tissues (snap frozen and fixed for paraffin embedding), including white adipose tissues (perigonadal, and inguinal) and brown adipose tissue stored in separate vials.

Pancreas (snap frozen)

Kidney (snap frozen)

EQUIVALENTS

Those skilled in the art will recognize, or be able to ascertain using no more than routine experimentation, many equivalents to the specific embodiments and methods described herein. Such equivalents are intended to be encompassed by the scope of the following claims.

INCORPORATION BY REFERENCE

Each reference, patent, patent application, and GenBank number referred to in the instant application is hereby incorporated by reference as if each reference were noted to be incorporated individually.

---

The invention claimed is:

1. A method of treating a metabolic syndrome in a subject, comprising administering to the subject an HSP90 inhibitor, wherein the subject with metabolic syndrome exhibits three or more of the following signs:
   a) Blood pressure equal to or higher than 130/85 mmHg;
   b) Fasting blood glucose equal to or higher than 100 mg/dL;
   c) Large waist circumference wherein a large waist circumference is 40 inches or more for men and 35 inches or more for women;
   d) Low HDL cholesterol wherein low HDL cholesterol is under 40 mg/dL for men and under 50 mg/dL for women; and
   e) Triglycerides equal to or higher than 150 mg/dL,
   thereby treating the metabolic syndrome in the subject, and wherein the HSP90 inhibitor comprises a nucleic acid molecule.

2. The method of claim 1, wherein the HSP90 inhibitor is an inhibitor of HSP90β.

3. The method of claim 1, wherein the HSP90 inhibitor is a specific inhibitor of HSP90β.

4. The method of claim 1 or 2, wherein the HSP90 inhibitor is an inhibitor of HSP90α.

5. The method of claim 1, wherein the metabolic syndrome comprises type 2 diabetes.

6. The method of claim 1, wherein the metabolic syndrome comprises type 1 diabetes.

7. The method of claim 1, wherein the metabolic syndrome comprises insulin resistance.

8. The method of claim 1, wherein the metabolic syndrome comprises insulin insufficiency.

9. The method of claim 1, wherein the metabolic syndrome comprises obesity.

10. The method of claim 1, wherein the metabolic syndrome comprises hyperinsulinemia.

11. The method of claim 1, wherein the metabolic syndrome comprises impaired glucose tolerance (IGT).

12. The method of claim 1, wherein the nucleic acid inhibitor comprises an antisense nucleic acid molecule.

13. The method of claim 1, wherein the nucleic acid inhibitor comprises a double stranded nucleic acid molecule.

14. The method of claim 13, wherein the nucleic acid inhibitor comprises a double stranded RNA selected from the group consisting of an siRNA, a shRNA, and a dicer substrate siRNA (DsiRNA).

15. The method of claim 1, wherein treating the metabolic syndrome comprises normalizing a blood glucose level in a subject.

16. The method of claim 1, wherein treating the metabolic syndrome comprises normalizing an Hb1Ac level in a subject.

17. The method of claim 1, wherein treating the metabolic syndrome comprises prevention of at least one complication of diabetes associated with poor circulation.

18. The method of claim 1, wherein treating the metabolic syndrome comprises amelioration of at least one sign or symptom of type 2 diabetes.

19. The method of claim 1, wherein treating the metabolic syndrome comprises amelioration of at least one sign or symptom of type 1 diabetes.

20. The method of claim 1, wherein treating the metabolic syndrome comprises amelioration of at least one sign or symptom of insulin resistance.

21. The method of claim 1, wherein treating the metabolic syndrome comprises amelioration of at least one sign or symptom of insulin insufficiency.

22. The method of claim 1, wherein treating the metabolic syndrome comprises amelioration of at least one sign or symptom of hyperinsulinemia.

23. The method of claim 1, wherein treating the metabolic syndrome comprises amelioration of at least one sign or symptom of impaired glucose tolerance (IGT).

24. The method of claim 1, wherein treating the metabolic syndrome comprises amelioration of at least one sign or symptom of obesity.

25. The method of claim 1, wherein treating the metabolic syndrome comprises amelioration of at least one of
   a) Blood pressure equal to or higher than 130/85 mmHg;
   b) Fasting blood glucose equal to or higher than 100 mg/dL;
   c) Large waist circumference wherein a large waist circumference is 40 inches or more for men and 35 inches or more for women;
   d) Low HDL cholesterol wherein low HDL cholesterol is under 40 mg/dL for men and under 50 mg/dL; and
   e) Triglycerides equal to or higher than 150 mg/dL.

26. The method of claim 25, wherein treating the metabolic syndrome comprises amelioration of elevated blood pressure equal to or higher than 130/85 mmHg.

27. The method of claim 25, wherein treating the metabolic syndrome comprises amelioration of elevated fasting blood glucose equal to or higher than 100 mg/dL.

28. The method of claim 25, wherein treating the metabolic syndrome comprises amelioration of large waist circumference wherein a large waist circumference is 40 inches or more for men and 35 inches or more for women.

29. The method of claim 25, wherein treating the metabolic syndrome comprises amelioration of low HDL cholesterol by increasing HDL cholesterol wherein low HDL cholesterol is under 40 mg/dL for men and under 50 mg/dL.

30. The method of claim 25, wherein treating the metabolic syndrome comprises amelioration of elevated triglycerides equal to or higher than 150 mg/dL.

31. The method of claim 1, wherein treating metabolic syndrome comprises amelioration of fatty liver.

32. The method of claim 1, wherein treating metabolic syndrome comprises modulation of fat deposition.

* * * * *

SEQUENCE LISTING

```
<160> NUMBER OF SEQ ID NOS: 10

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1
aggccgacaa gaaugauaag gcagt                                          25

<210> SEQ ID NO 2
<211> LENGTH: 27
```

-continued

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
acugccuuau cauucuuguc ggccuca                                         27

<210> SEQ ID NO 3
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
caacgaugau gaacaguaug cuugg                                           25

<210> SEQ ID NO 4
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
ccaagcauac uguucaucau cguugug                                         27

<210> SEQ ID NO 5
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
cguugcucac uauuacguau aaucc                                           25

<210> SEQ ID NO 6
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
ggauuauacg uaauagugag caacgua                                         27

<210> SEQ ID NO 7
<211> LENGTH: 2565
<212> TYPE: DNA
<213> ORGANISM: Homo sapiens

<400> SEQUENCE: 7 atgccccgt gttcgggcgg ggacggctcc acccctcctg ggccctccct tcgggacagg      60
gactgtcccg cccagagtgc tgaatacccg cgcgaccgtc tggatccccg cccaggaagc   120
ccctctgaag cctcctcgcc gccgtttctg agaagcaggg cacctgttaa ctggtaccaa   180
gaaaaggccc aagtgtttct ctggcatctg ttggtgtctg gatccaccac tctactctgt   240
ctctggaaac agcccttcca cgtctctgca ttccctgtca ctgcgtcact ggccttcaga   300
```

```
cagagccaag gtgcagggca acacctctac aaggatctgc agccatttat attgcttagg    360
ctactgatgc ctgaggaaac ccagacccaa gaccaaccga tggaggagga ggaggttgag    420
acgttcgcct ttcaggcaga aattgcccag ttgatgtcat tgatcatcaa tactttctac    480
tcgaacaaag agatctttct gagagagctc atttcaaatt catcagatgc attggacaaa    540
atccggtatg aaagcttgac agatcccagt aaattagact ctgggaaaga gctgcatatt    600
aaccttatac cgaacaaaca agatcgaact ctcactattg tggatactgg aattggaatg    660
accaaggctg acttgatcaa taaccttggt actatcgcca agtctgggac caaagcgttc    720
atggaagctt gcaggctgg tgcagatatc tctatgattg ccagttcgg tgttggtttt    780
tattctgctt atttggttgc tgagaaagta actgtgatca ccaaacataa cgatgatgag    840
cagtacgctt gggagtcctc agcaggggga tcattcacag tgaggacaga cacaggtgaa    900
cctatgggtc gtggaacaaa agttatccta cacctgaaag aagaccaaac tgagtacttg    960
gaggaacgaa gaataaagga gattgtgaag aaacattctc agtttattgg atatcccatt   1020
actcttttg tggagaagga acgtgataaa gaagtaagcg atgatgaggc tgaagaaaag   1080
gaagacaaag aagaagaaaa agaaaaagaa gagaaagagt cggaagacaa acctgaaatt   1140
gaagatgttg gttctgatga ggaagaagaa aagaaggatg gtgacaagaa gaagaagaag   1200
aagattaagg aaaagtacat cgatcaagaa gagctcaaca aaacaaagcc catctggacc   1260
agaaatcccg acgatattac taatgaggag tacggagaat tctataagag cttgaccaat   1320
gactgggaag atcacttggc agtgaagcat ttttcagttg aaggacagtt ggaattcaga   1380
gcccttctat ttgtcccacg acgtgctcct tttgatctgt tgaaaacag aaagaaaag   1440
aacaatatca aattgtatgt acgcagagtt ttcatcatgg ataactgtga ggagctaatc   1500
cctgaatatc tgaacttcat tagaggggtg gtagactcgg aggatctccc tctaaacata   1560
tcccgtgaga tgttgcaaca aagcaaaatt ttgaaagtta tcaggaagaa tttggtcaaa   1620
aaatgcttag aactctttac tgaactggcg gaagataaag agaactacaa gaaattctat   1680
gagcagttct ctaaaaacat aaagcttgga atacacgaag actctcaaaa tcggaagaag   1740
cttttcagagc tgttaaggta ctacacatct gcctctggtg atgagatggt ttctctcaag   1800
gactactgca ccagaatgaa ggagaaccag aaacatatct attatatcac aggtgagacc   1860
aaggaccagg tagctaactc agcctttgtg gaacgtcttc ggaaacatgg cttagaagtg   1920
atctatatga ttgagcccat tgatgagtac tgtgtccaac agctgaagga atttgagggg   1980
aagactttag tgtcagtcac caaagaaggc ctggaacttc cagaggatga agaagagaaa   2040
aagaagcagg aagagaaaaa aacaaagttt gagaacctct gcaaaatcat gaaagacata   2100
ttggagaaaa aagttgaaaa ggtggttgtg tcaaaccgat tggtgacatc tccatgctgt   2160
attgtcacaa gcacatatgg ctggacagca acatggagag aatcatgaa agctcaagcc   2220
ctaagagaca actcaacaat gggttacatg gcagcaaaga acacctgga gataaaccct   2280
gaccattcca ttattgagac cttaaggcaa aaggcagagg ctgataagaa cgacaagtct   2340
gtgaaggatc tggtcatctt gcttatgaa actgcgctcc tgtcttctgg cttcagtctg   2400
gaagatcccc agacacatgc taacaggatc tacaggatga tcaaacttgg tctgggtatt   2460
gatgaagatg accctactgc tgatgatacc agtgctgctg taactgaaga aatgccaccc   2520
cttgaaggag atgacgacac atcacgcatg gaagaagtag actaa               2565
```

<210> SEQ ID NO 8

```
<211> LENGTH: 854
<212> TYPE: PRT
<213> ORGANISM: Homo sapiens

<400> SEQUENCE: 8
```

| | | | | | | | | | | | | | | |
|---|---|---|---|---|---|---|---|---|---|---|---|---|---|---|
| Met | Pro | Pro | Cys | Ser | Gly | Gly | Asp | Gly | Ser | Thr | Pro | Gly | Pro | Ser |
| 1 | | | | 5 | | | | | 10 | | | | | 15 |
| Leu | Arg | Asp | Arg | Asp | Cys | Pro | Ala | Gln | Ser | Ala | Glu | Tyr | Pro | Arg | Asp |
| | | | 20 | | | | | 25 | | | | | 30 | | |
| Arg | Leu | Asp | Pro | Arg | Pro | Gly | Ser | Pro | Ser | Glu | Ala | Ser | Ser | Pro | Pro |
| | | 35 | | | | | 40 | | | | | 45 | | | |
| Phe | Leu | Arg | Ser | Arg | Ala | Pro | Val | Asn | Trp | Tyr | Gln | Glu | Lys | Ala | Gln |
| 50 | | | | | 55 | | | | | 60 | | | | | |
| Val | Phe | Leu | Trp | His | Leu | Val | Ser | Gly | Ser | Thr | Thr | Leu | Leu | Cys |
| 65 | | | | 70 | | | | | 75 | | | | | 80 |
| Leu | Trp | Lys | Gln | Pro | Phe | His | Val | Ser | Ala | Phe | Pro | Val | Thr | Ala | Ser |
| | | | | 85 | | | | | 90 | | | | | 95 | |
| Leu | Ala | Phe | Arg | Gln | Ser | Gln | Gly | Ala | Gly | Gln | His | Leu | Tyr | Lys | Asp |
| | | | 100 | | | | | 105 | | | | | 110 | | |
| Leu | Gln | Pro | Phe | Ile | Leu | Leu | Arg | Leu | Leu | Met | Pro | Glu | Glu | Thr | Gln |
| | | 115 | | | | | 120 | | | | | 125 | | | |
| Thr | Gln | Asp | Gln | Pro | Met | Glu | Glu | Glu | Val | Glu | Thr | Phe | Ala | Phe |
| 130 | | | | | 135 | | | | | 140 | | | | | |
| Gln | Ala | Glu | Ile | Ala | Gln | Leu | Met | Ser | Leu | Ile | Ile | Asn | Thr | Phe | Tyr |
| 145 | | | | | 150 | | | | | 155 | | | | | 160 |
| Ser | Asn | Lys | Glu | Ile | Phe | Leu | Arg | Glu | Leu | Ile | Ser | Asn | Ser | Ser | Asp |
| | | | | 165 | | | | | 170 | | | | | 175 | |
| Ala | Leu | Asp | Lys | Ile | Arg | Tyr | Glu | Ser | Leu | Thr | Asp | Pro | Ser | Lys | Leu |
| | | | 180 | | | | | 185 | | | | | 190 | | |
| Asp | Ser | Gly | Lys | Glu | Leu | His | Ile | Asn | Leu | Ile | Pro | Asn | Lys | Gln | Asp |
| | | 195 | | | | | 200 | | | | | 205 | | | |
| Arg | Thr | Leu | Thr | Ile | Val | Asp | Thr | Gly | Ile | Gly | Met | Thr | Lys | Ala | Asp |
| 210 | | | | | 215 | | | | | 220 | | | | | |
| Leu | Ile | Asn | Asn | Leu | Gly | Thr | Ile | Ala | Lys | Ser | Gly | Thr | Lys | Ala | Phe |
| 225 | | | | | 230 | | | | | 235 | | | | | 240 |
| Met | Glu | Ala | Leu | Gln | Ala | Gly | Ala | Asp | Ile | Ser | Met | Ile | Gly | Gln | Phe |
| | | | | 245 | | | | | 250 | | | | | 255 | |
| Gly | Val | Gly | Phe | Tyr | Ser | Ala | Tyr | Leu | Val | Ala | Glu | Lys | Val | Thr | Val |
| | | | 260 | | | | | 265 | | | | | 270 | | |
| Ile | Thr | Lys | His | Asn | Asp | Asp | Glu | Gln | Tyr | Ala | Trp | Glu | Ser | Ser | Ala |
| | | 275 | | | | | 280 | | | | | 285 | | | |
| Gly | Gly | Ser | Phe | Thr | Val | Arg | Thr | Asp | Thr | Gly | Glu | Pro | Met | Gly | Arg |
| 290 | | | | | 295 | | | | | 300 | | | | | |
| Gly | Thr | Lys | Val | Ile | Leu | His | Leu | Lys | Glu | Asp | Gln | Thr | Glu | Tyr | Leu |
| 305 | | | | | 310 | | | | | 315 | | | | | 320 |
| Glu | Glu | Arg | Arg | Ile | Lys | Glu | Ile | Val | Lys | Lys | His | Ser | Gln | Phe | Ile |
| | | | | 325 | | | | | 330 | | | | | 335 | |
| Gly | Tyr | Pro | Ile | Thr | Leu | Phe | Val | Glu | Lys | Glu | Arg | Asp | Lys | Glu | Val |
| | | | 340 | | | | | 345 | | | | | 350 | | |
| Ser | Asp | Asp | Glu | Ala | Glu | Glu | Lys | Glu | Asp | Lys | Glu | Glu | Lys | Glu |
| | | 355 | | | | | 360 | | | | | 365 | | | |
| Lys | Glu | Glu | Lys | Glu | Ser | Glu | Asp | Lys | Pro | Glu | Ile | Glu | Asp | Val | Gly |
| 370 | | | | | 375 | | | | | 380 | | | | | |
| Ser | Asp | Glu | Glu | Glu | Glu | Lys | Lys | Asp | Gly | Asp | Lys | Lys | Lys | Lys |

```
                385                 390                 395                 400
Lys Ile Lys Glu Lys Tyr Ile Asp Gln Glu Glu Leu Asn Lys Thr Lys
                    405                 410                 415
Pro Ile Trp Thr Arg Asn Pro Asp Ile Thr Asn Glu Glu Tyr Gly
                420                 425                 430
Glu Phe Tyr Lys Ser Leu Thr Asn Asp Trp Glu Asp His Leu Ala Val
                    435                 440                 445
Lys His Phe Ser Val Glu Gly Gln Leu Glu Phe Arg Ala Leu Leu Phe
    450                 455                 460
Val Pro Arg Arg Ala Pro Phe Asp Leu Phe Glu Asn Arg Lys Lys Lys
465                 470                 475                 480
Asn Asn Ile Lys Leu Tyr Val Arg Arg Val Phe Ile Met Asp Asn Cys
                    485                 490                 495
Glu Glu Leu Ile Pro Glu Tyr Leu Asn Phe Ile Arg Gly Val Val Asp
                500                 505                 510
Ser Glu Asp Leu Pro Leu Asn Ile Ser Arg Glu Met Leu Gln Gln Ser
            515                 520                 525
Lys Ile Leu Lys Val Ile Arg Lys Asn Leu Val Lys Lys Cys Leu Glu
    530                 535                 540
Leu Phe Thr Glu Leu Ala Glu Asp Lys Glu Asn Tyr Lys Lys Phe Tyr
545                 550                 555                 560
Glu Gln Phe Ser Lys Asn Ile Lys Leu Gly Ile His Glu Asp Ser Gln
                565                 570                 575
Asn Arg Lys Lys Leu Ser Glu Leu Leu Arg Tyr Tyr Thr Ser Ala Ser
                580                 585                 590
Gly Asp Glu Met Val Ser Leu Lys Asp Tyr Cys Thr Arg Met Lys Glu
            595                 600                 605
Asn Gln Lys His Ile Tyr Tyr Ile Thr Gly Glu Thr Lys Asp Gln Val
        610                 615                 620
Ala Asn Ser Ala Phe Val Glu Arg Leu Arg Lys His Gly Leu Glu Val
625                 630                 635                 640
Ile Tyr Met Ile Glu Pro Ile Asp Glu Tyr Cys Val Gln Gln Leu Lys
                645                 650                 655
Glu Phe Glu Gly Lys Thr Leu Val Ser Val Thr Lys Glu Gly Leu Glu
                660                 665                 670
Leu Pro Glu Asp Glu Glu Glu Lys Lys Lys Gln Glu Glu Lys Lys Thr
            675                 680                 685
Lys Phe Glu Asn Leu Cys Lys Ile Met Lys Asp Ile Leu Glu Lys Lys
        690                 695                 700
Val Glu Lys Val Val Val Ser Asn Arg Leu Val Thr Ser Pro Cys Cys
705                 710                 715                 720
Ile Val Thr Ser Thr Tyr Gly Trp Thr Ala Asn Met Glu Arg Ile Met
                725                 730                 735
Lys Ala Gln Ala Leu Arg Asp Asn Ser Thr Met Gly Tyr Met Ala Ala
                740                 745                 750
Lys Lys His Leu Glu Ile Asn Pro Asp His Ser Ile Ile Glu Thr Leu
        755                 760                 765
Arg Gln Lys Ala Glu Ala Asp Lys Asn Asp Lys Ser Val Lys Asp Leu
        770                 775                 780
Val Ile Leu Leu Tyr Glu Thr Ala Leu Leu Ser Ser Gly Phe Ser Leu
785                 790                 795                 800
Glu Asp Pro Gln Thr His Ala Asn Arg Ile Tyr Arg Met Ile Lys Leu
                805                 810                 815
```

Gly Leu Gly Ile Asp Glu Asp Pro Thr Ala Asp Asp Thr Ser Ala
         820                 825                 830

Ala Val Thr Glu Glu Met Pro Pro Leu Glu Gly Asp Asp Thr Ser
         835                 840                 845

Arg Met Glu Glu Val Asp
    850

<210> SEQ ID NO 9
<211> LENGTH: 2567
<212> TYPE: DNA
<213> ORGANISM: Homo sapiens

<400> SEQUENCE: 9

```
ctccggcgca gtgttgggac tgtctgggta tcggaaagca agcctacgtt gctcactatt     60
acgtataatc cttttctttt caagatgcct gaggaagtgc accatggaga ggaggaggtg    120
gagacttttg cctttcaggc agaaattgcc caactcatgt ccctcatcat caataccttc    180
tattccaaca aggagatttt ccttcgggag ttgatctcta atgcttctga tgccttggac    240
aagattcgct atgagagcct gacagaccct tcgaagttgg acagtggtaa agagctgaaa    300
attgacatca tccccaaccc tcaggaacgt accctgactt tggtagacac aggcattggc    360
atgaccaaag ctgatctcat aaataatttg gaaccattg ccaagtctgg tactaaagca    420
ttcatggagg ctcttcaggc tggtgcagac atctccatga ttgggcagtt tggtgttggc    480
ttttattctg cctacttggt ggcagagaaa gtggttgtga tcacaaagca caacgatgat    540
gaacagtatg cttgggagtc ttctgctgga ggttccttca ctgtgcgtgc tgaccatggt    600
gagcccattg cagggtac caaagtgatc ctccatctta agaagatca gacagagtac    660
ctagaagaga ggcgggtcaa agaagtagtg aagaagcatt ctcagttcat aggctatccc    720
atcacccttt atttggagaa ggaacgagag aaggaaatta gtgatgatga ggcagaggaa    780
gagaaaggtg agaaagaaga ggaagataaa gatgatgaag aaaaacccaa gatcgaagat    840
gtgggttcag atgaggagga tgacagcggt aaggataaga gaagaaaac taagaagatc    900
aaagagaaat acattgatca ggaagaacta aacaagacca gcctatttg gaccagaaac    960
cctgatgaca tcacccaaga ggagtatgga gaattctaca gagcctcac taatgactgg   1020
gaagaccact tggcagtcaa gcactttttct gtagaaggtc agttggaatt cagggcattg   1080
ctatttattc ctcgtcgggc tccctttgac cttttttgaga acaagaagaa aagaacaac   1140
atcaaactct atgtccgccg tgtgttcatc atggacagct gtgatgagtt gataccagag   1200
tatctcaatt ttatccgtgg tgtggttgac tctgaggatc tgcccctgaa catctcccga   1260
gaaatgctcc agcagagcaa aatcttgaaa gtcattcgca aaaacattgt taagaagtgc   1320
cttgagctct ctctctgagct ggcagaagac aaggagaatt acaagaaatt ctatgaggca   1380
ttctctaaaa atctcaagct tggaatccac gaagactcca ctaaccgccg ccgcctgtct   1440
gagctgctgc gctatcatac ctcccagtct ggagatgaga tgacatctct gtcagagtat   1500
gtttctcgca tgaaggagac acagaagtcc atctattaca tcactggtga gagcaaagag   1560
caggtggcca actcagcttt tgtggagcga gtgcggaaac ggggcttcga ggtggtatat   1620
atgaccgagc ccattgacga gtactgtgtg cagcagctca ggaatttga tgggaagagc   1680
ctggtctcag ttaccaagga gggtctggag ctgcctgagg atgaggagga gaagaagaag   1740
atggaagaga gcaaggcaaa gtttgagaac ctctgcaagc tcatgaaaga aatcttagat   1800
aagaaggttg agaaggtgac aatctccaat agacttgtgt cttcaccttg ctgcattgtg   1860
```

```
accagcacct acggctggac agccaatatg gagcggatca tgaaagccca ggcacttcgg    1920
gacaactcca ccatgggcta tatgatggcc aaaaagcacc tggagatcaa ccctgaccac    1980
cccattgtgg agacgctgcg gcagaaggct gaggccgaca agaatgataa ggcagttaag    2040
gacctggtgg tgctgctgtt tgaaaccgcc ctgctatctt ctggcttttc ccttgaggat    2100
ccccagaccc actccaaccg catctatcgc atgatcaagc taggtctagg tattgatgaa    2160
gatgaagtgg cagcagagga acccaatgct gcagttcctg atgagatccc ccctctcgag    2220
ggcgatgagg atgcgtctcg catggaagaa gtcgattagg ttaggagttc atagttggaa    2280
aacttgtgcc cttgtatagt gtccccatgg gctcccactg cagcctcgag tgcccctgtc    2340
ccacctggct cccctgctg tgtctagtg ttttttcc tctcctgtcc ttgtgttgaa        2400
ggcagtaaac taagggtgtc aagccccatt ccctctctac tcttgacagc aggattggat    2460
gttgtgtatt gtggtttatt ttattttctt cattttgttc tgaaattaaa gtatgcaaaa    2520
taaagaatat gccgttttaa aaaaaaaaaa aaaaaaaaaa aaaaaaa                  2567
```

<210> SEQ ID NO 10
<211> LENGTH: 724
<212> TYPE: PRT
<213> ORGANISM: Homo sapiens

<400> SEQUENCE: 10

```
Met Pro Glu Glu Val His His Gly Glu Glu Val Glu Thr Phe Ala
1               5                  10                  15

Phe Gln Ala Glu Ile Ala Gln Leu Met Ser Leu Ile Ile Asn Thr Phe
            20                  25                  30

Tyr Ser Asn Lys Glu Ile Phe Leu Arg Glu Leu Ile Ser Asn Ala Ser
        35                  40                  45

Asp Ala Leu Asp Lys Ile Arg Tyr Glu Ser Leu Thr Asp Pro Ser Lys
    50                  55                  60

Leu Asp Ser Gly Lys Glu Leu Lys Ile Asp Ile Pro Asn Pro Gln
65                  70                  75                  80

Glu Arg Thr Leu Thr Leu Val Asp Thr Gly Ile Gly Met Thr Lys Ala
                85                  90                  95

Asp Leu Ile Asn Asn Leu Gly Thr Ile Ala Lys Ser Gly Thr Lys Ala
            100                 105                 110

Phe Met Glu Ala Leu Gln Ala Gly Ala Asp Ile Ser Met Ile Gly Gln
        115                 120                 125

Phe Gly Val Gly Phe Tyr Ser Ala Tyr Leu Val Ala Glu Lys Val Val
    130                 135                 140

Val Ile Thr Lys His Asn Asp Asp Glu Gln Tyr Ala Trp Glu Ser Ser
145                 150                 155                 160

Ala Gly Gly Ser Phe Thr Val Arg Ala Asp His Gly Glu Pro Ile Gly
                165                 170                 175

Arg Gly Thr Lys Val Ile Leu His Leu Lys Glu Asp Gln Thr Glu Tyr
            180                 185                 190

Leu Glu Glu Arg Arg Val Lys Glu Val Val Lys His Ser Gln Phe
        195                 200                 205

Ile Gly Tyr Pro Ile Thr Leu Tyr Leu Glu Lys Arg Glu Lys Glu
    210                 215                 220

Ile Ser Asp Asp Glu Ala Glu Glu Lys Gly Glu Lys Glu Glu
225                 230                 235                 240

Asp Lys Asp Asp Glu Glu Lys Pro Lys Ile Glu Asp Val Gly Ser Asp
```

-continued

```
                245                 250                 255
Glu Glu Asp Asp Ser Gly Lys Asp Lys Lys Lys Thr Lys Lys Ile
            260                 265                 270
Lys Glu Lys Tyr Ile Asp Gln Glu Glu Leu Asn Lys Thr Lys Pro Ile
                275                 280                 285
Trp Thr Arg Asn Pro Asp Asp Ile Thr Gln Glu Glu Tyr Gly Glu Phe
            290                 295                 300
Tyr Lys Ser Leu Thr Asn Asp Trp Glu Asp His Leu Ala Val Lys His
305                 310                 315                 320
Phe Ser Val Glu Gly Gln Leu Glu Phe Arg Ala Leu Leu Phe Ile Pro
                325                 330                 335
Arg Arg Ala Pro Phe Asp Leu Phe Glu Asn Lys Lys Lys Asn Asn
            340                 345                 350
Ile Lys Leu Tyr Val Arg Arg Val Phe Ile Met Asp Ser Cys Asp Glu
                355                 360                 365
Leu Ile Pro Glu Tyr Leu Asn Phe Ile Arg Gly Val Val Asp Ser Glu
            370                 375                 380
Asp Leu Pro Leu Asn Ile Ser Arg Glu Met Leu Gln Gln Ser Lys Ile
385                 390                 395                 400
Leu Lys Val Ile Arg Lys Asn Ile Val Lys Lys Cys Leu Glu Leu Phe
                405                 410                 415
Ser Glu Leu Ala Glu Asp Lys Glu Asn Tyr Lys Lys Phe Tyr Glu Ala
            420                 425                 430
Phe Ser Lys Asn Leu Lys Leu Gly Ile His Glu Asp Ser Thr Asn Arg
            435                 440                 445
Arg Arg Leu Ser Glu Leu Leu Arg Tyr His Thr Ser Gln Ser Gly Asp
            450                 455                 460
Glu Met Thr Ser Leu Ser Glu Tyr Val Ser Arg Met Lys Glu Thr Gln
465                 470                 475                 480
Lys Ser Ile Tyr Tyr Ile Thr Gly Glu Ser Lys Glu Gln Val Ala Asn
                485                 490                 495
Ser Ala Phe Val Glu Arg Val Arg Lys Arg Gly Phe Glu Val Val Tyr
            500                 505                 510
Met Thr Glu Pro Ile Asp Glu Tyr Cys Val Gln Gln Leu Lys Glu Phe
            515                 520                 525
Asp Gly Lys Ser Leu Val Ser Val Thr Lys Glu Gly Leu Glu Leu Pro
            530                 535                 540
Glu Asp Glu Glu Glu Lys Lys Lys Met Glu Glu Ser Lys Ala Lys Phe
545                 550                 555                 560
Glu Asn Leu Cys Lys Leu Met Lys Glu Ile Leu Asp Lys Lys Val Glu
                565                 570                 575
Lys Val Thr Ile Ser Asn Arg Leu Val Ser Ser Pro Cys Cys Ile Val
            580                 585                 590
Thr Ser Thr Tyr Gly Trp Thr Ala Asn Met Glu Arg Ile Met Lys Ala
            595                 600                 605
Gln Ala Leu Arg Asp Asn Ser Thr Met Gly Tyr Met Met Ala Lys Lys
            610                 615                 620
His Leu Glu Ile Asn Pro Asp His Pro Ile Val Glu Thr Leu Arg Gln
625                 630                 635                 640
Lys Ala Glu Ala Asp Lys Asn Asp Lys Ala Val Lys Asp Leu Val Val
                645                 650                 655
Leu Leu Phe Glu Thr Ala Leu Leu Ser Ser Gly Phe Ser Leu Glu Asp
            660                 665                 670
```

```
Pro Gln Thr His Ser Asn Arg Ile Tyr Arg Met Ile Lys Leu Gly Leu
        675                 680                 685

Gly Ile Asp Glu Asp Glu Val Ala Ala Glu Glu Pro Asn Ala Ala Val
        690                 695                 700

Pro Asp Glu Ile Pro Pro Leu Glu Gly Asp Glu Asp Ala Ser Arg Met
705                 710                 715                 720

Glu Glu Val Asp
```